United States Patent [19]

Sunagawa et al.

[11] Patent Number: 5,122,604

[45] Date of Patent: * Jun. 16, 1992

[54] β-LACTAM COMPOUNDS

[75] Inventors: Makoto Sunagawa; Haruki Matsumura, both of Osaka; Takaaki Inoue; Masatomo Fukasawa, both of Hyogo; Masuhiro Kato, Osaka, all of Japan

[73] Assignee: Sumitomo Pharmaceuticals Co., Ltd., Osaka, Japan

[*] Notice: The portion of the term of this patent subsequent to Dec. 19, 2006 has been disclaimed.

[21] Appl. No.: 525,817

[22] Filed: May 21, 1990

Related U.S. Application Data

[63] Continuation of Ser. No. 106,036, Oct. 8, 1987, Pat. No. 4,943,569, which is a continuation of Ser. No. 608,618, May 9, 1984, abandoned.

[30] Foreign Application Priority Data

May 9, 1983 [JP] Japan ................... 58-081443
Jun. 15, 1983 [JP] Japan ................... 58-108472
Jul. 12, 1983 [JP] Japan ................... 58-127485
Sep. 9, 1983 [JP] Japan ................... 58-166938
Nov. 11, 1983 [JP] Japan ................... 58-212857
Feb. 10, 1984 [JP] Japan ................... 59-023497

[51] Int. Cl.$^5$ ................... C07D 487/04; A61K 31/40
[52] U.S. Cl. ................... 540/350
[58] Field of Search ................... 540/310, 350; 514/210

[56] References Cited

U.S. PATENT DOCUMENTS 4,888,344  12/1989  Sunagawa et al. ................. 540/350
4,943,569   7/1990  Sunagawa ........................... 540/350
4,962,103  10/1990  Sunagawa et al. ................. 540/350

FOREIGN PATENT DOCUMENTS 59-16892  7/1982  Japan .

Primary Examiner—Nicholas S. Rizzo
Attorney, Agent, or Firm—Sughrue, Mion, Zinn, Macpeak & Seas

[57] ABSTRACT

Novel β-lactam compounds belonging to carbapenem or penem derivatives useful as antimicrobial agents or intermediates therefor and a process for producing these compounds are disclosed.

1 Claim, No Drawings

β-LACTAM COMPOUNDS

This is a continuation of application Ser. No. 07/106,036 filed Oct. 8, 1987, now U.S. Pat. No. 4,943,569 in turn a continuation application of Ser. No. 06/608,618 filed May 9, 1984, now abandoned.

FIELD OF THE INVENTION

This invention relates to novel β-lactam compounds and a process for producing the same. More particularly, this invention relates to novel β-lactam compounds belonging to carbapenem or penem derivatives and useful as antimicrobial agents or intermediates therefor and a process for producing the same.

BACKGROUND OF THE INVENTION

Since the discovery of thienamycin having a potential antimicrobial activity against Gram negative and Gram positive bacteria, studies on syntheses of carbapenem or penem derivatives which are analoguous to thienamycin have been widely developed.

The present inventors have conducted intensive investigations on syntheses of carbapenem or penem derivatives and, as a result, found that carbapenem or penem derivatives having, as their 2-side chain, a substituent easily derived from 4-hydroxy-proline, i.e., a substituted pyrrolidinyl group carrying a carbonyl group substituted with various substituents on its 2-position, exhibit potential antimicrobial activity and are useful as medicines or are important intermediates for compounds possessing antimicrobial activity, and thus completed the present invention.

SUMMARY OF THE INVENTION

The present invention relates to a novel β-lactam compound represented by the formula (I):

wherein $R_1$ represents a hydrogen atom, 1-hydroxyethyl group or a 1-hydroxyethyl group in which the hydroxy group is protected with a protecting group; $R_2$ represents a hydrogen atom or a protecting group for an amino group; $R_3$ represents a hydrogen atom or a protecting group for a carboxyl group; X represents a substituted or unsubstituted methylene group of the formula (1):

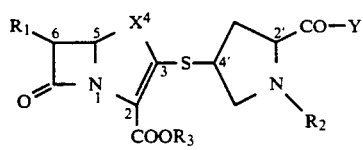

wherein $R_4$ represents a hydrogen atom or an alkyl group having 1 to 3 carbon atoms, or a sulfur atom; and Y represents a group of the formula (2):

wherein $R_5$ and $R_6$, which may be the same or different, each represents a hydrogen atom, an alkyl group having 1 to 5 carbon atoms, an alkenyl group having 3 to 4 carbon atoms, an aralkyl group having 1 to 3 carbon atoms in its alkyl moiety, a substituted alkyl group having 1 to 5 carbon atoms or a pyridyl group, or $R_5$ and $R_6$ are taken together to represent an alkylene chain or alkylene chain via an oxygen atom, a sulfur atom or a ($C_1$–$C_3$)alkyl-substituted nitrogen atom to form, together with the adjacent nitrogen atom, a substituted or unsubstituted 3- to 7-membered cyclic amino group which may contain double bond(s) in its ring, a substituted or unsubstituted guanidyl group of the formula (3):

$$-N=C\begin{matrix}N(R_7)_2\\N(R_7)_2\end{matrix} \quad (3)$$

wherein $R_7$ represents a hydrogen atom or an alkyl group having 1 to 3 carbon atoms, a protected or unprotected hydroxyl group, an alkoxy group having 1 to 3 carbon atoms, an unsubstituted or ($C_1$–$C_3$)alkyl-substituted hydrazino group or a group of the formula (4):

$$-NHOR_8 \quad (4)$$

wherein $R_8$ represents a hydrogen atom, a protecting group for a hydroxyl group or an alkyl group having 1 to 3 carbon atoms, and a pharmacologically acceptable salt thereof, and a process for producing the same.

DETAILED DESCRIPTION OF THE INVENTION

In the above-described formula (I), the protecting group for a hydroxyl group as represented by $R_1$ and the protecting group for an amino group as represented by $R_2$ may be any of those commonly employed. Preferred examples of these protecting groups include a lower alkoxycarbonyl group, e.g., t-butyloxycarbonyl, etc.; a halogenoalkoxycarbonyl group, e.g., 2-iodoethyloxycarbonyl, 2,2,2-trichloroethyloxycarbonyl, etc.; an aralkyloxycarbonyl group, e.g., benzyloxycarbonyl, p-methoxbenzyloxycarbonyl, o-nitrobenzyloxycarbonyl, p-nitrobenzyloxycarbonyl, etc.; and a trialkylsilyl group, e.g., trimethylsilyl, t-butyldimethylsilyl, etc.

The protecting group for a carboxyl group as represented by $R_3$ may be any of those commonly employed and preferably includes, for example, a straight or branched chain lower alkyl group, e.g., methyl, ethyl, isopropyl, t-butyl, etc.; a halogeno lower alkyl group, e.g., 2-iodoethyl, 2,2,2-trichloroethyl, etc.; a lower alkoxymethyl group, e.g., methoxymethyl, ethoxymethyl, isobutoxymethyl, etc.; a lower aliphatic acyloxymethyl group, e.g., acetoxymethyl, propionyloxymethyl, butyryloxymethyl, pivaloyloxymethyl, etc.; a 1-lower alkoxycarbonyloxyethyl group, e.g., 1-methoxycarbonyloxyethyl, 1-ethoxycarbonyloxyethyl, etc.; an aralkyl group, e.g., p-methoxybenzyl, o-nitrobenzyl, p-nitrobenzyl, etc.; a benzhydryl group and a phthalidyl group.

When X is a $(C_1-C_3)$alkyl-substituted or unsubstituted methylene group as represented by the formula (1), the $(C_1-C_3)$ alkyl group includes, for example, methyl, ethyl, n-propyl, etc.

When Y is an amino group represented by the formula (2), $R_5$ and $R_6$ may be the same or different from each other. In the definition for $R_5$ and $R_6$, the alkyl group having 1 to 5 carbon atoms includes methyl, ethyl, n-propyl, isopropyl, n-butyl, t-butyl, etc.; the alkenyl group having 3 to 4 carbon atoms includes, for example, propenyl, butenyl, etc.; the aralkyl group having 1 to 3 carbon atoms in its alkyl moiety includes, for example, a phenyl group, a substituted phenyl group, a pyridyl group and a $(C_1-C_3)$ alkyl group substituted with a substituted pyridyl group, such as benzyl, substituted benzyl, phenethyl, 2-pyridylmethyl, 3-pyridylmethyl, 4-pyridylmethyl, etc.; the substituted alkyl group having 1 to 5 carbon atoms includes, for example, a straight chain or branched chain alkyl group, e.g., methyl, ethyl, n-propyl, isopropyl, n-butyl, etc., which is substituted with a hydroxyl group, a di-$(C_1-C_3)$ alkylamino group, a carbamoyl group, a mono- or di-$C_1-C_3$) alkyl-substituted aminocarbonyl group, a protected or unprotected carboxyl group or a like substituent; and the pyridyl group includes 2-pyridyl, 3pyridyl and 4-pyridyl groups.

In cases where $R_5$ and $R_6$ jointly represent an alkylene chain or an alkylene chain via an oxygen atom, a sulfur atom or a $(C_1-C_3)$ alkyl-substituted nitrogen atom to form, together with the adjacent nitrogen atom, a substituted or unsubstituted 3- to 7-membered cyclic amino group which may contain double bond(s) in its ring, the cyclic amino group includes, for example, a saturated cyclic amino group, e.g., an aziridino group, an azetidino group, a pyrrolidino group, a piperidino group, etc.; an unsaturated cyclic amino group, e.g., a pyrrolyl group, a 3-pyrrolinyl group, etc.; and a cyclic amino group having an oxygen atom, a sulfur atom or an alkyl-substituted nitrogen atom in its ring, e.g., a morpholino group, a thiomorpholino group, an N-methylpiperazino group, etc. The substituents for these cyclic amino groups include, for example, an alkyl group having 1 to 3 carbon atoms, a carbamoyl group, a mono- or di-$(C_1-C_3)$alkyl-substituted aminocarbonyl group, a hydroxyl group, etc.

When Y is represented by the formula (3), the guanidyl group unsubstituted or substituted with a $(C_1-C_3)$ alkyl group includes a guanidyl group and a guanidyl group substituted with one to four alkyl groups, e.g., methyl, ethyl, n-propyl, isopropyl, etc., such as an N,N'-tetramethylguanidyl group.

The hydrazino group for Y includes, for example, a hydrazino group and a hydrazino group substituted with one to three alkyl groups, e.g., methyl, ethyl, n-propyl, isopropyl, etc., such as 2',2'-dimethylhydrazino, trimethylhydrazino, etc.

In cases where Y is represented by the formula (4), $R_8$ is a hydrogen atom, a protecting group commonly employed for protection of a hydroxyl group or a lower alkyl group, e.g., methyl, ethyl, n-propyl, etc.

Of the compounds of the above-described formula (I), the carboxylic acid compounds wherein the group as represented by $-COOR_3$ or $-COY$ is a carboxyl group can be converted into their pharmacologically acceptable salts, if desired. Such salts include those formed with inorganic metals, such as lithium, sodium, potassium, calcium, magnesium, etc. and those formed with ammonium, such as ammonium, cyclohexylammonium, diisopropylammonium, triethylammonium, etc., with a sodium salt and a potassium salt being preferred.

The preferred compounds of the formula (I) are those wherein $R_1$ is a hydrogen atom or a 1-hydroxyethyl group; $R_2$ and $R_3$ are both hydrogen atoms; and Y is a group represented by the formula (2-a):

wherein $R_{5-a}$ and $R_{6-a}$ each represents a hydrogen atom, an alkyl group having 1 to 5 carbon atoms, an alkenyl group having 3 to 4 carbon atoms, an aralkyl group having 1 to 3 carbon atoms in its alkyl moiety, an alkyl group having 1 to 5 carbon atoms which is substituted with a hydroxyl group, a di-$(C_1-C_3)$alkylamino group, a carbamoyl group, a mono- or di-$(C_1-C_3)$alkyl-substituted aminocarbonyl group, a carboxyl group, etc., or a pyridyl group, or $R_{5-a}$ and $R_{6-a}$ jointly represent an alkylene chain or an alkylene chain via an oxygen atom, a sulfur atom or a $(C_1-C_3)$alkyl-substituted nitrogen atom to form, together with the adjacent nitrogen atom, a substituted or unsubstituted 3- to 7-membered cyclic amino group which may contain double bond(s) in the ring thereof, wherein the substituent for the cyclic amino group includes a $(C_1-C_3)$alkyl group, a carbamoyl group, a carboxyl group, a mono- or di-$(C_1-C_3)$ alkyl-substituted aminocarbonyl group, a hydroxyl group, etc.; an unsubstituted or $(C_1-C_3)$alkyl-substituted guanidyl group; a hydroxyl group; an alkoxy group having 1 to 3 carbon atoms; an unsubstituted or $(C_1-C_3)$alkyl-substituted hydrazino group; or a group represented by the formula (4-a):

wherein $R_{8-a}$ represents a hydrogen atom or an alkyl group having 1 to 3 carbon atoms.

The more preferred compounds of the formula (I) are those wherein $R_1$ is a 1-hydroxylethyl group; $R_2$ and $R_3$ are both hydrogen atoms; and Y is a group represented by the formula (2-b):

wherein $R_{5-b}$ and $R_{6-b}$ each represents a hydrogen atom, an alkyl group having 1 to 5 carbon atoms, an alkenyl group having 3 to 4 carbon atoms, an aralkyl group having 1 to 3 carbon atoms in its alkyl moiety, an alkyl group having 1 to 5 carbon atoms which is substituted with a hydroxyl group, a di-$(C_1-C_3)$alkylamino group, a carbamoyl group, a mono- or di-$(C_1-C_3)$alkyl-substituted aminocarbonyl group, a carboxyl group, etc., or a pyridyl group, or $R_{5-b}$ and $R_{6-b}$ jointly represents an alkylene chain or alkylene chain via an oxygen atom, a sulfur atom or a $(C_1-C_3)$alkyl-substituted nitrogen atom to form, together with the adjacent nitrogen atom, a substituted or unsubstituted 3- to 7-membered cyclic amino group which may contain double bond(s) in its ring, wherein the substituent for the cyclic amino group includes an alkyl group having 1 to 3 carbon atoms, a carbamoyl group, a hydroxyl group, etc.,: an unsubstituted or (C₁-C₃)alkyl-substituted guanidyl group; a hydroxyl group; an alkoxy group having 1 to 3 carbon atoms, preferably a methoxy group; an unsubstituted or (C₁-C₃)alkyl-substituted hydrazino group; or a group represented by the formula (4-a):

—NHOR$_{8\text{-}a}$    (4-a)

wherein R$_{8\text{-}a}$ has the same meaning as defined above.

The most preferred compounds of the formula (I) are those wherein R$_1$ is a 1-hydroxyethyl group; R$_2$ and R$_3$ are both hydrogen atoms; and Y is a group represented by the formula (2-c):

wherein R$_{5\text{-}c}$ and R$_{6\text{-}c}$ have either one of the following meanings:

(1) R$_{5\text{-}c}$ represents an alkyl group having 1 to 5 carbon atoms which may be substituted with a carbamoyl group, a mono- or di-(C₁-C₃)alkylaminocarbonyl group, a hydroxyl group, etc., or a pyridyl group, and R$_{6\text{-}c}$ represents a hydrogen atom or has the same meaning as described for R$_{5\text{-}c}$;

(2) R$_{5\text{-}c}$ and R$_{6\text{-}c}$ are directly taken together to represent an alkylene chain to form, together with the adjacent nitrogen atom, a 4- to 6-membered saturated cyclic amino group or a 5- to 6-membered unsaturated cyclic amino group having double bond(s) in its ring, such as a pyrrolinyl group, or the same saturated or unsaturated cyclic amino group as described above but having a substituent on its ring, such as a carbamoyl group, a hydroxyl group, etc.; and (3) R$_{5\text{-}c}$ and R$_{6\text{-}c}$ jointly represent an alkylene chain via an oxygen atom or a (C₁-C₃)alkyl-substituted nitrogen atom to form, together with the adjacent nitrogen atom, a 6-membered cyclic amino group.

Preferred examples of X, if positively enumerated, can include a methyl-substituted or unsubstituted methylene group represented by the formula (1-a):

wherein R$_{4\text{-}a}$ represents a hydrogen atom or a methyl group, with a group

being particularly preferred.

The β-lactum compounds represented by the formula (I) according to the present invention are novel compounds belonging to carbapenem (i.e., 1-azabicyclo[3.2.0]hept-2-ene-7-one-2-caboxylic acid) derivatives or penem (i.e., 1-azabicyclo[3.2.0]hept-2-ene-7-one-4-thia-2-carboxylic acid) derivatives.

A process for producing the compounds of the formula (I) according to the present invention will be described below.

Of the β-lactam compounds of the formula (I), compounds represented by the formula (IV):

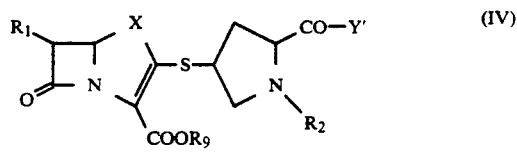

wherein R$_1$, R$_2$ and X are as defined above; R$_9$ represents a protecting group for a carboxyl group; and Y' represents the group as represented by the foresaid formula (2), the group as represented by the aforesaid formula (3), a protected hydroxyl group, an alkoxy group having 1 to 3 carbon atoms, an unsubstituted or (C₁-C₁₃)alkyl-substituted hydrazino group or a group represented by the formula (4'):

—NHOR$_8'$    (4')

wherein R$_8'$ represents a protecting group for a hydroxyl group or an alkyl group having 1 to 3 carbon atoms, can be prepared by reacting a β-lactam derivative represented by the formula (II):

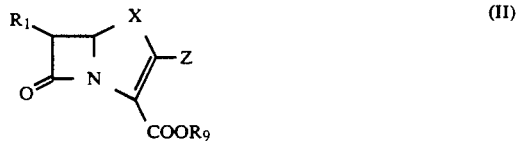

wherein R$_1$, X and R$_9$ are as defined above, and Z represents a reactive ester group of an alcohol or a substituted or unsubstituted lower alkylsulfinyl group, with a mercaptan derivative represented by the formula (III):

wherein R$_2$ and Y' are as defined above, in an inert solvent in the presence of a base.

The term "reactive ester group of an alcohol" herein used means a group derived from a substituted or unsubstituted arylsulfonate, lower alkanesulfonate, halogeno-lower alkanesulfonate or diarylphosphoric acid ester or a halide, i.e., an ester with a hydrogen halide, of the alcohol represented by the formula (II). The substituted or unsubstituted arylsulfonate includes, for example, a benzenesulfonate, a p-toluenesulfonate, a p-nitrobenzenesulfonate, a p-bromobenzenesulfonate, etc. The lower alkanesulfonate includes, for example, a methanesulfonate, an ethanesulfonate, etc. The halogeno-lower alkanesulfonate includes, for example, a trifluoromethanesulfonate, etc. The diarylphosphoric acid ester includes, for example, a diphenylphosphoric acid ester, etc. The halide includes, for example, a chloride, a bromide, an iodide, etc. Of these reactive esters of an alcohol, preferred examples are a p-toluenesulfonate, a methanesulfonate and a diphenylphosphoric acid ester.

Further, in the substituted or unsubstituted lower alkylsulfinyl group, the lower alkyl group preferably includes a straight chain or branched chain alkyl group having 1 to 4 carbon atoms. The substituent for the substituted lower alkyl group can include a hydroxyl group, a lower alkoxy group having 1 to 4 carbon atoms, a lower alkoxycarbonyloxy group having 2 to 5 carbon atoms, a lower alkanoyloxy group having 2 to 5 carbon atoms, an amino group, a mono- or di-lower alkylamino group, a lower alkanoylamino group having 2 to 5 carbon atoms, a lower alkoxycarbonylamino group having 2 to 5 carbon atoms, an aralkyloxycarbonyloxy group, an aralkyloxycarbonylamino group, etc.

The protecting group for a carboxyl group as represented by $R_9$ corresponds to the protecting group as represented by $R_3$, and the same preferred groups as enumerated for $R_3$ can also be applied to $R_9$.

Examples for the inert solvent which can be used in the above-described reaction are dioxane, tetrahydrofuran, dimethylformamide, dimethyl sulfoxide, acetonitrile, hexamethylphosphoramide and mixtures thereof, with acetonitrile and dimethylformamide being preferred.

The base also used in the reaction includes various organic or inorganic bases, such as sodium carbonate, potassium carbonate, sodium hydride, potassium hydride, potassium t-butoxide, pyridine, various lutidines, 4-dimethylaminopyridine, triethylamine, diisopropylethylamine and the like, with the organic bases, e.g., diisopropylethylamine, etc., being preferred.

The amount of the base to be used should be enough for the reaction to sufficiently proceed and usually ranges from 1 to 2 equivalents per mole of the mercaptan derivative of the formula (III).

The mercaptan derivative (III) is used in an amount enough for the reaction to sufficiently proceed. It may be used in a large excess but usually in an amount of from 1 to 2 equivalents based on the compound of the formula (II).

The reaction can be carried out at a temperature ranging from about −78° C. to 60° C., preferably from −40° C. to 40° C.

After completion of the reaction, the reaction product can be isolated by usual organochemical means.

Then, the thus obtained compound represented by the formula (IV) can be subjected, if necessary, to a reaction for removal of the hydroxyl-protecting group when $R_1$ is a protected hydroxyl group, a reaction for removal of the amino-protecting group, a reaction for removal of the carboxyl-protecting group $R_9$, a reaction for removal of the protecting group on Y', or an appropriate combination thereof, thereby to obtain the β-lactam compound represented by the formula (I).

The reactions for removal of the protecting groups can be carried out by generally known methods selected depending on the type of the protecting groups. For example, those compounds of the formula (IV) wherein the hydroxyl-protecting group and/or the amino-protecting group in $R_2$ is/are a halogenoalkoxycarbonyl group(s) or an aralkyloxycarbonyl group(s), and those compounds wherein the carboxyl-protecting group is a halogenoalkyl group, an aralkyl group or a benzhydryl group can be subjected to an appropriate reduction reaction to remove these protecting groups. Such reduction is preferably carried out by using an organic solvent, such as acetic acid, tetrahydrofuran, methanol, etc., and zinc in case when the protecting group to be removed is a halogenoalkoxycarbonyl group or a halogenoalkyl group, or by catalytic reduction using a catalyst, such as platinum or palladium-on-carbon, in case when the protecting group to be removed is an aralkyloxycarbonyl group, an aralkyl group or a benzhydryl group. Solvents to be used in the catalytic reduction suitably include organic solvents, such as lower alcohols, e.g., methanol, ethanol, etc.; ethers, e.g., tetrahydrofuran, dioxane, etc.; and acetic acid, or mixed solvents of these organic solvents and water or buffer solutions, such as phosphoric acid, morpholinopropanesulfonic acid, etc. The reaction can be conducted at a temperature of from about 0° C. to 100° C., preferably 0° C. to 40° C., in a hydrogen atmosphere under atmospheric pressure or under pressurized conditions.

In particular, when the protecting group to be removed is an o-nitrobenzyl group or an o-nitrobenzyloxycarbonyl group, these groups can also be removed by photo reaction.

In the compounds according to the present invention, the 5- and 6-positions of the compounds of the above-described formula (I), the 8-position of the compounds represented by the formula (V):

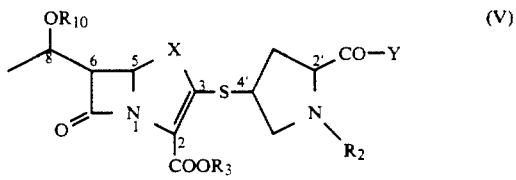

wherein $R_2$, $R_3$, X and Y are as defined above, and $R_{10}$ represents a hydrogen atom or a protecting group for a hydroxyl group, the 4-position of the compounds represented by the formula (VI):

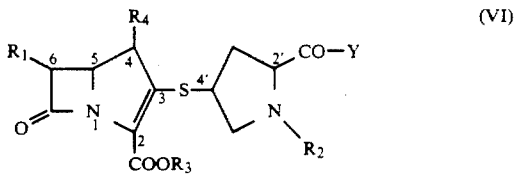

wherein $R_1$, $R_2$, $R_3$, $R_4$ and Y are as defined above, and $R_4$ is an alkyl group, and the 2'- and 4'-positions in the 2-side chain of the compounds of the formulae (I), (V) and (VI) are all asymmetric carbons to form isomers. Therefore, the compounds represented by these formulae include optical isomers and steric isomers ascribed to these asymmetric carbon atoms. Although all of these isomers are represented by a respective single formula for the sake of convenience, the scope of the present invention is not limited by such a single formula.

However, preferred isomers can include those having an R-configuration at the 5-positioned carbon atom, similarly to thienamycin, i.e., the (5R,6S)- or (5R,6R)-compounds. With respect to the 8-positioned carbon atom of the formula (V), those having an R-configuration are preferred. Further, with respect to the 4-position of the formula (VI), those wherein the lower alkyl group as represented by $R_4$ is in a R-configuration (i.e., (4R)-compounds) are preferred.

In addition, the 2'-substituted pyrrolidin-4'-ylthio group forms four isomers, of which the (2'S,4'S)- and (2'R,4'R)-compounds are preferred.

Particularly preferred compounds include those compounds of the formula (I) having a (5R,6S,2'S,4'S)-configuration, those compounds of the formula (V) having a (5R,6S,βR,2'S,4'S)-configuration, and those compounds of the formula (VI), wherein $R_1$ is a 1-hydroxyethyl type substituent and $R_4$ is a lower alkyl group, having a (4R,5R,6S,βR,2'S,4'S)-configuration.

The isomers having the above-described steric configurations can be obtained by using the starting compounds of the formula (II) and/or (III) having the corresponding configurations.

The starting compounds (II) can be prepared according to various known methods. For example, the compounds represented by the formula (VII);

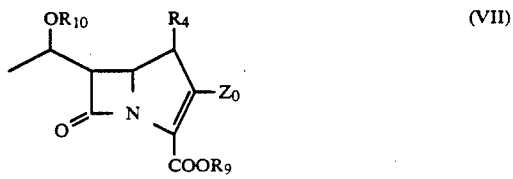

wherein $R_4$, $R_9$ and $R_{10}$ are as defined above, and $Z_0$ represents a reactive ester group of an alcohol, and also wherein $R_4$ is a hydrogen atom are known per se in (1) Japanese Patent Application OPI (Open to Public Inspection) No. 27169/80, (2) J. Am. Chem. Soc., Vol. 103, 6765–6767 (1981) and (3) J. Chem. Soc., Perkin I, 964–968 (1981), etc., and the compounds (VII) can be obtained according to the methods described in the above-described literatures (1) to (3).

Further, the compounds (VII) can also be synthesized in accordance with the methods described in the above-described literatures (1) to (3), etc. starting with compounds represented by the formula (a):

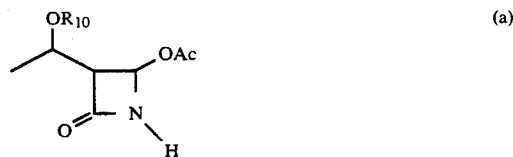

wherein $R_{10}$ is as defined above, and Ac represents an acetyl group,
which can be obtained by the method described in Tetrahedron Letters, 2293–2296 (1982) or the method described in EPC Publication No. 70204.

Furthermore, the compounds (VII) can also be obtained by subjecting a compound represented by the formula (b):

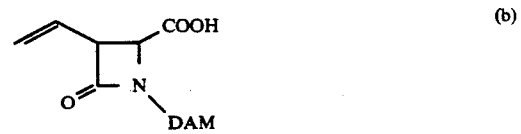

wherein DAM represents a di-p-anisylmethyl group, which is obtained by the method disclosed in EPC Publication No. 70204 to a carbon-increasing reaction such as Arndt-Einstert reaction and the like and then to an oxymercuration reaction and the like according to the method of EPC Publication No. 70204, thereby converting the ethenyl group into a 1-hydroxyethyl group, subjecting the resulting product, if necessary, to an appropriate combination of a reaction for protecting or deprotecting the carboxyl group and a reaction for protecting the hydroxyl group to obtain a compound represented by the formula (c):

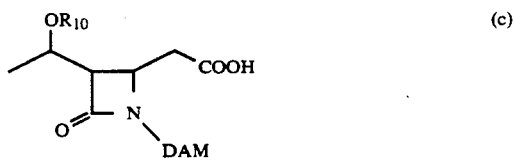

wherein $R_{10}$ and DAM are as defined above, and then obtaining the compound (VII) from the compound (c) in accordance with the method described in Japanese Patent Application OPI No. 167964/82.

The DAM group on the nitrogen atom in the compound (c) can be removed by reacting with ceric ammonium nitrate in an inert solvent such as acetonitrile-water at 10° to 30° C. In this case, this reaction may be combined with a reaction for protecting or deprotecting the carboxyl group and/or a reaction for protecting the hydroxyl group, if necessary.

Further, the compound of the formula (VII) wherein $R_4$ is an alkyl group can be prepared by, for example, the known method as disclosed in Japanese Patent Application OPI No. 26887/83 or analogous methods thereof.

Compounds of the formula (VIII):

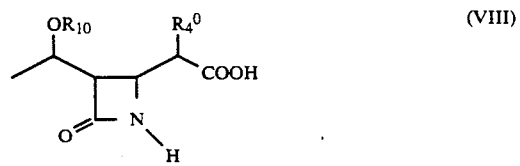

wherein $R_{10}$ is as defined above and $R_4^0$ an alkyl group having 1 to 3 carbon atoms, which can be used as a starting material for preparing the compound (VII) wherein $R_4$ is an alkyl group, can be produced, for example, according to the following reaction scheme:

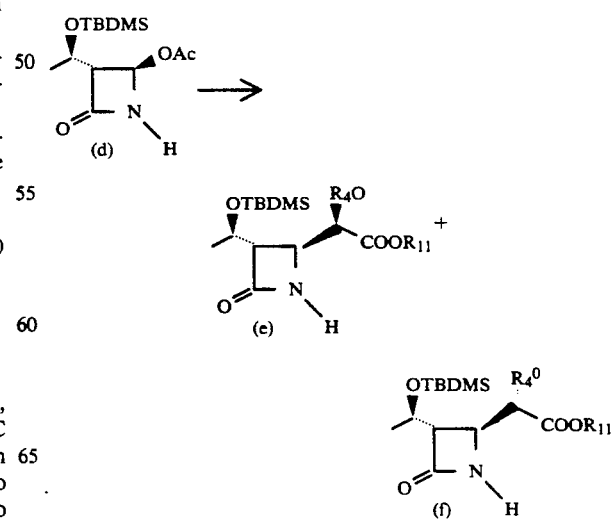

wherein $R_4^0$ is as defined above; $R_{11}$ represents a protecting group for a carboxyl group; and TBDMS represents a t-butyldimethylsilyl group.

The compounds of the formulae (e) and (f) can be obtained as an isomeric mixture by a method described in Japanese Patent Application OPI No. 73656/80 which comprises reacting (3R,4R)-4-acetoxy-3-[(R)-1-(t-butyldimethylsilyloxy)ethyl]-2-azetidinone of the formula (d) disclosed in Chem. Pharm. Bull., Vol. 29, 2899-2909 (1981) with a halogenofatty acid ester represented by the formula:

$$R_4^0 CHX'—COOR_{11}$$

wherein $R_4^0$ and $R_{11}$ are as defined above, and $X'$ represents a halogen atom, in a solvent, such as an ether (e.g., tetrahydrofuran, dioxane, diethyl ether, etc.), an aromatic hydrocarbon (e.g., benzene, toluene, etc.), and the like, or a mixed solvent of these solvents and hexane in the presence of diethylaluminium chloride and zinc.

Separation and purification of the isomers (e) and (f) can be carried out by silica gel column chromatography.

The compounds (e) and (f) can be led to the compound (VIII) by appropriately combining reactions for protecting or deprotecting the hydroxyl group, the carboxyl group or the nitrogen atom.

One example for the production of the starting compound (VII) will be illustrated in the following reaction scheme:

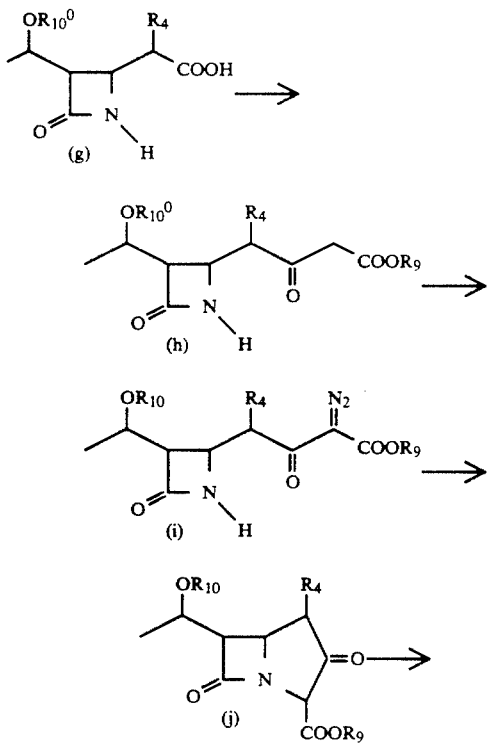

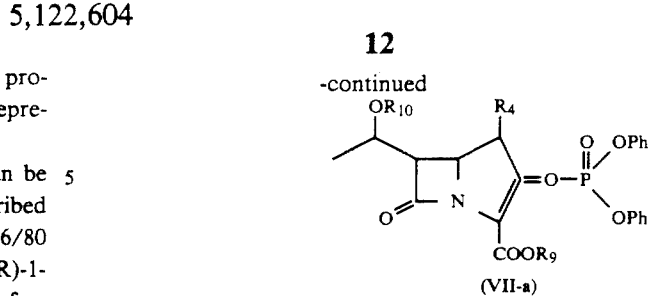

wherein $R_4$, $R_9$ and $R_{10}$ are as defined above $R_{10}$ represents a protecting group for a hydroxyl group; and Ph represents a phenyl group.

More specifically, the compound (g) obtainable by the aforesaid methods can be led to the compound (h) through the reaction described in Japanese Patent Application OPI No. 167964/82 or Heterocycles, Vol. 14, 1305-1306 (1980).

The compound (h) is then reacted with a diazonizing agent, e.g., carboxybenzenesulfonazide, in the presence of a base to obtain the compound (i) as disclosed in Tetrahedron Letters, 31-34 (1980).

The compound (i) is then subjected to cyclization in the presence of a metal salt catalyst, e.g., dirhodium tetrakisacetate, or by photo reaction to obtain the compound (j).

Finally, the compound (j) is reacted with diphenylphosphoryl chloride in an inert solvent in the presence of a base such as diisopropyl ethyl amine, 4-dimethylaminopyridine, etc. to obtain the compound of the formula (VII-a).

In general, the starting compound (VII-a) as prepared from the compound (j) is subsequently subjected to the reaction with various mercaptans without being isolated to produce carbapenem derivatives, but the starting compound (VII-a) may be once isolated from the reaction mixture and then reacted with the mercaptan derivative (III) to obtain the desired compound of the formula (IV).

Optically active reactive esters, for example, the compound (VII-a), can be obtained in the same manner as described above but starting with the β-lactam derivative (g) having the corresponding steric configuration.

Further, of the above-described compounds of the formula (II), the compounds, for example, of the compound (IX):

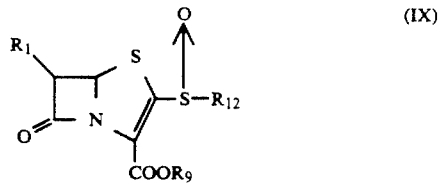

wherein $R_1$ and $R_9$ are as defined above, and $R_{12}$ represents a substituted or unsubstituted lower alkyl group, can be prepared by subjecting a compound of the formula (X):

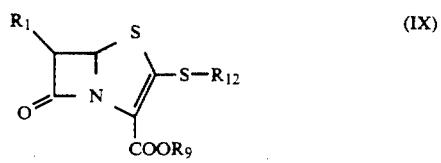

wherein $R_1$, $R_9$ and $R_{12}$ are as defined above, to S-oxidation using a mild oxidizing agent. The mild oxidizing agent includes perbenzoic acid, m-chloroperbenzoic acid, hydrogen peroxide, selenium dioxide, sodium m-periodate and the like, with substituted perbenzoic acids, e.g., m-chloroperbenzoic acid, etc., being preferred.

The starting compound represented by the formula (X) can be prepared by various methods already reported, for example, the methods as disclosed in Japanese Patent Application OPI Nos. 9034/80, 105686/80 and 81591/81.

On the other hand, the starting mercaptan derivative of the formula (III) can be prepared by various methods. For example, mercaptan derivatives (IIIa), (IIIb), and (IIIc) having a 2'S-configuration can be obtained from trans-4-hydroxy-L-proline (i) in accordance with the reaction scheme shown below:

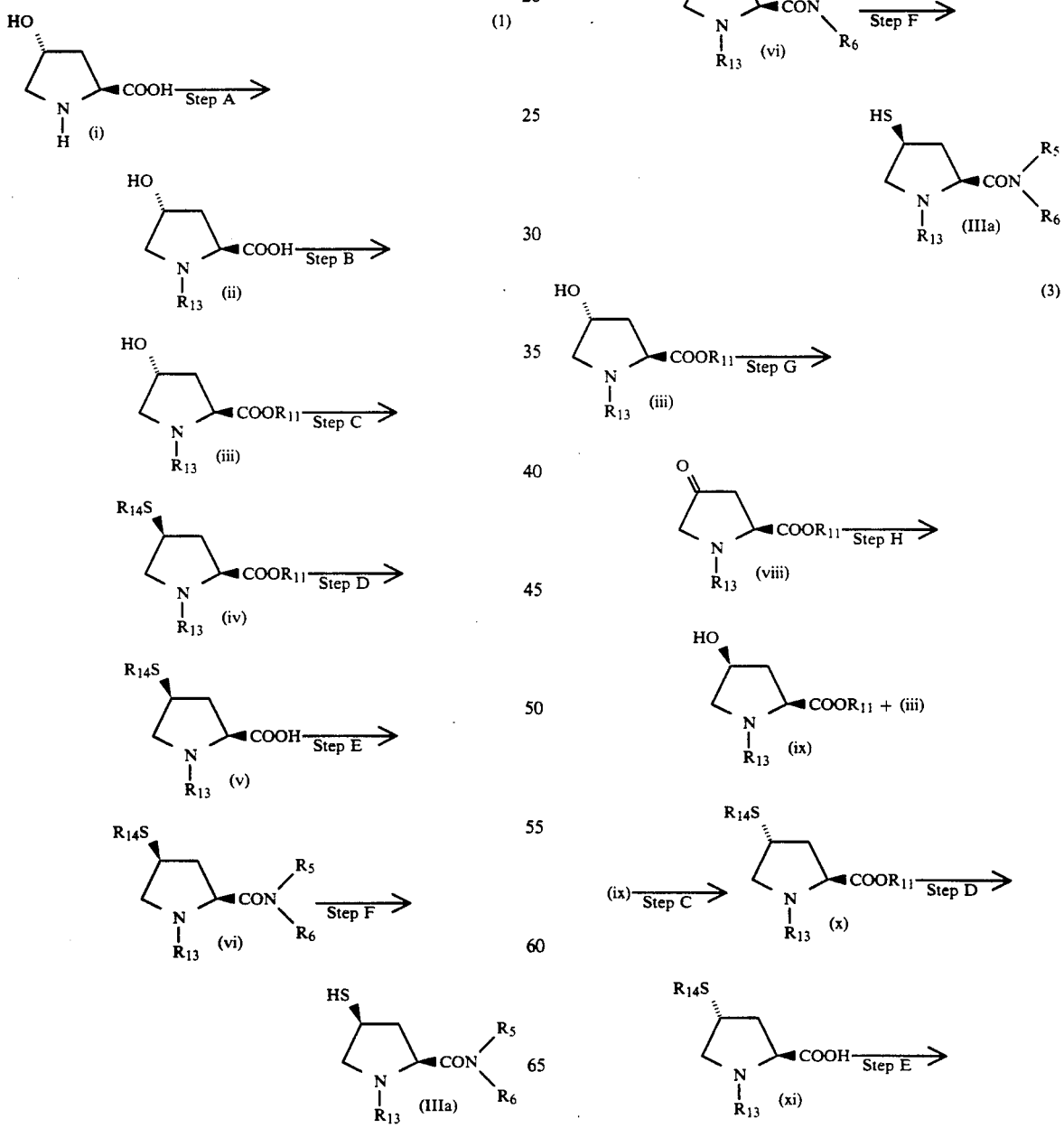

-continued

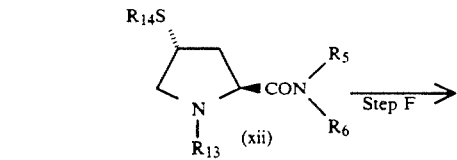

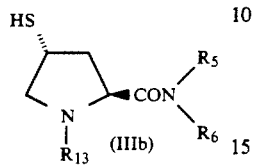   (4)

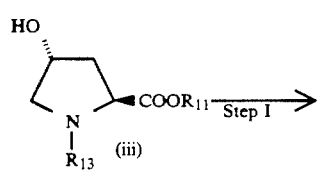

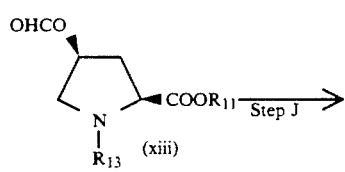

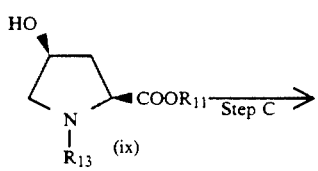

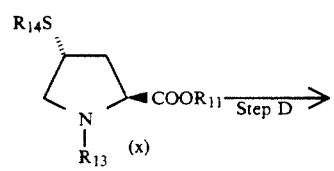

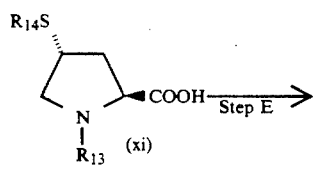

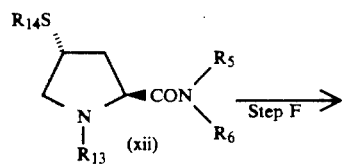

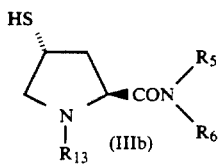

-continued

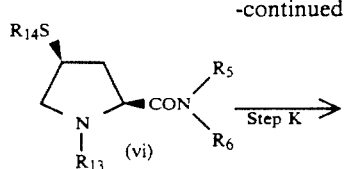   (5)

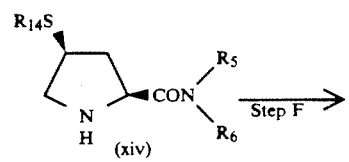

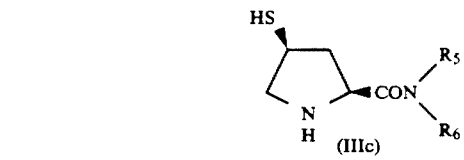

In the above formulae, $R_5$, $R_6$ and $R_{11}$ are as defined above; $R_{13}$ represents a protecting group for an amino group; and $R_{14}$ represents a protecting group for a thiol group.

Step A

The reaction can easily be accomplished by various known methods generally employed for protecting an amino group of amino acids, for example, a method comprising reacting with an arylmethyloxycarbonyl chloride, etc. in the presence of a base, a method comprising using an S-acyl-4,6-dimethyl-2-mercaptopyrimidine, etc., and the like.

Step B

The reaction can be carried out by various methods for obtaining esters from carboxylic acids, for example, by reacting the carboxylic acid (ii) with various alkyl halides or aralkyl halides, etc. in the presence of a base.

Step C

The reaction can be accomplished by various known methods for converting a hydroxyl group into a protected thiol group, for example, by a method comprising converting the carboxylic acid ester (iii) into an active ester of a hydroxyl group and then reacting with various thionizing reagents, e.g., thioacetic acid, thiobenzoic acid, tritylmercaptan, etc., in the presence of a base.

This step may also be conducted by reacting the alcohol derivative with a thionizing reagent, e.g., thioacetic acid, etc., in an inert solvent, e.g., tetrahydrofuran, etc., in the presence of triphenylphosphine and diethyl azodicarboxylate.

Step D

This step can be carried out by various known methods for converting an ester group into a carboxyl group, for example, alkali-hydrolysis, a method of using trifluoroacetric acid, hydrobromic acid, etc., or a reductive method of using zinc.

Step E

The reaction can be achieved by various known methods for converting a carboxyl group to an amido group, for example, by a method comprising reacting with a halogenating agent, an acylating agent, etc. to form an active ester derivative and then treating the resulting ester with an amine represented by the formula:

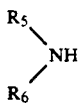

wherein $R_5$ and $R_6$ are as defined above.

Step F

The thiol-protecting group can be removed by various known methods for deprotection. For example, an acyl group as the thiol-protecting group can be removed by alkali-hydrolysis and the like.

Step G

The reaction can be accomplished by various known oxidation methods for converting a hydroxyl group into a carbonyl group, for example, an oxidation reaction using chromic acid-sulfuric acid, etc. in acetone.

Step H

The step can be attained by various known reduction reactions for converting a carbonyl group to a hydroxyl group. For example, treatment with sodium borohydride, etc. gives a mixture of the compound (iii) and the compound (ix) having different steric configurations at the hydroxyl group. The production proportion of (iii) and (ix) varies depending on reaction conditions, but each compound can be isolated as a single compound by purification procedures, such as recrystallization, chromatography and the like.

Isomerization of the 4-hydroxyl group can be accomplished through the above-described steps G and H, and may also be achieved through hereinafter described steps I and J.

Steps I & J

The alcohol derivative is reacted with formic acid in an inert solvent, e.g., tetrahydrofuran, etc., in the presence of triphenylphosphine and diethyl azodicarboxylate to form a formyloxy derivative (xiii), which is then subjected to alkali-hydrolysis, etc. to remove the formyl group.

Step K

This step can be conducted by commonly employed various known methods for deprotecting amino groups, for example, a method of using an acid, e.g., trifluoroacetic acid, hydrobromic acid, etc., a reducing method of using zinc, lithium-liquid ammonia, etc., or a catalytically reducing method.

The starting mercaptan derivatives (III) to be used for the production of the β-lactam compounds (I) wherein Y is a protected or unprotected hydroxyl group or an alkoxy group having 1 to 3 carbon atoms can be obtained by subjecting the compound (iv) or (x) to Step F.

The 2'R-mercaptan (III) can be prepared by using cis-4-hydroxy-D-proline as a starting compound in accordance with the above-described method for producing 2'S-compounds, i.e., by combining various reactions described in the production of the 2'S-compounds.

Of the novel β-lactam compounds represented by the formula (I) according to the present invention, those compounds in which $R_1$, $R_2$ and $R_3$ are all hydrogen atoms exhibit excellent antimicrobial activity against a wide variety of disease-causing bacteria including Gram positive bacteria, such as *Staphylococcus aureaus, Staphylococcus epidermidis, Streptococcus pyogenes, Streptococcus faecalis*, etc., and Gram negative bacteria, such as *Escherichia coli, Proteus mirabilis, Serratia marcescens, Pseudomonas aeruginosa*, etc., and are useful, therefore, as antimicrobial agents. Further, these compounds have a characteristic of exhibiting excellent antimicrobial activity against β-lactamase-producing strains. Other compounds according to the present invention are important intermediates for synthesizing the above-mentioned compounds having antimicrobial activity.

In addition, the compounds according to the present invention are also characterized in general by their high physiochemical stability and excellent water solubility, although varying depending on the respective compound.

The compounds of the present invention can be used as antimicrobial agents for treating bacteria-caused infectious diseases in the form of oral preparations, such as tablets, capsules, powders, syrups, etc. or non-oral preparations, such as intravenous injections, intramuscular injections, rectal preparations, etc.

The dosage of the antimicrobial agent varies depending upon the symptoms, ages, body weights, dosage forms, times of doses and the like, but usually ranges from about 100 mg to 3,000 mg per day in a single dose or several divided doses for adults. The above dose level can be increased or decreased according to necessity.

Besides, the antimicrobial agent of the present invention can be administered, if necessary, in combination with dehydrodipeptidase-inhibitors, e.g., sodium Z-7-(L-amino-2-carboxyethylthio)-2-(2,2-dimethylcyclopropanecarboxyamido)-2-heptenoate, etc. (a series of compounds disclosed in Japanese Patent Application OPI No. 81518/81).

The present invention will now be illustrated in greater detail with reference to the following Reference Examples and Examples but it should be understood that these examples are given only for illustrative purposes and are not limiting the present invention.

In Reference Examples and Examples, the following abbreviations are used:

DAM: Di-(p-anisyl)methyl group
TBDMS t-Butyldimethylsilyl group
PNZ: p-Nitrobenzyloxycarbonyl group
PMZ: p-Methoxybenzyloxycarbonyl group
PMB: p-Methoxybenzyl group
PNB: p-Nitrobenzyl group
Ph: Phenyl group
Ac: Acetyl group
Ms: Methanesulfonyl group
tBu: t-Butyl group
Me: Methyl group
Et: Ethyl group

REFERENCE EXAMPLE 1-1

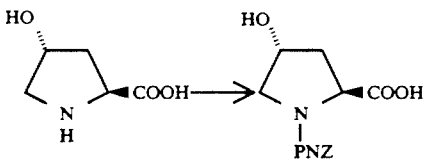

6.55 g of trans-4-hydroxy-L-proline and 7.5 ml of triethylamine were dissolved in 15 ml of water, and a solution of 15.95 g of S-p-nitrobenzyloxycarbonyl-4,6-dimethyl-2-mercaptopyrimidine in 35 ml of dioxane was added thereto dropwise. The resulting mixture was stirred at room temperature for 1.5 hours and allowed to stand overnight. To the reaction mixture was added 30 ml of a 2N sodium hydroxide aqueous solution under ice-cooling, and the resulting mixture was extracted with diethyl ether. The ethereal layer was washed with 20 ml of a 1N sodium hydroxide aqueous solution and combined with the alkaline aqueous layer. The combined mixture was made acidic with 100 ml of a 2N hydrochloric acid aqueous solution and extracted with ethyl acetate. The ethyl acetate layer was washed with a 2N aqueous solution of hydrochloric acid, dried over sodium sulfate and distilled off to remove the solvent. The resulting crude crystals were washed with warm ethyl acetate to obtain trans-1-(p-nitrobenzyloxycarbonyl)-4-hydroxy-L-proline.

Melting Point: 134.3°-135.5° C.

$IR_{max}^{Nujol}$ (cm$^{-1}$): 3300 (br.), 1738, 1660, 1605, 1520, 1340, 1205, 1172, 1070, 965

REFERENCE EXAMPLE 1-2

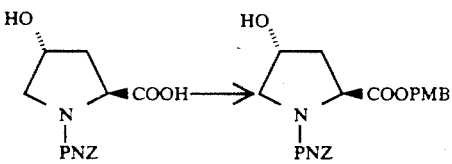

15.0 g of trans-1-(p-nitrobenzyloxycarbonyl)-4-hydroxy-L-proline and 13.5 ml of triethylamine were dissolved in 150 ml of dried dimethylformamide, and 12.66 ml of p-methoxybenzyl chloride was added dropwise to the solution under a nitrogen stream, followed by stirring at 70° C. for 10 hours. The reaction mixture was diluted with 500 ml of ethyl acetate, washed with water, dried over sodium sulfate and distilled off to remove the solvent. Recrystallization of the residue from diethyl ether gave trans-1-(p-nitrobenzyloxycarbonyl)-4-hydroxy-L-proline p-methoxybenzyl ester.

Melting Point: 83°-85° C.

$IR_{max}^{neat}$ (cm$^{-1}$): 3430, 1735, 1705, 1510, 1340, 1245, 1160

REFERENCE EXAMPLE 1-3

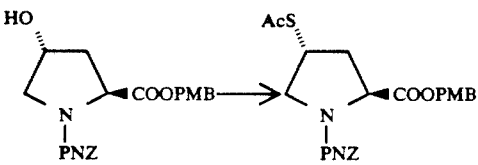

8.6 g of trans-1-(p-nitrobenzyloxycarbonyl)-4-hydroxy-L-proline-p-methoxybenzyl ester and 7.86 g of triphenylphosphine were dissolved in 20 ml of dried tetrahydrofuran. To the resulting solution was added dropwise a solution of 5.22 g of diethyl azodicarboxylate in 5 ml of dried tetrahydrofuran under ice-cooling in a nitrogen stream, followed by stirring for 30 minutes at that temperature. Thereafter, 2.28 g of thioacetic acid was added thereto dropwise, and the mixture was stirred for 1 hour under ice-cooling and then at room temperature for 3 hours, followed by concentration. The residue was purified by silica gel column chromatography to obtain cis-1-(p-nitrobenzyloxycarbonyl)-4-acetylthio-L-proline p-methoxybenzyl ester.

$IR_{max}^{neat}$ (cm$^{-1}$) 1740 (sh.), 1715, 1520, 1405, 1348, 1120

NMR δ (CDCl$_3$): 2.31 (3H, s), 3.79 (3H, s), 5.10 (2H, s), 5.24 (2H, s), 7.49 (2H, d, J=9.0Hz), 8.18 (2H, d, J=9.0Hz)ppm

REFERENCE EXAMPLE 1-4

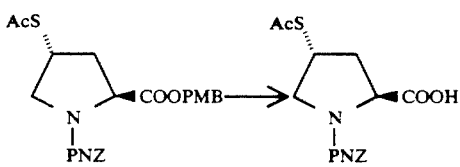

9.76 g of cis-1-(p-nitrobenzyloxycarbonyl)-4-acetylthio-L-proline p-methoxybenzyl ester and 4.32 g of anisole were stirred together with 35 ml of trifluoroacetic acid at room temperature for 30 minutes. The reaction mixture was concentrated under reduced pressure, and the residue was purified by silica gel column chromatography to obtain cis-1-(p-nitrobenzyloxycarbonyl)-4-acetylthio-L-proline.

Melting Point: 107°-109° C.

$IR_{max}^{Nujol}$ (cm$^{-1}$): 1725, 1685, 1660 (sh.), 1340, 1180, 1110

REFERENCE EXAMPLE 1-5

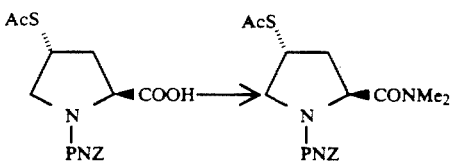

180 mg of cis-1-(p-nitrobenzyloxycarbonyl)-4-acetylthio-L-proline was dissolved in 2 ml of dried tetrahydrofuran, and 48 mg of dimethylamine hydrochloride, 78 mg of N,N-dimethylaminopyridine and 152 mg of dicyclohexylcarbodiimide were successively added thereto, followed by stirring overnight. After any insoluble matter was removed by filtration, the filtrate was diluted with ethyl acetate, washed successively with dilute hydrochloric acid and water, dried over sodium sulfate and distilled off to remove the solvent. The residue was purified by silica gel chromatography to obtain (2S,4S)-cis-1-(p-nitrobenzyloxycarbonyl)-2-dimethylcarbamoyl-4-acetylthiopyrrolidine.

The above prepared compound could also be obtained by the following method:

200 mg of the same starting carboxylic acid was dissolved in 1.8 ml of dried methylene chloride, and one drop of dimethylformamide was added thereto. 0.12 ml of oxalyl chloride was then added dropwise thereto under ice-cooling, followed by stirring at room temperature for 1 hour. The solvent was removed by distillation, and the residue was thoroughly dried in vacuo and dissolved in 1 ml of dried tetrahydrofuran. Under ice-cooling, 1.2 ml of a 1M solution of dimethylamine in tetrahydrofuran was added to the reaction mixture, followed by stirring at that temperature for 15 minutes. To the reaction mixture was added ice-water, and the mixture was extracted with ethyl acetate. The organic layer was washed successively with dilute hydrochloric acid and water, dried over sodium sulfate and distilled off to remove the solvent.

IR$_{max}^{neat}$(cm$^{-1}$): 1705, 1650, 1515, 1400, 1340, 1105

NMR δ (CDCl$_3$) 2.32 (3H, s), 2.97 (3H, s), 3.11 (3H, s), 5.21 (2H, s), 8.18 (2H, d, J=8.5Hz) ppm

[α]$_D^{30}$+5.21° (c=0.379, acetone)

REFERENCE EXAMPLE 1-6

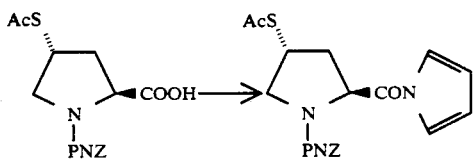

277 mg of (2S,4S)-1-p-nitrobenzyloxycarbonyl-2-hydroxycarbonyl-4-acetylthiopyridine was dissolved in 1.5 ml of dried methylene chloride, and 0.15 ml of oxalyl chloride and a catalytic amount of dimethylformamide were added thereto, followed by stirring at room temperature for 1.5 hours. The reaction mixture was distilled off to remove the solvent, and dried benzene was added to the residue. The benzene was then distilled off to remove any remaining oxalyl chloride. Separately, 51 mg of pyrrole was dissolved in 2 ml of dried tetrahydrofuran, and 0.47 ml of a 1.60 mmol/ml solution of n-butyl lithium in hexane was added thereto in a nitrogen stream under ice-cooling, followed by stirring at that temperature for 40 minutes. The resulting mixture was then added in a nitrogen stream under ice-cooling to a solution of the above-described reaction residue dissolved in 2 ml of dried tetrahydrofuran, followed by stirring for 10 minutes. The resulting reaction mixture was diluted with methylene chloride, washed with water, dried over sodium sulfate and distilled off to remove the solvent. The residue was purified by silica gel thin layer chromatography to obtain (2S, 4S)-1-p-nitrobenzyloxycarbonyl-2-(1-pyrrolyl)carbonyl-4-acetylthiopyrrolidine.

IR $v_{max}^{CHCl_3}$ (cm$^{-1}$): 1710, 1525, 1345, 1278, 1120

NMR δ (CDCl$_3$) 2.33 (3H, s), 5.23 (2H, s), 6.35 (2H, d, J=2Hz), 7.51 (2H, d, J=9Hz) ppm

REFERENCE EXAMPLE 1-7

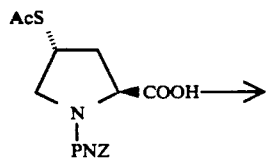

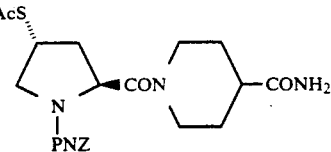

368 mg of (2S,4S)-1-p-nitrobenzyloxycarbonyl-2-hydroxycarbonyl-4-acetylthiopyrrolidine was dissolved in 3 ml of dried methylene chloride, and 0.3 ml of oxalyl chloride and a catalytic amount of dimethylformamide were added thereto, followed by stirring at room temperature for 1.5 hours. The reaction mixture was distilled off to remove the solvent, and to the residue was added dried benzene. The benzene was then distilled off to remove any remaining oxalyl chloride. Separately, 128 mg of 4-carbamoylpiperidine was dissolved in 3 ml of dried tetrahydrofuran, and 0.25 ml of bistrimethylsilylacetamide was added to the solution, followed by stirring for 3 hours in a nitrogen stream. Then, 101 mg of triethylamine was added thereto, and to the resulting mixture was added in a nitrogen stream under ice-cooling a solution of the above-obtained reaction residue dissolved in 3 ml of dried tetrahydrofuran, followed by stirring for 15 minutes under ice-cooling. Methylene chloride was added to the resulting reaction mixture. The mixture was washed successively with a sodium chloride aqueous solution, dilute hydrochloric acid, a sodium chloride aqueous solution, a sodium bicarbonate aqueous solution and a sodium chloride aqueous solution, dried over sodium sulfate and distilled off to remove the solvent. The residue was purified by silica gel thin layer chromatography to obtain (2S,4S)-1-p-nitrobenzyloxycarbonyl-2-(4-carbamoylpiperidinyl)-carbonyl-4-acetylthiopyrrolidine.

IR $v_{max}^{CHCl_3}$ (cm$^{-1}$): 3440, 1695, 1655, 1525, 1350, 1120

NMR δ (CDCl$_3$) 2.35 (3H, s), 5.21 (2H, s), 5.93 (2H, s), 7.52 (2H, d, J=9Hz), 8.22 (2H, d, J=9Hz) ppm

REFERENCE EXAMPLE 1-8

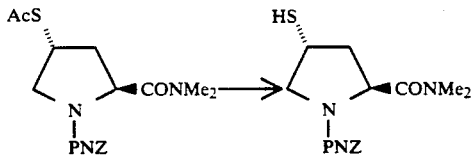

40 mg of (2S,4S)-1-(p-nitrobenzyloxycarbonyl)-2-dimethylcarbamoyl-4-acetylthiopyrrolidine was dissolved in 4 ml of methanol, and 0.1 ml of a 1N sodium hydroxide aqueous solution was added thereto, followed by stirring at room temperature for 15 minutes. 0.11 ml of a 1N hydrochloric acid aqueous solution was then added thereto, followed by concentration under reduced pressure. The concentrate was diluted with ethyl acetate, washed with water, dried over sodium sulfate and distilled off to remove the solvent to obtain (2S,4S)-1-(p-nitrobenzyloxycarbonyl)-2-dimethylcarbamoyl-4-mercaptopyrrolidine.

IR$_{max}^{neat}$(cm$^{-1}$): 1705, 1650, 1515, 1400, 1340, 1165, 1105

NMR δ (CDCl$_3$) 1.90 (1H, d, J=8Hz), 2.97 (3H, s), 3.08 (3H, s), 5.19 (2H, s), 7.48 (2H, d, J=9Hz), 8.15 (2H, d, J=9Hz) ppm In the same manner as described in Reference Example 1-5 but using the corresponding amines, the following thioacetate derivatives shown in Table 1 were obtained.

TABLE 1

[Structure: pyrrolidine with AcS at one position, COY at another, and N-PNZ]

| Reference Example No. | Y | Spectral Data |
|---|---|---|
| 1-9 | $-N(C_2H_5)_2$ | $IR\nu_{max}^{neat}$ (cm$^{-1}$): 1700, 1660(sh), 1520, 1405, 1345, 1115 |
| 1-10 | $-NH-CH(CH_3)_2$ | $IR\nu_{max}^{neat}$ (cm$^{-1}$): 3300, 1695, 1655, 1525, 1415, 1348, 1265, 1105<br>NMRδ (CDCl$_3$): 1.13(3H, d, J=6Hz), 1.15(3H, d, J=6Hz), 2.34(3H, s), 5.26(2H, s), 7.53(2H, d, J=9Hz), 8.21(2H, d, J=9Hz) |
| 1-11 | $-NH-CH_2CH=CH_2$ | $IR\nu_{max}^{neat}$ (cm$^{-1}$): 1700, 1652, 1518, 1400, 1342, 1110 |
| 1-12 | $-NH-CH_2CONH_2$ | $IR\nu_{max}^{neat}$ (cm$^{-1}$): 3320, 1680, 1520, 1430, 1405, 1345, 1120<br>NMRδ (CDCl$_3$): 2.32(3H, s), 5.17(2H, br, s), 7.43(2H, d, J=9Hz) 8.10(2H, d, J=9Hz)<br>m.p. 163-167° C. |
| 1-13 | $-N(CH_3)CH_2CH_2OH$ | $IR\nu_{max}^{neat}$ (cm$^{-1}$): 3400(br), 1685, 1640(sh), 1517, 1403, 1342, 1212, 1115<br>NMRδ (CDCl$_3$): 2.33(3H, s), 2.97(3H, s), 5.20(2H, s), 7.49(2H, d, J=9Hz), 8.19(2H, d, J=9Hz) |
| 1-14 | $-N(CH_3)CH_2CH_2N(CH_3)_2$ | $IR\nu_{max}^{neat}$ (cm$^{-1}$): 1710, 1660, 1525, 1400, 1345, 1255, 1110<br>NMRδ (CDCl$_3$): 2.28(3H, s), 2.30(6H, s), 2.50(3H, s), 5.17(2H, s), 7.42(2H, d, J=8.5Hz), 8.13(2H, d, J=8.5Hz) |
| 1-15 | $-N(CH_3)CH_2Ph$ | $IR\nu_{max}^{neat}$ (cm$^{-1}$): 3320, 1700, 1650, 1520, 1405, 1345, 1220, 1110<br>NMRδ (CDCl$_3$): 2.33(3H, s), 2.93(3H, s), 5.23(2H, s), 7.27(5H, br, s) |
| 1-16 | piperidin-1-yl | $IR\nu_{max}^{neat}$ (cm$^{-1}$): 1710, 1650, 1525, 1425, 1345, 1245, 1025, 962<br>NMRδ (CDCl$_3$): 1.58(6H, m), 2.32(3H, s), 5.22(2H, s) |
| 1-17 | morpholin-4-yl | $IR\nu_{max}^{neat}$ (cm$^{-1}$): 1710, 1655, 1520, 1430, 1400, 1345, 1115<br>NMRδ (CDCl$_3$): 2.31(3H, s), 5.20(2H, s), 7.47(2H, d, J=9Hz), 8.18(2H, d, J=9Hz) |
| 1-18 | 4-methylpiperazin-1-yl | $IR\nu_{max}^{neat}$ (cm$^{-1}$): 1700, 1650(sh), 1520, 1435, 1340, 1290, 1235, 1110, 1000 |
| 1-19 | $-N(CH_3)(n\text{-}C_4H_9)$ | $IR\nu_{max}^{neat}$ (cm$^{-1}$): 1710, 1650, 1520, 1350, 1110<br>NMRδ (CDCl$_3$): 2.33(3H, s), 4.68(1H, t, J=8Hz), 5.19(2H, s), 8.18(2H, d, J=8Hz) |
| 1-20 | $-NH-CH_2$-(2-pyridyl) | $IR\nu_{max}^{Nujol}$ (cm$^{-1}$): 3320, 1700, 1660, 1170, 1110<br>m.p. 147-149° C. |

TABLE 1-continued

[Structure: pyrrolidine ring with AcS substituent, COY group, and N-PNZ]

| Reference Example No. | Y | Spectral Data |
|---|---|---|
| 1-21 | −NH−CH$_2$CH$_2$CH$_2$COOPNB | IR$\nu_{max}^{neat}$ (cm$^{-1}$): 1705, 1690, 1520, 1345, 1160, 1110<br>NMR$\delta$ (CDCl$_3$): 2.32(3H, s), 5.22(2H, s), 7.50(2H, d, J=8Hz), 8.19(2H, d, J=8.5Hz) |
| 1-22 | −NH−CH$_2$CONHCH$_3$ | IR$\nu_{max}^{neat}$ (cm$^{-1}$): 3310, 1710, 1635, 1520, 1170, 1120<br>m.p. 200–206° C. |
| 1-23 | −NH−CH$_2$CON(CH$_3$)$_2$ | IR$\nu_{max}^{neat}$ (cm$^{-1}$): 3400, 1700, 1665, 1525, 1345, 1120<br>NMR$\delta$ (CDCl$_3$): 2.33(3H, s), 7.50(2H, d, J=9Hz), 8.20(2H, d, J=9Hz) |
| 1-24 | −NH−CH(CH$_3$)CONH$_2$ | IR$\nu_{max}^{Nujol}$ (cm$^{-1}$): 3400, 3300, 3220, 1700, 1655, 1180, 1110<br>m.p. 203–209° C. |
| 1-25 | −NH−CH(CH$_3$)CONHCH$_3$ | IR$\nu_{max}^{Nujol}$ (cm$^{-1}$): 3300, 1740, 1700, 1650, 1520, 1180<br>m.p. 185–188° C. |
| 1-26 | −N(CH$_3$)−CH$_2$CONH$_2$ | IR$\nu_{max}^{neat}$ (cm$^{-1}$): 3350, 3230, 1695, 1525, 1410, 1350<br>NMR$\delta$ (CDCl$_3$): 2.37(3H, s), 3.23(3H, s), 5.20(2H, s), 7.50(2H, d, J=9Hz), 8.27(2H, d, J=9Hz) |
| 1-27 | −N(CH$_3$)−CH$_2$CONHCH$_3$ | IR$\nu_{max}^{CHCl_3}$ (cm$^{-1}$): 3350, 1690, 1660, 1520, 1340, 1120<br>NMR$\delta$ (CDCl$_3$): 2.36(3H, s), 3.21(2H, s), 5.23(2H, s), 6.93(1H br.s), 7.50(2H, d, J=9Hz), 8.25(2H, d, J=9Hz) |
| 1-28 | −N(CH$_3$)−CH$_2$CON(CH$_3$)$_2$ | IR$\nu_{max}^{CHCl_3}$ (cm$^{-1}$): 1700, 1650, 1520, 1340, 1110<br>NMR$\delta$ (CDCl$_3$): 2.33(3H, s), 7.43(2H, d, J=8Hz), 8.20(2H, d, J=8Hz) |
| 1-29 | −N(thiomorpholine) | IR$\nu_{max}^{neat}$ (cm$^{-1}$): 1695, 1655, 1525, 1427, 1342, 1250, 1110, 1065, 955<br>NMR$\delta$ (CDCl$_3$): 2.32(3H, s), 5.21(2H, s), 7.48(2H, d, J=8.5Hz), 8.18(2H, d, J=8.5Hz) |
| 1-30 | −NH−(2-pyridyl) | IR$\nu_{max}^{CHCl_3}$ (cm$^{-1}$): 3400, 1700, 1520, 1440, 1345, 115<br>NMR$\delta$ (CDCl$_3$): 2.33(3H, s), 8.20(2H, d, J=9Hz)<br>m.p. 150–151° C. |
| 1-31 | −NH−(3-pyridyl) | IR$\nu_{max}^{CHCl_3}$ (cm$^{-1}$): 3300, 1700, 1525, 1345, 1120<br>NMR$\delta$ (CDCl$_3$): 2.33(3H, s), 5.25(2H, s), 7.47(2H, d, J=9Hz), 8.58(1H, d, J=3Hz), 9.50(1H, br.s) |
| 1-32 | −N(azetidine) | IR$\nu_{max}^{neat}$ (cm$^{-1}$): 1705, 1655, 1520, 1430, 1400, 1342, 1112<br>NMR$\delta$ (CDCl$_3$): 2.33(3H, s), 5.20(2H, s), 7.47(2H, d, J=8.5Hz), 8.17(2H, d, J=8.5Hz) |
| 1-33 | −N(2,5-dihydropyrrole) | IR$\nu_{max}^{CHCl_3}$ (cm$^{-1}$): 1705, 1660, 1525, 1345, 1120<br>NMR$\delta$ (CDCl$_3$): 2.35(3H, s), 5.23(2H, s), 7.55(2H, d, J=9Hz) |
| 1-34 | −N(pyrrolidine) | IR$\nu_{max}^{neat}$ (cm$^{-1}$): 1705, 1640, 1516, 1430, 1400, 1342, 1110<br>NMR$\delta$ (CDCl$_3$): 2.31(3H, s), 4.03(2H, dd, J=6 and 8Hz), 4.53(1H, t, J=8Hz), 5.19(2H, s), 7.48(2H, d, J=9Hz), 8.18(2H, d, J=9Hz) |

TABLE 1-continued

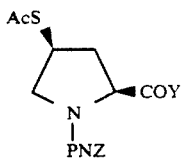

| Reference Example No. | Y | Spectral Data |
|---|---|---|
| 1-35 | —N⟨pyrrolidine-2-CONH₂⟩ | IR$\nu_{max}^{Nujol}$ (cm$^{-1}$): 3430, 1700, 1640, 1345, 1245, 1120<br>m.p. 173–175° C. |
| 1-36 | —N⟨pyrrolidine-3-OH⟩ | IR$\nu_{max}^{CHCl_3}$ (cm$^{-1}$): 3400, 1700, 1650, 1525, 1345, 1120<br>NMRδ (CDCl₃): 2.33(3H, s), 5.17(2H, s), 7.47(2H, d, J=9Hz), 8.18(2H, d, J=9Hz) |
| 1-37 | —N⟨bicyclic amine⟩ | IR$\nu_{max}^{neat}$ (cm$^{-1}$): 1700, 1640, 1520, 1400, 1335, 1100<br>NMRδ (CDCl₃): 2.33(3H, s), 5.22(2H, s), 7.50(2H, d, J=9Hz), 8.20(2H, d, J=9Hz) |
| 1-38 | —N⟨2,6-dimethylpiperidine⟩ (CH₃, CH₃) | IR$\nu_{max}^{neat}$ (cm$^{-1}$): 1710, 1640, 1525, 1345, 1120<br>NMRδ (CDCl₃): 2.35(3H, s), 5.25(2H, s), 7.53(2H, d, J=9Hz), 8.23(2H, d, J=9Hz) |
| 1-39 | —N=C(NMe₂)(NMe₂) | IR$\nu_{max}^{CHCl_3}$ (cm$^{-1}$): 1700, 1610, 1520, 1400, 1350, 1110<br>NMRδ (CDCl₃): 2.33(3H, s), 2.87(6H, s), 2.95(6H, s), 5.25(2H, s), 7.56(2H, d, J=9Hz), 8.22(2H, d, J=9Hz) |
| 1-40 | —N=C(NH₂)(NH₂) | IR$\nu_{max}^{CHCl_3}$ (cm$^{-1}$): 3350, 1705, 1610, 1525, 1345, 1120<br>NMRδ (CDCl₃): 2.33(3H, s), 5.23(2H, s), 8.15(2H, d, J=8Hz) |
| 1-41 | —OCH₃ | IR$\nu_{max}^{Nujol}$ (cm$^{-1}$): 1750, 1705, 1690, 1523, 1441, 1352, 1226, 1170, 1114<br>m.p. 92–93.5° C. |
| 1-42 | —OC₂H₅ | IR$\nu_{max}^{Nujol}$ (cm$^{-1}$): 1748, 1712, 1692, 1524, 1440, 1348, 1223, 1200<br>m.p. 80–81.5° C. |
| 1-43 | —NHNH₂ | IR$\nu_{max}^{Nujol}$ (cm$^{-1}$): 3200, 1720, 1615, 1520, 1350, 1125<br>m.p. 208–213° C. |
| 1-44 | —NHN(CH₃)₂ | IR$\nu_{max}^{Nujol}$ (cm$^{-1}$): 3200, 1710, 1660, 1520, 1340, 1175<br>m.p. 158–159° C. |
| 1-45 | —N(CH₃)(N(CH₃)₂) | IR$\nu_{max}^{neat}$ (cm$^{-1}$): 1715, 1670, 1520, 1340, 1110<br>NMRδ (CDCl₃): 2.32(3H, s), 5.18(2H, s) |
| 1-46 | —NHOPNB | IR$\nu_{max}^{Nujol}$ (cm$^{-1}$): 3200, 1730, 1700, 1680, 1520, 1340, 1120<br>m.p. 166–167° C. |
| 1-47 | —NHOCH₃ | IR$\nu_{max}^{Nujol}$ (cm$^{-1}$): 3240, 1705, 1690, 1520, 1340, 1175<br>m.p. 178–179° C. |
| 1-48 | —NH-(4-pyridyl) | IR$\nu_{max}^{neat}$ (cm$^{-1}$): 1695, 1595, 1520, 1340, 1180, 1110<br>NMRδ (CDCl₃): 2.34(3H, s), 5.31(2H, s), 7.42(2H, d, J=6Hz), 8.48(2H, d, J=6Hz) |
| 1-49 | —N⟨aziridine⟩ | IR$\nu_{max}^{neat}$ (cm$^{-1}$): 1695, 1600, 1520, 1340, 1110<br>NMRδ (CDCl₃): 2.34(4H, s), 2.39(3H, s), 5.18(2H, s), 7.48(2H, d, J=8.5Hz), 8.21(2H, d, J=8.5Hz) |

REFERENCE EXAMPLE 2-1

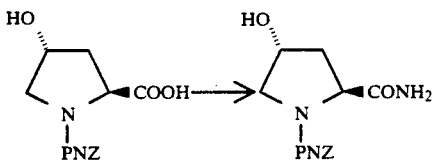

3.10 g of trans-1-(p-nitrobenzyloxycarbonyl)-4-hydroxy-L-proline and 1.10 g of triethylamine were dissolved in 40 ml of dried tetrahydrofuran, and a solution of 1.20 g of ethyl chloroformate in 10 ml of dried tetrahydrofuran was added dropwise thereto at −25° C. to −35° C. After stirring at the same temperature for 50 minutes, 10 ml of concentrated aqueous ammonia was added dropwise to the mixture at −25° to −40° C. The temperature was then gradually elevated to room temperature, and the reaction mixture was stirred for 1 hour, followed by concentration under reduced pressure To the residue were added 20 ml of water and 50 ml of diethyl ether. After ice-cooling, the thus formed white crystals were separated by filtration, washed successively with cool water and cool diethyl ether, and dried under reduced pressure to yield trans-1-(p-nitrobenzyloxycarbonyl)-4-hydroxy-L-prolineamide.

Melting Point: 163.3°–164.0° C.

IR$_{max}^{Nujol}$(cm$^{-1}$): 3460, 3370, 3200, 1687, 1640, 1621, 1539, 1341, 1180, 1078

REFERENCE EXAMPLE 2-2

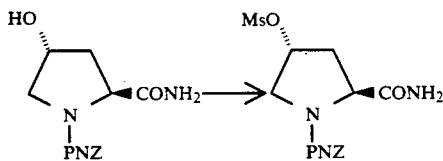

A solution of 1.89 g of methanesulfonyl chloride in 10 ml of dried tetrahydrofuran was added dropwise to a suspension of 2.32 g of trans-1-(p-nitrobenzyloxycarbonyl)-4-hydroxy-L-prolineamide and 1.67 g of triethylamine in 40 ml of dried tetrahydrofuran at room temperature. After stirring for 1 hour, the reaction mixture was concentrated under reduced pressure, and to the residue were added 30 ml of water and 30 ml of diethyl ether. After cooling, the resulting white crystals were separated by filtration, washed successively with cool water and cool diethyl ether and dried under reduced pressure to obtain trans-1-(p-nitrobenzyloxycarbonyl)-4-methanesulfonyloxy-L-prolineamide.

Melting Point: 149.5°–151° C.

IR$_{max}^{Nujol}$(cm$^{-1}$) 3400, 3225, 1715, 1675, 1520, 1340, 1170, 1135

REFERENCE EXAMPLE 2-3

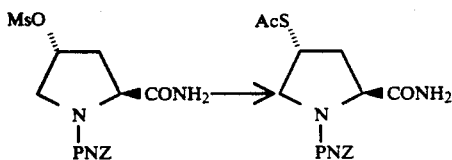

A solution of 642 mg of thioacetic acid in 14 ml of dried dimethylformamide was added to a suspension of 374 mg of 50% sodium hydride in 13 ml of dried dimethylformamide in a nitrogen stream, followed by stirring at room temperature for 25 minutes. To the mixture were added 975 mg of sodium iodide and then a solution of 2.52 g of trans-1-(p-nitrobenzyloxycarbonyl)-4-methanesulfonyloxy-L-prolineamide in 12 ml of dried dimethylformamide, and the resulting mixture was heated at 70° C. for 6 hours while stirring. The reaction mixture was poured into a cool aqueous solution of sodium chloride and extracted with benzene. The extract was washed successively with a 10% aqueous solution of sodium sulfite and a sodium chloride aqueous solution, dried over sodium sulfate and distilled off to remove the solvent. The resulting crude crystals were washed with a warm mixed solvent of tetrahydrofuran and benzene to obtain cis-1-(p-nitrobenzyloxycarbonyl)-4-acetylthio-L-prolineamide.

Melting Point: 168.5°–169.5° C.

IR$_{max}^{Nujol}$(cm$^{-1}$): 3350, 3180, 1715, 1690, 1638, 1510, 1330, 1100

$[\alpha]_D^{30}$ −23° (c=0.334, DMF)

REFERENCE EXAMPLE 2-4

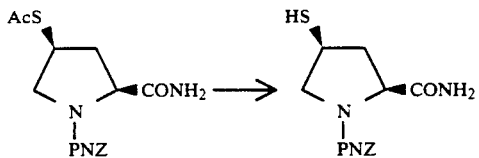

950 mg of (2S,4S)-1-(p-nitrobenzyloxycarbonyl)-2-carbamoyl-4-acetylthiopyrrolidine was dissolved in 95 ml of methanol, and 2.59 ml of a 1N aqueous solution of sodium hydroxide was added thereto at room temperature in an argon stream, followed by stirring at that temperature for 15 minutes. The reaction mixture was neutralized with 2.59 ml of a 1N aqueous solution of hydrochloric acid and distilled off under reduced pressure to remove the methanol. The thus precipitated crystals were filtered and washed with water to obtain (2S,4S)-1-(p-nitrobenzyloxycarbonyl)-2-carbamoyl-4-mercaptopyrrolidine.

Melting Point: 158°–162° C.

REFERENCE EXAMPLE 3-1

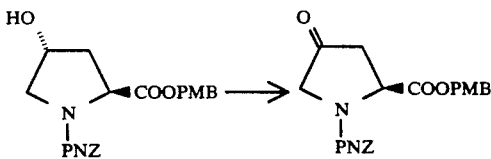

A solution of 0.35 ml of dimethyl sulfoxide in 1 ml of dried methylene chloride was added dropwise to a solution of 0.2 ml of oxalyl chloride in 5 ml of dried methylene chloride at −60° to −70° C. Ten minutes later, 10 ml of a dried methylene chloride solution of 860 mg of trans-1-(p-nitrobenzyloxycarbonyl)-4-hydroxy-L-proline p-methoxybenzyl ester was added dropwise to the above mixture at a temperature of −50° C. or less, followed by stirring for 15 minutes. 1.01 g of triethylamine was then added dropwise thereto, and the resulting mixture was warmed to room temperature. The mixture was diluted with methylene chloride, washed with dilute hydrochloric acid aqueous solution and dried over sodium sulfate. The solvent was removed by distillation, and the residue was purified by silica gel column chromatography to yield 1-(p-nitrobenzyloxycarbonyl)-4-oxo-L-proline p-methoxybenzyl ester.

IR$_{max}^{neat}$ (cm$^{-1}$): 1762, 1740, 1710, 1512, 1345, 1245,
NMR δ (CDCl$_3$): 3.78 (3H, s), 3.95 (2H, s), 5.08 (2H, s), 6.85 (2H, d, J=9Hz), 8.12 (2H, d, J=9Hz) ppm

REFERENCE EXAMPLE 3-2

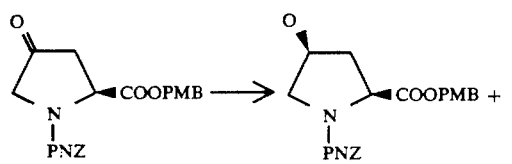

650 mg of 1-(p-nitrobenzyloxycarbonyl)-4-oxo-L-proline p-methoxybenzyl ester was dissolved in 45 ml of ethanol, and 86 mg of sodium borohydride was added thereto in two divided portions at room temperature. After 30 minutes, the reaction mixture was concentrated under reduced pressure at 30° C. or below, and the concentrate was diluted with ethyl acetate, washed with water, dried over sodium sulfate and distilled off to remove the solvent. The residue was purified by silica gel column chromatography to obtain cis-1-(p-nitrobenzyloxycarbonyl)-4-hydroxy-L-proline p-methoxybenzyl ester (450 mg) and trans-1-(p-nitrobenzyloxycarbonyl)-4-hydroxy-L-proline p-methoxybenzyl ester (190 mg).

Trans-compound:
The IR and NMR data were consistent with those obtained for the compound of Reference Example 1-2.

Cis-compound:
IR$_{max}^{neat}$ (cm$^{-1}$): 3400 (br.), 1725, 1515, 1405, 1350, 1250, 1170, 1120
NMR δ (CDCl$_3$): 3.78 (3H, s), 5.08 (2H, s), 6.82 (2H, d, J=9Hz), 8.12 (2H, d, J=9Hz)ppm

REFERENCE EXAMPLE 3—3

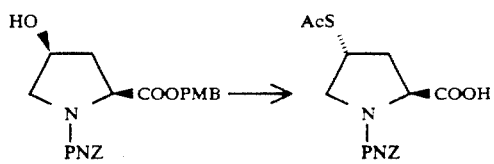

In the same manner as described in Reference Examples 1-3 and 1-4 but using 610 mg of cis-1-(p-nitrobenzyloxycarbonyl)-4-hydroxy-L-proline p-methoxybenzyl ester, trans-1-(p-nitrobenzyloxycarbonyl)-4-acetylthio-L-proline was obtained.

REFERENCE EXAMPLE 3-4

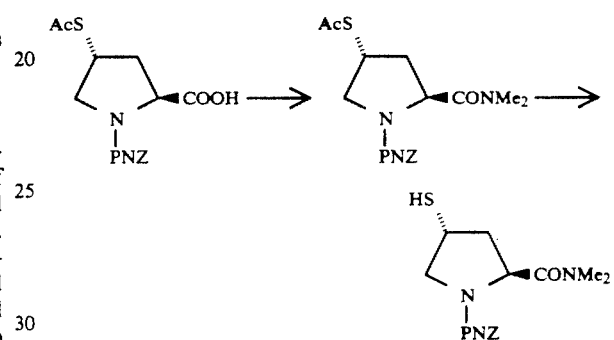

a) In the same manner as described in Reference Example 1-5 but using 180 mg of trans-1-(p-nitrobenzyl- oxycarbonyl)-4-acetylthio-L-proline, 100 mg of (2S,4R)-1-(p-nitrobenzyloxycarbonyl)-2-dimethylcarbamoyl-4-acetylthiopyrrolidine was obtained.

IR$_{max}^{neat}$ (cm$^{-1}$): 1700, 1655, 1515, 1400, 1340, 1115
$[α]_D^{30}$ +32.8° (c=0 375, acetone)

b) In the same manner as described in Reference Example 1-8 but using 80 mg of the thioacetate derivative prepared as in a) above, (2S,4R)-1-(p-nitrobenzyloxycarbonyl)-2-dimethylcarbamoyl-4-mercaptopyrrolidine was obtained.

IR$_{max}^{neat}$ (cm$^{-1}$): 1700, 1650, 1510, 1420, 1400, 1340, 1120
NMR δ (CDCl$_3$): 1.77 (1H, d, J=7Hz), 2.97 (3H, s), 3.16 (3H, s), 5.22 (2H, s), 8.16 (2H, d, J=8.5Hz) ppm In the same manner as described in Reference Example 3-4 but using the corresponding amines, the following thioacetates and mercaptans as shown in Table 2 were obtained.

TABLE 2

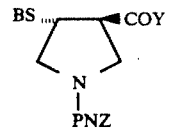

| Reference Example No. | B | Y | | Spectral Data |
|---|---|---|---|---|
| 3-5 | Ac | —NH$_2$ | IR$ν_{max}^{neat}$ (cm$^{-1}$): | 3300(br), 1700(sh), 1685, 1512, 1430, 1400, 1345, 1175, 1115 |
| | | | $[α]_D^{30}$ +7.36° | (c=0.625, acetone) |
| | H | —NH$_2$ | IR$ν_{max}^{neat}$ (cm$^{-1}$): | 1700, 1685, 1515, 1435, 1400, 1342, 1118 |
| | | | NMRδ (CDCl$_3$): | 2.26(1H, d, J=7Hz), 5.22(2H, s), 8.11(2H, d, |

TABLE 2-continued

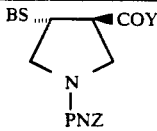

| Reference Example No. | B | Y | Spectral Data |
|---|---|---|---|
| 3-6 | Ac | —N⟨ ⟩ | $J=8.5Hz$)<br>$IR\nu_{max}^{KBr}$ (cm$^{-1}$): 1705, 1645, 1517, 1435, 1400, 1340, 1115<br>NMRδ (CDCl$_3$): 2.33(3H, s), 5.22(2H, s), 8.16(2H, d, J=9Hz) |
| | H | —N⟨ ⟩ | $IR\nu_{max}^{neat}$ (cm$^{-1}$): 1705, 1640, 1515, 1430, 1110 |

REFERENCE EXAMPLE 4-1

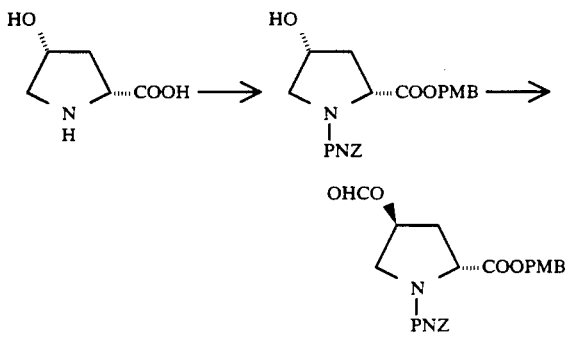

166 mg of cis-1-p-nitrobenzyloxycarbonyl-4-hydroxy-D-proline p-methoxybenzyl ester, which was obtained from cis-4-hydroxy-D-proline in the same manner as in Reference Examples 1-1 and 1-2, and 202 mg of triphenylphosphine were dissolved in 1.5 ml of dried tetrahydrofuran, and 27 mg of formic acid was added to the solution 134 mg of diethyl azodicarboxylate further added thereto at room temperature in a nitrogen stream. After stirring for 30 minutes, the solvent was removed by distillation. The residue was purified by silica gel chromatography to obtain trans-1-p-nitrobenzyloxycarbonyl-4-formyloxy-D-proline p-methoxybenzyl ester.

IR$_{max}^{neat}$ (cm$^{-1}$): 1720, 1515, 1402, 1342, 1245, 1165, 1120

NMR δ (CDCl$_3$) 3.76 (3H, s), 4.50 (2H, t, J=8Hz), 5.08 (2H, s), 5.15 (2H, ABq., J=16Hz), 5.41 (1H, m), 7.97 (1H, s) ppm

REFERENCE EXAMPLE 4-2

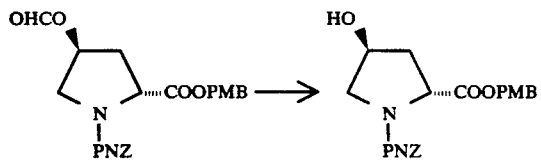

215 mg of trans-1-p-nitrobenzyloxycarbonyl-4-formyloxy-D-proline p-methoxybenzyl ester was dissolved in 1.1 ml of tetrahydrofuran, and 0.93 ml of a 1N aqueous solution of sodium hydroxide was added to the resulting solution. After stirring for 10 minutes, the reaction mixture was diluted with ethyl acetate, washed with a saturated aqueous solution of sodium chloride, dried over sodium sulfate and distilled off to remove the solvent. The resulting residue was purified by silica gel thin layer chromatography to obtain trans-1-p-nitrobenzyloxycarbonyl-4-hydroxy-D-proline p-methoxybenzyl ester.

IR$_{max}^{neat}$(cm$^{-1}$): 3425 (br.), 1735, 1705, 1510, 1400, 1340, 1240, 1162

NMR δ (CDCl$_3$) 2.33 (2H, m), 3.58 (2H, d, J=3.5Hz), 3.73 (3H, s), 5.03 (2H, s), 5.07 (2H, ABq., J=18Hz), 6.73 (2H, d, J=9Hz), 6.77 (2H, d, J=9Hz), 8.00 (2H, d, J=8.5Hz), 8.07 (2H, d, J=8.5Hz)ppm

REFERENCE EXAMPLE 4-3

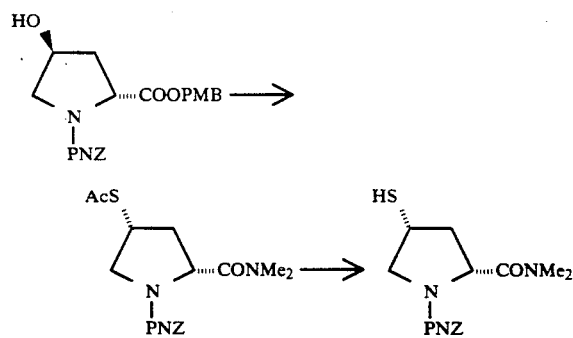

a) In the same manner as described in Reference Examples 1-3, 1-4 and 1-5 but using 110 mg of trans-1-p-nitrobenzyloxycarbonyl-4-hydroxy-D-proline p-methoxybenzyl ester, (2R,4R)-1-p-nitrobenzyloxcarbonyl-2-dimethylcarbamoyl-4-acetylthiopyrrolidine was obtained.

IR$_{max}^{neat}$ (cm$^{-1}$): 1705, 1650, 1515, 1435, 1340, 1115
$[α]_D^{30}$ −7.38° (c=0.210, acetone)

b) In the same manner as described in Reference Example 1-8 but using 42 mg of the thioacetate derivative as obtained in a) above, (2R,4R)-1-p-nitrobenzyloxycarbonyl-2-dimethylcarbamoyl-4-mercaptopyrrolidine was obtained.

IR$_{max}^{neat}$(cm$^{-1}$): 1710, 1660, 1525, 1440, 1347, 1180, 1122

REFERENCE EXAMPLE 4-4

REFERENCE EXAMPLE 5-1

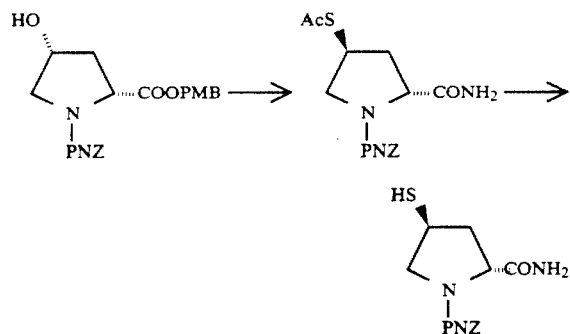

a) In the same manner as described in Reference Examples 1-3, 1-4 and 2-1 but using 110 mg of trans-1-p-nitrobenzyloxycarbonyl-4-hydroxy-D-proline p-methoxybenzyl ester, 40 mg of (2R,4R)-1-p-nitrobenzyloxycarbonyl-2-carbamoyl-4-acetyl-thiopyrrolidine was obtained.

IR$_{max}^{neat}$ (cm$^{-1}$): 1685, 1515, 1400, 1340, 1110
$[\alpha]_D^{30}$ +39.6° (c=0.293, DMF)

b) In the same manner as described in Reference Example 1-8 but using 40 mg of the thioacetate derivative as obtained in a) above, (2R,4R)-1-p-nitrobenzyloxycarbonyl-2-carbamoyl-4-mercaptopyrrolidine was obtained.

IR$_{max}^{Nujol}$ (cm$^{-1}$): 3200, 1710, 1655, 1512, 1340, 1115 a) In the same manner as described in Reference Examples 1-1, 1-2, 1-3, 1-4 and 1-5 but using 300 mg of cis-4-hydroxy-D-proline, 45 mg of (2R,4S)-1-(p-nitrobenzyloxycarbonyl)-2-dimethylcarbamoyl-4-acetylthiopyrrolidine was obtained.

IR$_{max}^{neat}$ (cm$^{-1}$): 1700, 1650, 1520, 1400, 1345, 1120
$[\alpha]_D^{30}$ −29.6° (c=0.215, acetone)

b) In the same manner as described in Reference Example 1-8 but using 30 mg of the thioacetate derivative as obtained in a) above, (2R,4S)-1-(p-nitrobenzyloxycarbonyl)-2-dimethylcarbamoyl-4-mercaptopyrrolidine was obtained.

IR$_{max}^{neat}$ (cm$^{-1}$): 1710, 1655, 1520, 1430, 1405, 1347, 1122

In the same manner as described in Reference Example 5-1 but using the corresponding amines, the following thioacetate derivatives and mercaptan derivatives as shown in Table 3 were obtained.

TABLE 3

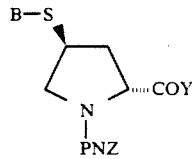

| Reference Example No. | B | Y | Spectral Data | |
|---|---|---|---|---|
| 5-2 | Ac | —NH$_2$ | IR$\nu_{max}^{neat}$ (cm$^{-1}$): | 1705(sh), 1685, 1520, 1425, 1402, 1342, 1122 |
|  |  |  | $[\alpha]_D^{30}$ −6.92° | (c=0.665, acetone) |
|  | H | —NH$_2$ | IR$\nu_{max}^{CHCl_3}$ (cm$^{-1}$): | 1695(sh), 1682, 1515, 1395, 1340, 1115 |
| 5-3 | Ac | —N⟨pyrrolidine⟩ | IR$\nu_{max}^{neat}$ (cm$^{-1}$): | 1695, 1635, 1515, 1430, 1395, 1340, 1115 |
|  | H | —N⟨pyrrolidine⟩ | IR$\nu_{max}^{CHCl_3}$ (cm$^{-1}$): | 1700, 1640, 1520, 1422, 1345, 1120 |
| 5-4 | Ac | —N⟨dihydropyrrole⟩ | IR$\nu_{max}^{neat}$ (cm$^{-1}$): NMRδ (CDCl$_3$): $[\alpha]_D^{23}$ −21° | 1700, 1655, 1620, 1605, 1520, 1340, 1115 2.33(3H, s), 5.22(2H, s), 7.49(2H, d, J=8.5Hz), 8.21(2H, d, J=8.5Hz) (c=0.25, acetone) |
|  | H | —N⟨dihydropyrrole⟩ | IR$\nu_{max}^{CHCl_3}$ (cm$^{-1}$): | 1705, 1660, 1525, 1340, 1120 |

REFERENCE EXAMPLE 6-1

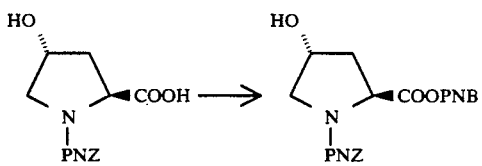

In the same manner as described in Reference Example 1-2 but using 500 mg of trans-1-p-nitrobenzyloxycarbonyl-4-hydroxy-L-proline and 383 mg of p-nitrobenzyl bromide, trans-1-p-nitrobenzyloxcarbonyl-4-hydroxy-L-proline p-nitrobenzyl ester was obtained.

IR$_{max}^{CHCl_3}$ (cm$^{-1}$): 3380 (br.), 1750, 1705, 1520, 1425, 1400, 1342, 1160

NMR δ (CDCl$_3$): 2.20 (3H, m), 3.67 (2H, d, J=3Hz), 4.60 (2H, t, J=8Hz), 5.15 (2H, s), 5.23 (2H, ABq.), 7.47 (4H, d, J=8.5Hz), 8.15 (4H, d, J=8.5Hz) ppm

REFERENCE EXAMPLE 6-2

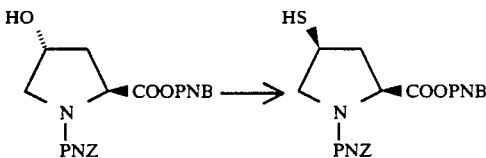

In the same manner as described in Reference Examples 1-3 and 1-8 but using trans-1-p-nitrobenzyloxycarbonyl-4-hydroxy-L-proline p-nitrobenzyl ester, cis-1-p-nitrobenzyloxycarbonyl-4-mercapto-L-proline p-nitrobenzyl ester was obtained.

IR$_{max}^{neat}$ (cm$^{-1}$); 1700, 1685, 1600, 1510, 1430, 1400, 1340, 1105

REFERENCE EXAMPLE 6-3

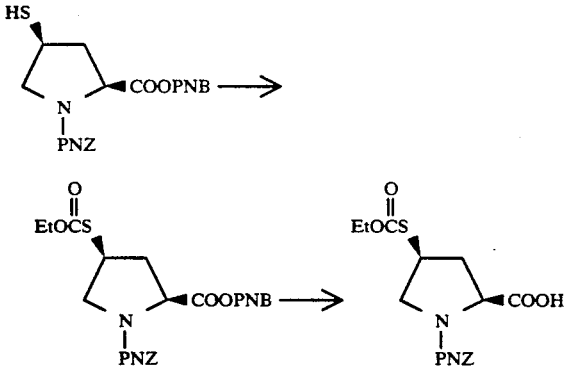

a) 115 mg of cis-1-p-nitrobenzyloxycarbonyl-4-mercapto-L-proline p-nitrobenzyl ester was dissolved in 3 ml of dried tetrahydrofuran, and 30 mg of triethylamine was added thereto. Then, 28.5 mg of ethyl chloroformate was added dropwise thereto under ice-cooling, followed by stirring for 10 minutes. The reaction mixture was diluted with ethyl acetate, washed successively with dilute hydrochloric acid and water, and dried over sodium sulfate. The solvent was removed by distillation to give 133 mg of cis-1-p-nirobenzyloxycarbonyl-4-ethoxycarbonylthio-L-proline p-nitrobenzyl ester.

IR$_{max}^{neat}$ (cm$^{-1}$): 1755, 1710, 1610, 1525, 1405, 1350, 1160, 1015, 850 b) 133 mg of the thus obtained ester derivative was dissolved in 5 ml of a mixture of tetrahydrofuran and water (1:1 by volume), and 0.26 ml of a 1N aqueous solution of sodium hydroxide was added thereto. After stirring at room temperature for 2.5 hours, 0.3 ml of a 1N hydrochloric acid aqueous solution was added to the reaction mixture, and the mixture was extracted with ethyl acetate. The extract was washed with water, dried over sodium sulfate and distilled off to remove the solvent. The residue was subjected to silica gel thin layer chromatography to obtain cis-1-p-nitrobenzyloxycarbonyl-4-ethoxycarbonylthio-L-proline.

IR$_{max}^{neat}$ (cm$^{-1}$); 1700, 1520, 1400, 1340, 1165, 1145

NMR δ (CDCl$_3$) 1.30 (3H, t, J=7Hz), 4.28 (2H, q, J=7Hz), 5.24 (2H, s), 7.50 (2H, d, J=9Hz), 8.17 (2H, d, J=9Hz) ppm

REFERENCE EXAMPLE 6-4

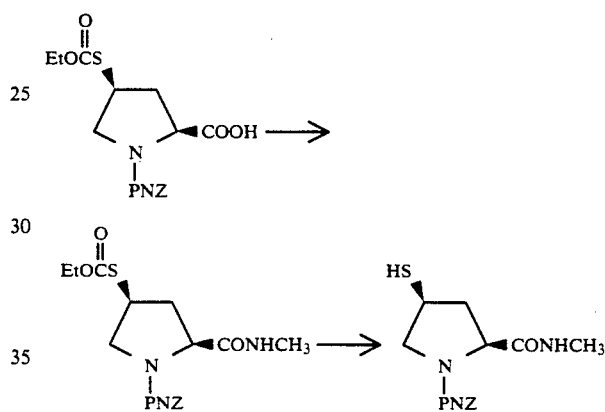

a) 72 mg of cis-1-p-nitrobenzyloxycarbonyl-4-ethoxycarbonylthio-L-proline was dissolved in 3 ml of dried tetrahydrofuran, and 40 mg of triethylamine was added thereto. Under ice-cooling, 41 mg of ethyl chloroformate was added dropwise thereto, followed by stirring for 15 minutes. 1.5 ml of a 40% aqueous solution of methylamine was added dropwise to the mixture, followed by stirring for 15 minutes. The reaction mixture was diluted with ethyl acetate, washed successively with dilute hydrochloric acid and water, dried over sodium sulfate and distilled off to remove the solvent, thereby to obtain (2S,4S)-1-p-nitrobenzyloxycarbonyl-2-methylcarbamoyl-4-ethoxycarbonylthiopyrrolidine.

IR$_{max}^{Nujol}$ (cm$^{-1}$): 3290, 1705, 1660, 1520, 1425, 1405, 1345, 1180, 1160

NMR δ (CDCl$_3$): 1.30 (3H, t, J=8Hz), 2.80 (3H, d, J=5Hz), 4.27 (2H, q, J=8Hz), 5.22 (2H, s), 7.48 (2H, d, J=9Hz), 8.18 (2H, d, J=9Hz) ppm b) 82 mg of the methylcarbamoyl derivative as prepared in a) above was dissolved in 4 ml of a mixture of methanol and water (1:1 by volume), and 0.25 ml of a 1N aqueous solution of sodium hydroxide was added thereto. After stirring at room temperature for 30 minutes, 0.27 ml of a 1 hydrochloric acid aqueous solution was added thereto. The resulting mixture was extracted with ethyl acetate, and the extract was washed with water, dried over sodium sulfate and distilled off to remove the solvent, thereby to obtain (2S,4S)-1-p-nitrobenzyloxycarbonyl-2-methylcarbamoyl-4-mercaptopyrrolidine.

IR$_{max}$$^{Nujol}$ (cm$^{-1}$): 3280, 1710, 1650, 1510, 1340, 1165
NMR δ (CDCl$_3$): 2.79 (3H, d, J=5Hz), 4.27 (2H, t,
J=8Hz), 5.23 (2H, s), 7.50 (2H, d, J=9Hz), 8.20 (2H, d, J=9Hz) ppm In the same manner as described in Reference Example 6-4(a) but using the corresponding amines, the following thiocarbonates as shown in Table 4 were obtained.

TABLE 4

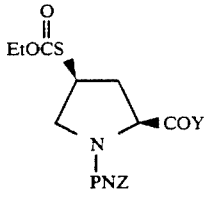

| Reference Example No. | Y | Spectral Data |
|---|---|---|
| 6-5 | −N(H)CH$_2$CH$_2$OH | IRν$_{max}$$^{neat}$ (cm$^{-1}$): 3350, 1705, 1520, 1405, 1345, 1170, 1150<br>NMRδ (CDCl$_3$): 1.27(3H, t, J=7Hz), 4.23(2H, q, J=7Hz), 5.18(2H, s), 7.44(2H, d, J=9Hz), 8.13(2H, d, J=9Hz) |
| 6-6 | −N(H)CH$_2$CH$_2$N(CH$_3$)CH$_3$ | IRν$_{max}$$^{neat}$ (cm$^{-1}$): 1710, 1520, 1400, 1345, 1170, 1148<br>NMRδ (CDCl$_3$): 1.28(3H, t, J=7Hz), 2.19(6H, s), 4.24(2H, q, J=7Hz), 5.20(2H, s), 7.47(2H, d, J=9Hz), 8.13(2H, d, J=9Hz) |

The following mercaptans as shown in Table 5 were obtained in the same manner as described in Reference Example 1-8 or 6-4(b).

TABLE 5

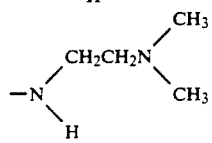

| Reference Example No. | Y | Spectral Data |
|---|---|---|
| 7-1 | −N(C$_2$H$_5$)C$_2$H$_5$ | IRν$_{max}$$^{neat}$ (cm$^{-1}$): 1705, 1640, 1520, 1430, 1400, 1345, 1105 |
| 7-2 | −N(H)CH(CH$_3$)CH$_3$ | IRν$_{max}$$^{neat}$ (cm$^{-1}$): 3290, 1710, 1650, 1520, 1403, 1340 |
| 7-3 | −N(H)CH$_2$CH=CH$_2$ | IRν$_{max}$$^{neat}$ (cm$^{-1}$): 3290, 1717, 1660, 1520, 1410, 1350 |
| 7-4 | −N(H)CH$_2$CONH$_2$ | IRν$_{max}$$^{Nujol}$ (cm$^{-1}$): 3420, 3300, 1700(sh), 1675, 1640, 1510, 1340 |
| 7-5 | −N(H)CH$_2$CH$_2$OH | IRν$_{max}$$^{Nujol}$ (cm$^{-1}$): 3270, 1710, 1650, 1505, 1340<br>NMRδ (CDCl$_3$): 5.20(2H, s), 7.49(2H, q, J=8.5Hz), 8.16(2H, d, J=8.5Hz) |
| 7-6 | −N(CH$_3$)CH$_2$CH$_2$OH | IRν$_{max}$$^{neat}$ (cm$^{-1}$): 3400, 1690, 1640, 1515, 1405, 1345 |
| 7-7 | −N(CH$_3$)CH$_2$PH | IRν$_{max}$$^{neat}$ (cm$^{-1}$): 1705, 1650, 1515, 1400, 1340 |
| 7-8 | −N(piperidine) | IRν$_{max}$$^{neat}$ (cm$^{-1}$): 1710, 1645, 1520, 1440, 1345, 1245, 1025 |

TABLE 5-continued

Structure: pyrrolidine with HS on 4-position, COY on 2-position, N-PNZ

| Reference Example No. | Y | Spectral Data | |
|---|---|---|---|
| 7-9 | —N(morpholine, O) | IR$\nu_{max}^{neat}$ (cm$^{-1}$): | 1710, 1655, 1520, 1430, 1405, 1342, 1112 |
| 7-10 | —N(CH$_3$)(n-C$_4$H$_9$) | IR$\nu_{max}^{neat}$ (cm$^{-1}$): | 1710, 1650, 1520, 1405, 1345, 1205 |
| 7-11 | —N(H)(CH$_2$-2-pyridyl) | IR$\nu_{max}^{Nujol}$ (cm$^{-1}$): | 3300, 1725, 1660, 1520, 1345, 1110 |
| 7-12 | —NH-CH$_2$CH$_2$CH$_2$COOPNB | IR$\nu_{max}^{neat}$ (cm$^{-1}$): | 3280, 1730(sh), 1710, 1645, 1510, 1340 |
| 7-13 | —N(H)CH$_2$CONHCH$_3$ | IR$\nu_{max}^{Nujol}$ (cm$^{-1}$): | 3320, 1725, 1640, 1520, 1405, 1345 |
| 7-14 | —N(H)CH$_2$CON(CH$_3$)$_2$ | NMR$\delta$ (CDCl$_3$): | 1.87(1H, d, J=7Hz), 2.96(3H, s), 2.98(3H, s), 4.33(1H, t, J=7.5Hz), 5.24(2H, s), 7.48(2H, d, J=9Hz), 8.18(2H, d, J=9Hz) |
| 7-15 | —N(H)CH(CH$_3$)CONH$_2$ | IR$\nu_{max}^{Nujol}$ (cm$^{-1}$): | 3300, 1700, 1680, 1655, 1520, 1345 |
| 7-16 | —N(H)CH(CH$_3$)CONHCH$_3$ | IR$\nu_{max}^{Nujol}$ (cm$^{-1}$): | 3310, 1722, 1650, 1525, 1350 |
| 7-17 | —N(H)CH(CH$_3$)CON(CH$_3$)$_2$ | IR$\nu_{max}^{Nujol}$ (cm$^{-1}$): | 3325, 1710, 1640, 1520, 1345 |
| 7-18 | —N(CH$_3$)CH$_2$CONH$_2$ | IR$\nu_{max}^{neat}$ (cm$^{-1}$): | 3350(br), 1690, 1660(sh), 1520, 1405, 1345 |
| 7-19 | —N(CH$_3$)CH$_2$CONHCH$_3$ | IR$\nu_{max}^{neat}$ (cm$^{-1}$): | 3370, 1700, 1665, 1525, 1410, 1350 |
| 7-20 | —N(CH$_3$)CH$_2$CON(CH$_3$)$_2$ | IR$\nu_{max}^{neat}$ (cm$^{-1}$): | 3500, 1710, 1660, 1520, 1405, 1345 |
| 7-21 | —N(thiomorpholine, S) | IR$\nu_{max}^{neat}$ (cm$^{-1}$): | 3245, 1700, 1645, 1520, 1340, 1190, 1165, 1107, 1065, 950, 850 |
| 7-22 | —NH-(2-pyridyl) | IR$\nu_{max}^{CHCl_3}$ (cm$^{-1}$): | 3410, 1710, 1525, 1440, 1345, 1305 |

TABLE 5-continued

Structure: pyrrolidine with HS at 4-position, COY at 2-position, N-PNZ

| Reference Example No. | Y | Spectral Data |
|---|---|---|
| 7-23 | —NH-(3-pyridyl) | IR ν$_{max}$$^{Nujol}$ (cm$^{-1}$): 3250, 1710, 1670, 1525, 1345, 1175 |
| 7-24 | —N(azetidinyl) | IR ν$_{max}$$^{neat}$ (cm$^{-1}$): 1710, 1650, 1518, 1435, 1400, 1345, 1170, 1110 |
| 7-25 | —N(2,5-dihydropyrrolyl) | IR ν$_{max}$$^{CHCl_3}$ (cm$^{-1}$): 1710, 1660, 1520, 1345, 1170, 1110 |
| 7-26 | —N(pyrrolyl) | IR ν$_{max}$$^{CHCl_3}$ (cm$^{-1}$): 1720, 1525, 1470, 1340, 1170, 1110 |
| 7-27 | —N(2-carbamoylpyrrolidinyl) | IR ν$_{max}$$^{CHCl_3}$ (cm$^{-1}$): 3470(br), 1700, 1640, 1520, 1340, 1120 |
| 7-28 | —N(3-hydroxypyrrolidinyl) | IR ν$_{max}$$^{CHCl_3}$ (cm$^{-1}$): 3420(br), 1700, 1645, 1520, 1340, 1165 |
| 7-29 | —N(bicyclic amine) | IR ν$_{max}$$^{CHCl_3}$ (cm$^{-1}$): 1710, 1640, 1525, 1345, 1170, 1015 |
| 7-30 | —N(2,6-dimethylpiperidinyl) | NMR δ (CDCl$_3$): 1.95(1H, d, J=8Hz), 5.25(2H, s), 7.52(2H, d, J=9Hz), 8.21(2H, d, J=9Hz) |
| 7-31 | —N=C(N(CH$_2$)$_2$)(N(CH$_3$)$_2$) | IR ν$_{max}$$^{neat}$ (cm$^{-1}$): 1705, 1600, 1520, 1400, 1340, 1160 |
| 7-32 | —N=C(NH$_2$)(NH$_2$) | IR ν$_{max}$$^{CHCl_3}$ (cm$^{-1}$): 3420, 1695, 1610, 1522, 1350, 1110 |
| 7-33 | —OCH$_3$ | IR ν$_{max}$$^{neat}$ (cm$^{-1}$): 1745, 1710, 1605, 1520, 1430, 1400, 1345, 1205, 1167, 1110 |
| 7-34 | —OC$_2$H$_5$ | IR ν$_{max}$$^{neat}$ (cm$^{-1}$): 1740, 1710, 1522, 1430, 1402, 1342, 1200, 1170, 1110 |
| 7-35 | —NHNH$_2$ | IR ν$_{max}$$^{neat}$ (cm$^{-1}$): 3180, 3050, 1720, 1615, 1520, 1350 |
| 7-36 | —NHN(CH$_3$)$_2$ | IR ν$_{max}$$^{Nujol}$ (cm$^{-1}$): 3205, 1720, 1660, 1520, 1345, 1180 |
| 7-37 | —N(CH$_3$)(N(CH$_3$)$_2$) | IR ν$_{max}$$^{neat}$ (cm$^{-1}$): 1706, 1662, 1520, 1340, 1165, 1105 |
| 7-38 | —NHOPNB | IR ν$_{max}$$^{Nujol}$ (cm$^{-1}$): 3200, 1715, 1665, 1515, 1345, 1170 |
| 7-39 | —NHOCH$_3$ | IR ν$_{max}$$^{Nujol}$ (cm$^{-1}$): 3200, 1715, 1670, 1520, 1340, 1170 |
| 7-40 | —N(4-carbamoylpiperidinyl) | IR ν$_{max}$$^{CHCl_3}$ (cm$^{-1}$): 1690, 1650, 1525, 1405, 1345, 1170, 1110 |

TABLE 5-continued

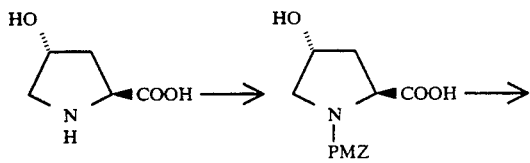

| Reference Example No. | Y | Spectral Data | |
|---|---|---|---|
| 7-41 | −N⟨ | $IR\nu_{max}^{neat}$ (cm$^{-1}$): | 1700, 1520, 1400, 1340, 1200, 1160, 1105 |
| 7-42 | −N⟨pyrrolidine⟩ | $IR\nu_{max}^{neat}$ (cm$^{-1}$): | 1708, 1645, 1520, 1440, 1405, 1350, 1170, 1115 |
| 7-43 | −NH−pyridyl | $IR\nu_{max}^{neat}$ (cm$^{-1}$): | 1700, 1600, 1515, 1105 |

REFERENCE EXAMPLE 8-1

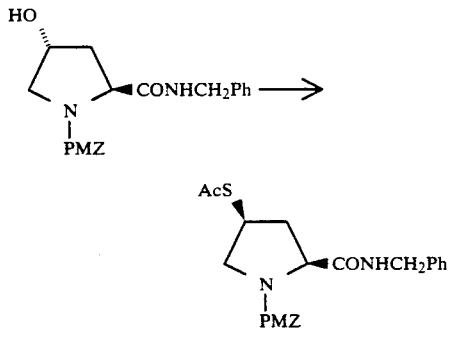

a) In the same manner as described in Reference Example 1—1 but using 10 g of trans-4-hydroxy-L-proline and 23.2 g of S-p-methoxybenzyloxycarbonyl-4,6-dimethyl-2-mercaptopyrimidine, trans-1-(p-methoxybenzyloxycarbonyl)-4-hydroxy-L-proline was obtained.

$IR_{max}^{neat}$ (cm$^{-1}$): 3400 (br.), 1692, 1430, 1355, 1245, 1170, 1122

NMR δ (CDCl$_3$): 2.23 (2H, m), 3.73 (3H, s), 5.00 (2H, s), 6.78 (2H, d, J=9Hz), 7.20 (2H, d, J=9Hz) ppm b) In the same manner as described in Reference Example 2-1 but using 0.57 g of the proline derivative as prepared in a) above and 0.215 g of benzylamine, trans-1-p-methoxybenzyloxycarbonyl-4-hydroxy-L-benzylprolineamide was obtained.

$IR_{max}^{Nujol}$(cm$^{-1}$): 3375, 3300, 1665, 1248, 1165, 1120, 1025

NMR δ (CDCl) : 3.76 (3H, s), 4.35 (4H, m), 4.96 (2H, s), 6.79 (2H, d, J=9Hz), 7.20 (5H, s) ppm c) In the same manner as described in Reference Example 1-3 but using 0.5 g of the benzylprolineamide as prepared in b) above, (2S,4S)-1-p-methoxybenzyloxycarbonyl-2-benzylcarbamoyl-4-acetylthiopyrrolidine was obtained.

$IR_{max}^{Nujol}$ (cm$^{-1}$): 3280, 1690, 1675, 1240

NMR δ (CDCl$_3$): 2.27 (3H, s), 3.82 (3H, s), 4.42 (2H, d, J=6Hz), 5.05 (2H, s), 6.87 (2H, d, J=8Hz), 7.23 (2H, d, J=8Hz), 7.28 (5H, s) ppm

REFERENCE EXAMPLE 8-2

177 mg of (2S,4S)-1-p-methoxybenzyloxycarbonyl-2-benzylcarbamoyl-4-acetylthiopyrrolidine and 86 mg of anisole were dissolved in 0.5 ml of trifluoroacetic acid, followed by stirring at room temperature for 30 minutes. The reaction mixture was concentrated under reduced pressure, diluted with ethyl acetate, washed successively with an aqueous solution of sodium bicarbonate and water and dried over sodium sulfate. The solvent was removed by distillation, and the residue was subjected to silica gel thin layer chromatography to obtain (2S,4S)-2-benzylcarbamoyl-4-acetylthiopyrrolidine.

$IR_{max}^{neat}$ (cm$^{-1}$): 3325, 1690, 1510, 1400, 1350, 1120, 950

NMR δ (CDCl$_3$): 2.28 (3H, s), 3.83 (2H, m), 4.42 (2H, d, J=6Hz), 7.32 (5H, s) ppm

REFERENCE EXAMPLE 9-1

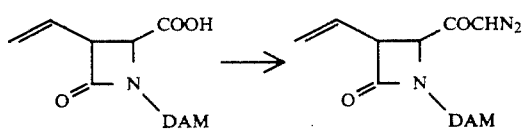

7 g of 1-(di-p-anisylmethyl-3-ethenyl-4-carboxy-2-azetidinone was dissolved in 50 ml of dried methylene chloride, and 0.8 ml of dimethylformamide was added to the resulting solution. 2 ml of oxalyl chloride was added dropwise thereto under ice-cooling, followed by stirring at room temperature for 2 hours. The reaction mixture was concentrated under reduced pressure, and to the concentrate was added 50 ml of dried methylene chloride, followed by concentration again under reduced pressure. The resulting residue was dried in vacuo and then dissolved in 100 ml of dried diethyl ether. The resulting solution was added dropwise under ice-cooling to 120 ml of a 0.17M solution of diazomethane in diethyl ether to which 4 ml of triethylamine had been added, followed by stirring at the same temperature for 1.5 hours. The reaction mixture was diluted with ethyl acetate, washed successively with a 1N aqueous solution of hydrochloric acid and water, dried over sodium sulfate and distilled off to remove the solvent. The resulting oily residue was purified by silica gel chromatography to obtain 1-(di-p-anisylmethyl)-3-ethenyl-4-diazoacetyl-2-azetidinone.

IR$_{max}^{neat}$ (cm$^{-1}$): 2110, 1755, 1640, 1612, 1505, 1240, 1177, 1030, 828

NMR δ (CDCl$_3$): 3.78 (6H, s), 5.00 (1H, s), 5.80 (1H, s), 6.84 (4H, d, J=8.5Hz) ppm

REFERENCE EXAMPLE 9-2

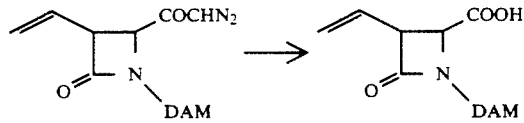

0.7 g of 1-(di-p-anisylmethyl)-3-ethenyl-4-diazoacetyl-2-azetidinone was dissolved in 300 ml of methylene chloride, and 1 ml of water was added thereto. The mixture was irradiated with light for 1 hour using a high pressure mercury lamp while removing oxygen from the system under ice-cooling. Then, the mixture was extracted with a 1N aqueous solution of sodium hydroxide. The aqueous layer was rendered acidic with hydrochloric acid and extracted with ethyl acetate. The extract was washed with water, dried over sodium sulfate and distilled off to remove the solvent thereby obtaining 1-(di-p-anisylmethyl)-3-ethenyl-4-carboxymethyl-2-azetidinone.

IR$_{max}^{neat}$ (cm$^{-1}$): ~3000, 1700, 1612, 1510, 1300, 1180, 1030, 820

NMR δ (CDCl$_3$): 2.35 (2H, d, J=6Hz), 3.73 (6H, s), 5.80 (1H, s), 6.78 (4H, d, J=9.0Hz), 7.08 (4H, d, J=9.0Hz) ppm

REFERENCE EXAMPLE 9-3

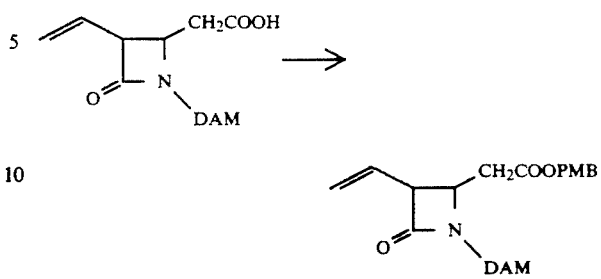

2.3 g of 1-(di-p-anisylmethyl)-3-ethenyl-4-carboxymethyl-2-azetidinone was dissolved in 50 ml of dried dimethylformamide, and 1.5 ml of triethylamine was added thereto. 1.3 g of p-methoxybenzyl chloride was then added dropwise to the mixture, followed by stirring at 70° C. for 3 hours. The reaction mixture was diluted with ethyl acetate and diethyl ether, washed successively with dilute hydrochloric acid and water, dried over sodium sulfate and distilled off to remove the solvent thereby obtaining 1-(di-p-anisylmethyl)-3-ethenyl-4-p-methoxybenzyloxycarbonylmethyl-2-azetidinone.

IR$_{max}^{neat}$ (cm$^{-1}$): 1750, 1612, 1510, 1250, 1175, 1033

NMR δ (CDCl$_3$); 2.36 (2H, d, J=6.5Hz), 3.72 (6H, s), 3.75 (3H, s), 4.83 (2H, s), 5.78 (1H, s) ppm

REFERENCE EXAMPLE 9-4

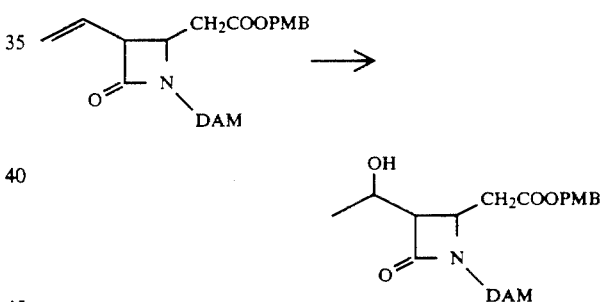

2.85 g of 1-(di-p-anisylmethyl)-3-ethenyl-4-p-methoxybenzyloxycarbonylmethyl-2-azetidinone was dissolved in 14 ml of tetrahydrofuran, and 7 ml of water and 2.0 g of mercury (II) acetate were added thereto, followed by stirring at 35° C. for 5 hours. 12 ml of a 1N aqueous solution of sodium hydroxide was added thereto at 0° C., and to the resulting mixture was then added dropwise a solution of 0.25 g of sodium borohydride in 1 ml of a 1N aqueous solution of sodium hydroxide. After stirring at the same temperature for 15 minutes, the reaction mixture was neutralized with a 2N hydrochloric acid aqueous solution. Diethyl ether was added thereto, followed by filtration using Celite. The filtrate was extracted with diethyl ether, and the extract was washed with a saturated aqueous solution of sodium chloride, dried over sodium sulfate and distilled off to remove the solvent, thereby to obtain 2.6 g of 1-(di-p-anisylmethyl)-3-(1-hydroxyethyl)-4-p-methoxybenzyloxycarbonylmethyl-2-azetidinone.

IR$_{max}^{neat}$ (cm$^{-1}$): 3430, 1730, 1615, 1510, 1247, 1178, 1030, 820

NMR δ (CDCl₃) 1.23 (3H, d, J=6.5Hz), 2.42 (2H, d, J=7Hz), 3.77 (9H, s), 4.95 (2H, s), 5.78 (1H, s) ppm

REFERENCE EXAMPLE 9-5

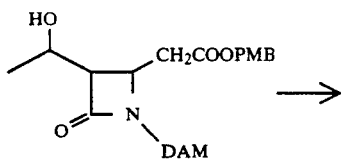

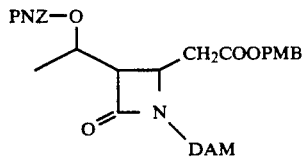

2.6 g of 1-(di-p-anisylmethyl)-3-(1-hydroxyethyl)-4-p-methoxybenzyloxycarbonylmethyl-2-azetidinone was dissolved in 15 ml of dried methylene chloride, and 1.22 g of 4-dimethylaminopyridine was added thereto. Under ice-cooling, a solution of 1.3 g of p-nitrobenzyl chloroformate in 7 ml of dried methylene chloride was added dropwise to the mixture, followed by stirring at room temperature for 1 hour. To the reaction mixture were added methylene chloride and water, and the methylene chloride layer was washed successively with a 1N hydrochloric acid aqueous solution, water, a 5% aqueous solution of sodium bicarbonate and water, and dried over sodium sulfate. The solvent was removed by distillation, and the residue was purified by silica gel chromatography to obtain 2.2 g of 1-(di-p-anisylmethyl)-3-(1-p-nitrobenzyloxycarbonyloxyethyl)-4-p-methoxybenzyloxycarbonylmethyl-2-azetidinone.

IR$_{max}^{neat}$ (cm⁻¹): 1755, 1610, 1510, 1350, 1245, 1175, 1030

NMR δ (CDCl₃): 1.35 (3H, d, J=6.5Hz), 2.40 (2H, d, J=6.5Hz), 3.09 (1H, dd, J=2.5 and 6Hz}, 3.73 (6H, s), 3.77 (3H, s), 4.91 (2H, s), 5.18 (2H, s), 5.71 (1H, s) ppm

REFERENCE EXAMPLE 9-6

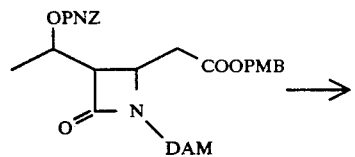

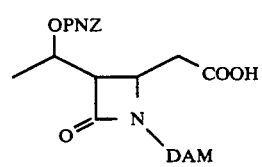

2.2 g of 1-(di-p-anisylmethyl)-3-(1-p-nitrobenzyloxycarbonyloxyethyl)-4-p-methoxybenzyloxycarbonylmethyl-2-azetidinone was dissolved in 20 ml of dried methylene chloride, and 0.88 g of m-dimethoxybenzene and 2.5 ml of trifluoroacetic acid were added to the solution, followed by stirring at room temperature for 4 hours. The solvent was removed by distillation, and the resulting oily residue was subjected to silica gel chromatography to obtain 1.75 g of 1-(di-p-anisylmethyl)-3-(1-p-nitrobenzyloxycarbonyloxyethyl)-4-carboxymethyl-2-azetidinone.

IR$_{max}^{neat}$ (cm⁻¹): ~3000, 1745, 1615, 1510, 1250, 1180, 1035

NMR δ (CDCl₃): 1.35 (3H, d, J=6.5Hz), 2.35 (2H, d, J=6.5Hz), 3.10 (1H, m), 3.73 (6H, s), 5.16 (2H, s), 5.75 (1H, s), 6.73 (4H, d, J=9Hz), 7.46 (2H, d, J=9Hz), 8.10 (2H, d, J=9Hz) ppm

REFERENCE EXAMPLE 9-7

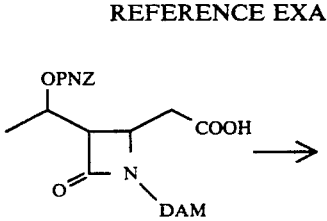

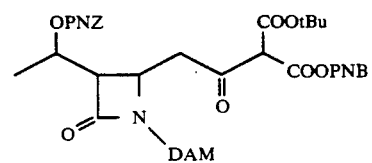

0.8 g of 1-(di-p-anisylmethyl)-3-(1-p-nitrobenzyloxycarbonyloxyethyl)-4-carboxymethyl-2-azetidinone was dissolved in 20 ml of dried methylene chloride, and 0.17 ml of N-methylmorpholine was added thereto. After cooling to −10° C. or less, 0.15 ml of ethyl chloroformate was added dropwise thereto, followed by stirring for 30 minutes. Separately, 0.81 g of t-butyl-(p-nitrobenzyl) malonate was dissolved in 15 ml of dried tetrahydrofuran, and 0.14 g of sodium hydride (50% purity) was added to the resulting solution in a nitrogen stream under ice-cooling, followed by stirring at that temperature for 30 minutes. The resulting solution was added dropwise to the above prepared solution of a mixed anhydride at a temperature of −10° C. or less, followed by stirring for 1 hour. The reaction mixture was warmed to room temperature and concentrated under reduced pressure. The concentrate was diluted with cool water and ethyl acetate, washed successively with a 1N aqueous solution of hydrochloric acid and water, dried over sodium sulfate and distilled off to remove the solvent. The resulting residue was purified by silica gel chromatography to obtain 1-(di-p-anisylmethyl)-3-(1-p-nitrobenzyloxycarbonyloxyethyl)-4-[3-t-butoxycarbonyl-3-(p-nitrobenzyloxycarbonyl)-2-oxopropyl]-2-azetidinone.

IR$_{max}^{neat}$ (cm⁻¹): 1750, 1610, 1510, 1345, 1250

NMR δ (CDCl₃): 1.38 (9H, s), 3.75 (6H, s), 5.17 (4H, s), 5.77 (1H, br. s), 6.77 (4H, d, J=8.5Hz), 7.45 (4H, d, J=9Hz), 8.15 (4H, d, J=9Hz) ppm

REFERENCE EXAMPLE 9-8

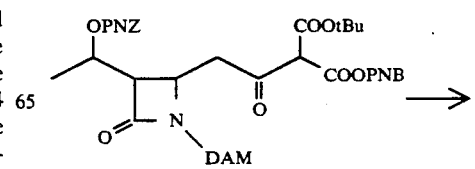

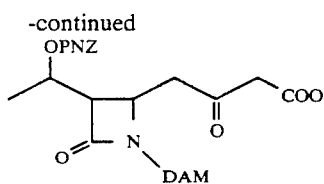

2.3 g of 1-(di-p-anisylmethyl)-3-(1-p-nitrobenzyloxycarbonyloxyethyl)-4-[3-t-butoxycarbonyl-3-p-nitrobenzyloxycarbonyl)-2-oxopropyl]-2-azetidinone was dissolved in 120 ml of dried methylene chloride, and 10 ml of trifluoroacetic acid was added to the solution, followed by stirring at room temperature for 1 hour. The reaction mixture was washed with an aqueous solution of sodium bicarbonate and then with water, dried over sodium sulfate and distilled off to remove the solvent. The residue was purified by silica gel chromatography to obtain 1-(di-p-anisylmethyl)-3-(1-p-nitrobenzyloxycarbonyloxyethyl)-4-[3-(p-nitrobenzyloxycarbonyl)-2-oxopropyl]-2-acetidinone.

IR$_{max}^{neat}$ (cm$^{-1}$): 1748, 1720 (sh.), 1610, 1510, 1345, 1250

NMR δ (CDCl$_3$): 1.41 (3H, d, J=6.5Hz), 2.61 (2H, d, J=6.5Hz), 3.27 (2H, s), 3.76 (6H, s), 5.77 (1H, s), 6.82 (4H, d, J=9Hz), 7.47 (2H, d, J=9Hz), 7.53 (2H, d, J=9Hz), 8.20 (4H, d, J=9Hz) ppm

REFERENCE EXAMPLE 9-9

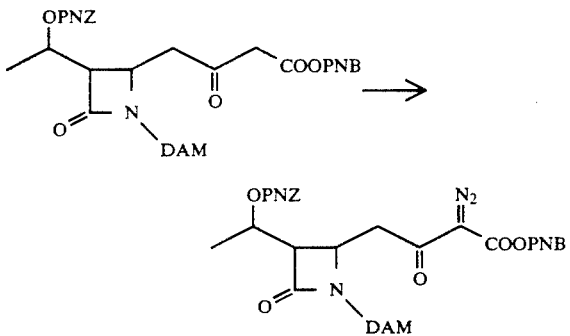

1.9 g of 1-(di-p-anisylmethyl)-3-(1-p-nitrobenzyloxycarbonyloxyethyl)-4-[3-(p-nitrobenzyloxycarbonyl)-2-oxopropyl]-2-azetidinone and 660 mg of p-carboxybenzenesulfonyl azide were dissolved in 50 ml of dried acetonitrile, and 1.4 ml of triethylamine was added thereto dropwise in a nitrogen stream under ice-cooling. After stirring at that temperature for 15 minutes, the reaction mixture was diluted with ethyl acetate, and the thus formed precipitate was filtered. The filtrate was concentrated under reduced pressure, and the resulting oily residue was subjected to silica gel chromatography to obtain 1-(di-p-anisylmethyl)-3-(1-p-nitrobenzyloxycarbonyloxyethyl)-4-[3-(p-nitrobenzyloxycarbonyl)-2-oxo-3-diazopropyl]-2-azetidinone.

IR$_{max}^{neat}$ (cm$^{-1}$): 2150, 1750, 1720 (sh.), 1650, 1510, 1250, 1350

NMR δ (CDCl$_3$): 1.38 (3H, d, J=6.5Hz), 2.95 (2H, d, J=6.5Hz), 3.73 (6H, s), 5.17 (2H, s), 5.24 (2H, s), 5.74 (1H, s), 6.71 (2H, d, J=9Hz), 6.76 (2H, d, J=9Hz), 7.08 (2H, d, J=9Hz), 7.14 (2H, d, J=9Hz), 7.42 (4H, d, J=9Hz), 8.11 (2H, d, J=9Hz), 8.16 (2H, d, J=9Hz) ppm

REFERENCE EXAMPLE 9-10

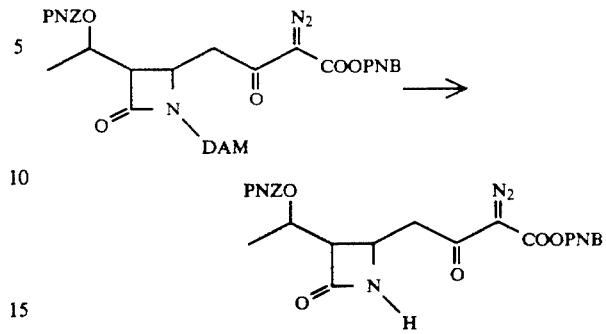

1.27 g 1-(di-p-anisylmethyl)-3-(1-p-nitrobenzyloxycarbonyloxyethyl)-4-[3-(p-nitrobenzyloxycarbonyl)-2-oxo-3-diazopropyl]-2-azetidinone was dissolved in 50 ml of acetonitrile-water (9:1 by volume), and 2.7 g of ceric ammonium nitrate was added thereto all at once under ice-cooling. After vigorously stirring, the mixture was further stirred at room temperature for 30 minutes. Cool water was added to the reaction mixture, and the mixture was extracted with ethyl acetate. The extract was washed with water and dried over sodium sulfate. The solvent was distilled off, and the resulting residue was purified by silica gel chromatography to obtain 3-(1-p-nitrobenzyloxycarbonyloxyethyl)-4-[3-(p-nitrobenzyloxycarbonyl)-2-oxo-3-diazopropyl]-2-azetidinone.

IR$_{max}^{neat}$ (cm$^{-1}$): 2145, 1750, 1720, 1650, 1520, 1345, 1260

NMR δ (CDCl$_3$): 1.45 (3H, d, J=6.5Hz), 3.01 (1H, dd, J=9 and 18Hz), 3.29 (1H, dd, J=4.5 and 18Hz), 4.00 (1H, m), 5.24 (2H, s), 5.36 (2H, s), 6.12 (1H, s), 7.55 (4H, d, J=8.5Hz), 8.21 (2H, d, J=8.5Hz), 8.25 (2H, d, J=8.5Hz) ppm

REFERENCE EXAMPLE 9-11

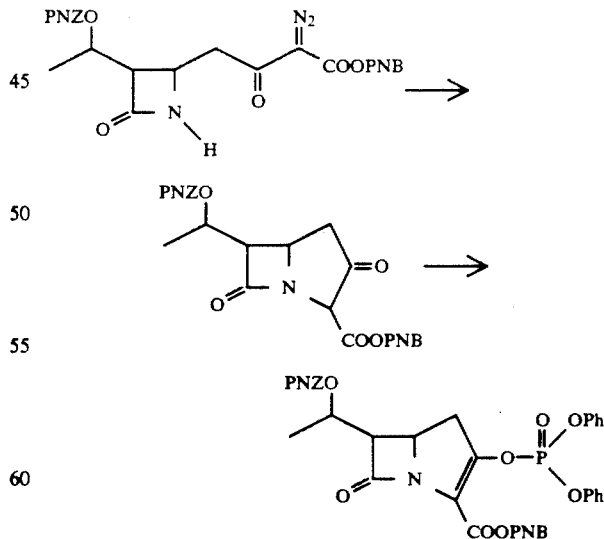

a) 0.55 g of 3-(1-p-nitrobenzyloxycarbonyloxyethyl)-4-[3-(p-nitrobenzyloxycarbonyl)-2-oxo-3-diazopropyl]-2-azetidinone was dissolved in 25 ml of degassed dried benzene, and a catalytic amount of rhodium (II) acetate was added thereto. After blowing nitrogen gas into the mixture for about 3 minutes, the mixture was refluxed for 20 minutes, followed by cooling. The catalyst was separated by filtration and washed with benzene. The filtrate and the washing were combined and concentrated under reduced pressure to yield p-nitrobenzyl-6-(1-p-nitrobenzyloxycarbonyloxyethyl)-1-azabicyclo[3.2.0]heptan-3,7-dione-2-carboxylate.

IR$_{max}^{neat}$ (cm$^{-1}$): 1770, 1745, 1520, 1350, 1260

NMR δ (CDCl$_3$): 1.50 (3H, d, J=6.5Hz), 2.50 (1H, dd, J=8.0 and 18Hz), 2.89 (1H, dd, J=7.0 and 18Hz), 3.39 (1H, dd, J=2.0 and 8.0Hz), 4.14 (1H, dt, J=2.0 and 7.0Hz), 4.77 (1H, s), 5.26 (4H, s), 7.52 (4H, d, J=8.5Hz), 8.21 (4H, d, J=8.5Hz) ppm b) The keto ester derivative as obtained in a) above was dissolved in 25 ml of dried acetonitrile, and 195 mg of diisopropylethylamine was added thereto under ice-cooling. To the resulting mixture was added dropwise a solution of 300 mg of diphenyl chlorophosphate in 2 ml of dried acetonitrile, followed by stirring for 1 hour. The reaction mixture was diluted with ethyl acetate, washed with water, and dried over magnesium sulfate. The solvent was removed by distillation under reduced pressure to obtain p-nitrobenzyl-5,6-trans-3-(diphenylphosphoryloxy)-6-(1-p-nitrobenzyloxycarbonyloxyethyl)-1-azabicyclo[3.2.0]hept-2-ene-7-one-2-carboxylate.

IR$_{max}^{neat}$ (cm$^{-1}$): 1780, 1745, 1585, 1517, 1480, 1345, 1295, 1255, 1180, 1158, 965

NMR δ (CDCl$_3$): 1.46 (3H, d, J=6.5Hz), 3.24 (2H, br. d, J=8.5Hz), 3.40 (1H, dd, J=3.0 and 8.5Hz), 5.24 (2H, s), 5.32 (2H, ABq, J=13Hz), 7.28 (10H, s), 7.53 (4H, d, J=8.5Hz), 8.14 (2H, d, J=8.5Hz), 8.23 (2H, d, J=8.5Hz) ppm Further, by using (3R,4S)-1-(di-p-anisylmethyl)-3-ethenyl-4-carboxy-2-azetidinone [optical rotation [α]$_D^{22}$= +63.3° (c=0.12, CHCl$_3$)], (5R,6S,8R)-p-nitrobenzyl-3-(diphenylphosphorylxy)-6-(1-p-nitrobenzyloxycarbonyloxyethyl)-1-azabicyclo [3.2.0]hept-2-ene-7-one-2-carboxylate was obtained.

REFERENCE EXAMPLE 10-1

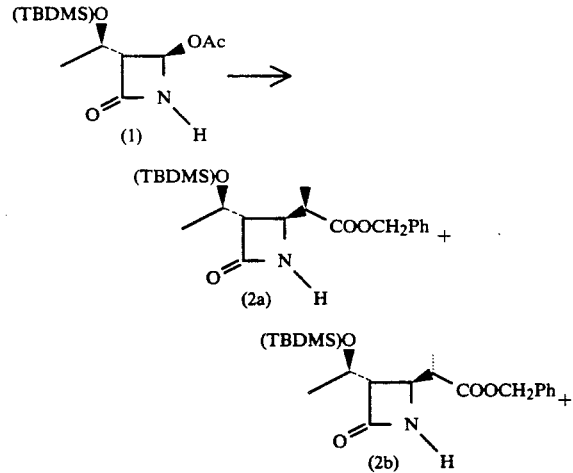

To 1.33 g (20 mM) of activated zinc was added 20 ml of dried tetrahydrofuran, and 8.8 ml of a 15% n-hexane solution of diethylaluminium chloride was added thereto in a nitrogen stream under ice-cooling. A solution prepared by dissolving 1.49 g (5.2 mM) of (3R,4R)-4-acetoxy-3-[(R)-1-(t-butyldimethylsilyloxy)ethyl]-2-azetidinone (1) and 3.73 g (15.3 mM) of benzyl α-bromopropionate in 13.3 ml of dried tetrahydrofuran was added dropwise to the mixture over a period of 30 to 40 minutes, followed by stirring for 1 hours. Under ice-cooling, 2.8 ml of pyridine, 13.2 ml of water, 26.5 ml of ethyl acetate and 13.2 ml of a 1N hydrochloric acid aqueous solution were successively added thereto, and the resulting mixture was filtered using Celite. The filtrate was washed with water, and the organic layer was dried over sodium sulfate and distilled off to remove the solvent. The resulting oily residue was subjected to silica gel column chromatography to obtain an isomeric mixture of 4-(1-benzyloxycarbonyl)-ethyl-3-[(R)-1-(t-butyldimethylsilyloxy)ethyl]-2-azetidinone.

The isomeric mixture was separated into each compound by Lober column chromatography using silica gel and 1.5% isopropanol/n-hexane as an eluent to obtain the compound (2a) and the compound (2b) as oily substances.

Isomer (2b)

IR$_{max}^{neat}$ (cm$^{-1}$): 1755, 1460, 1377, 1252, 1100, 835

NMR δ (CDCl$_3$): 0.06 (6H, s), 0.87 (9H, s), 1.16 (3H, d, J=6.5Hz), 1.19 (3H, d, J=7.0Hz), 3.71 (1H, dd, J=2 and 10Hz), 5.14 (2H, s), 7.35 (5H, s) ppm Isomer (2a)

NMR δ (CDCl$_3$): 0.06 (6H, s), 0.87 (9H, s), 1.08 (3H, d, J=6.5Hz), 1.18 (3H, d, J=7.0Hz), 3.91 (1H, dd, J=2.2 and 5.5Hz), 4.17 (2H, q, J=6Hz), 5.12 (2H, s), 7.35 (5H, s) ppm

REFERENCE EXAMPLE 10-2

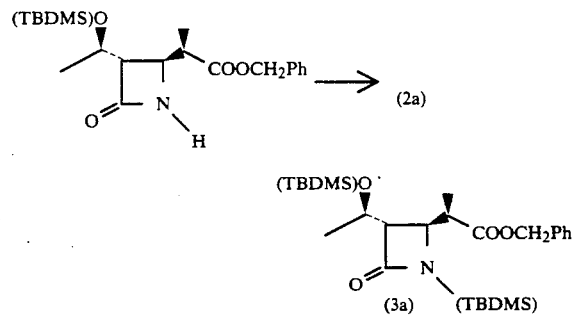

200 mg of 4-(1-benzyloxycarbonyl)ethyl-3-(R)-1-(t-butyl-dimethylsilyloxy)ethyl]-2-azetidinone (2a) was dissolved in 2 ml of dried dimethylformamide. 126 mg of triethylamine was added to the resulting solution, and then 151 mg of t-butyldimethylsilyl chloride was added thereto, followed by stirring at room temperature overnight. The reaction mixture was diluted with ethyl acetate, washed with water, dried over sodium sulfate and purified by silica gel chromatography to obtain 4-(1-benzyloxycarbonyl)ethyl-3-[(R)-1-(t-butyldimethylsilyloxy)ethyl]-1-(t-butyldimethylsilyl)-2-azetidinone (3a).

IR$_{max}^{neat}$ (cm$^{-1}$): 1750, 1465, 1325, 1255, 835

REFERENCE EXAMPLE 10-3

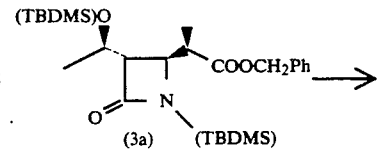

-continued

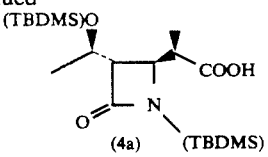

184 mg of 4-(1-benzyloxycarbonyl)ethyl-3-[(R)-1-(t-butyldimethylsilyloxy)ethyl]-1-(t-butyldimethylsilyl)-2-azetidinone (3a) was dissolved in 4 ml of methanol, and the resulting solution was stirred together with 20 mg of 10% palladium-on-carbon at an atmospheric pressure of hydrogen for 2 hours. The catalyst was removed by filtration, and the filtrate was concentrated under reduced pressure to obtain 4-(1-carboxy)ethyl-3-[(R)-1-(t-butyldimethylsilyloxy)-ethyl]-1-(t-butyldimethylsilyl)-2-azetidinone (4a).

$IR_{max}^{neat}$ (cm$^{-1}$): 1740, 1465, 1330, 1255, 1043, 837

REFERENCE EXAMPLE 10-4

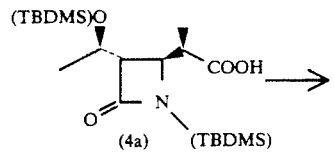

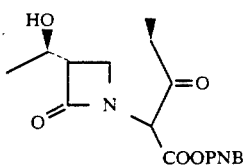

(4R,5R,6S,8R)-p-Nitrobenzyl-4-methyl-6-(1-hydroxyethyl)-1-azabicyclo[3.2.0]-hept-3,7-dione-2-carboxylate was obtained from 170 mg of 4-(1-carboxy)-ethyl-3[(R)-1-(t-butyldimethylsilyloxy)ethyl]-1-(t-butyldimethylsilyl-2-azetidinone (4a) according to the method described in Japanese Patent Application OPI No. 26887/83, pages 64–65.

$IR_{max}^{neat}$ (cm$^{-1}$): 3450 (br.), 1770 (sh.), 1750, 1605, 1520, 1350, 1217, 1180

REFERENCE EXAMPLE 11

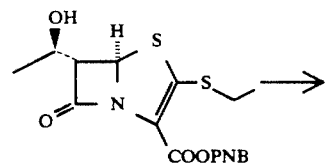

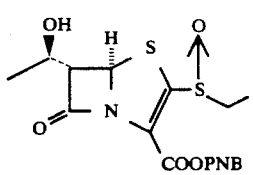

To a solution of 261 mg of (5R,6S,8R)-p-nitrobenzyl-3-ethylthio-6-(1-hydroxyethyl)-1-azabicyclo[3.2.0]hept-2-ene-7-one-4-thia-2-carboxylate in 28 ml of dried methylene chloride, 144 mg of m-chloroperbenzoic acid was added at −45° C. in a nitrogen stream, followed by stirring at −20° to −40° C. for 2 hours. The reaction mixture was washed with a saturated aqueos solution of sodium bicarbonate and then with water, dried over sodium sulfate and distilled off to remove the solvent. The resulting residue was purified by silica gel chromatography to obtain (5R,6S,8R)-p-nitrobenzyl-3-ethylsulfinyl-6-(1-hydroxyethyl)-1-azabicyclo[3.2.0]hept-2-ene-7-one-4-thia-2-carboxylate.

IR $\nu_{max}^{CHCl_3}$ (cm$^{-1}$): 1793, 1703, 1605, 1517, 1447, 1377, 1344, 1315, 1172, 1112, 1043, 965, 824

NMR δ (CDCl$_3$): 5.74 (3/5H, d, J=1.5Hz), 5.87 (2/5H, d, J=1.5Hz) ppm

EXAMPLE 1—1

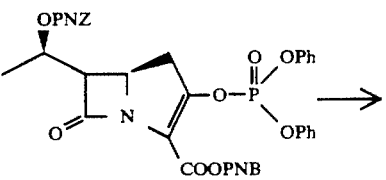

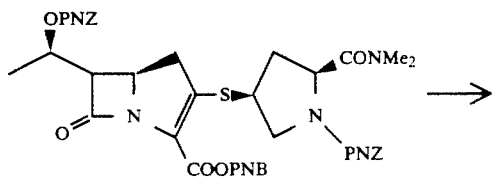

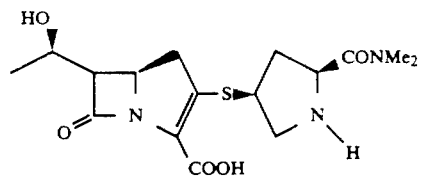

a) 122 mg of (5R,6S,8R)-p-nitrobenzyl-3-(diphenylphosphoryloxy-6-(1-p-nitrobenzyloxycarbonyloxyethyl)-1-azabicyclo[3,2,0]-hept-2-ene-7-one-2-carboxylate was dissolved in 3 ml of dry acetonitrile, and 31 mg of diisopropylethylamine was added thereto in a nitrogen stream under ice-cooling. Then, 60 mg of [2S,4S]-1-p-nitrobenzyloxycarbonyl-2-dimethylaminecarbonyl-4-mercaptopyrrolidine was added to the mixture, followed by stirring for 1 hour. The reaction solution was diluted with ethyl acetate, washed with water, dried over magnesium sulfate and the solvent was distilled off. The residue was purified by silica gel thin layer chromatography to obtain 95 mg of (5R,6S,8R,2'S,4'S)-p-nitrobenzyl-3-[4-(1-p-nitrobenzyloxycarbonyl-2-dimethylaminecarbonyl)pyrrolidinylthio]-6-(1-p-nitrobenzyloxycarbonyloxyethyl)-1-azabicyclo[3,2,0]-hept-2-ene-7-one-2-carboxylate.

$IR_{max}^{neat}$ (cm$^{-1}$): 1780, 1745, 1705, 1650, 1605, 1515, 1342, 1257

NMR δ(CDCl$_3$): 1.49 (3H, d, J=6Hz), 2.99 (3H, s), 3.11 (3H, s), 5.25 (4H, s), 5.23 and 5.46 (2H, ABq, J=14Hz), 7.53 (4H, d, J=8.5Hz), 7.62 (2H, d, J=8.5Hz), 8.18 (6H, d, J=8.5Hz)

$[\alpha]_D^{28}$ +7.7° (c=0.303, acetone)

b) 95 mg of (5R,6S,8R,2'S,4'S)-p-nitrobenzyl-3-[4-(1-p-nitrobenzyloxycarbonyl-2-dimethylaminecarbonyl)pyrrolidinylthio]-6-(1-p-nitrobenzyloxycarbonyloxyethyl-1-azabicyclo[3,2,0]-hept-2-ene-7-one-2-carboxylate was dissolved in 20 ml of dioxane, and a morpholinopropanesulfonic acid buffer solution (pH=7.0, 10 ml) and platinum oxide (35 mg) were added thereto.

The mixture was then hydrogenated under a hydrogen pressure of 3.5 atm. for 6.5 hours. The catalyst was filtered off and dioxane was distilled off under reduced pressure. The residual solution was washed with ethyl acetate, and the aqueous layer was again distilled under reduced pressure to remove the organic solvent. The residual solution was subjected to polymer chromatography (CHP-20P) to obtain (5R,6S, 8R,2′S,4′S)-3-[4-(2-dimethylaminecarbonyl)pyrrolidinylthio]-6-(1-hydroxyethyl)-1-azabicyclo[3,2,0]hept-2-ene-7-one-2-carboxylic acid from the fraction eluted with water.

UV$_{max}^{H2O}$ nm: 297

IR$_{max}^{KBr}$ cm$^{-1}$: 1755, 1627, 1393, 1252, 1130

NMR δ(D$_2$O): 1.25 (3H, d, J=6.4Hz), 1.81-1.96 (1H, m), 2.96 (3H, s), 3.03 (3H, s), 3.14-3.20 (3H, m), 3.31-3.41 (2H, m), 3.62-3.72 (1H, m), 3.90-4.00 (1H, m), 4.14-4.26 (2H, m), 4.63 (1H, t, J=8.5Hz)

EXAMPLE 1-2

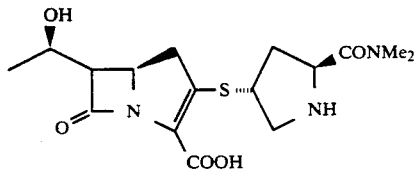

a) In the same manner as described in Example 1-1(a) but using 129 mg of (5R,6S,8R)-p-nitrobenzyl-3-(diphenylphosphoryloxy)-6-(1-p-nitrobenzyloxycarbonyloxyethyl)-1-azabicyclo[3,2,0]hept-2-ene-7-one-2-carboxylate and 67 mg of [2S,4R]-1-p-nitrobenzyloxycarbonyl-2-dimethylaminecarbonyl-4-mercaptopyrrolidine, there was obtained mg of (5R,6S,8R,2′S,4′R)-p-nitrobenzyl-3-[4-(1-p-nitrobenzyloxycarbonyl-2-dimethylaminecarbonyl)pyrrolidinylthio]-6-(1-p-nitrobenzyloxycarbonyloxyethyl)-1-azabicyclo[3,2,0-]hept-2-ene-7-one-carboxylate.

IR$_{max}^{neat}$ (cm$^{-1}$): 1775, 1745, 1705, 1650, 1520, 1400, 1345, 1260, 1130

NMR δ(CDCl$_3$): 1.48 (3H, d, J=6Hz), 2.96 (3H, s), 3.12 (3H, s), 5.22 (4H, s), 7.44, 7.50 and 7.58 (each 2H, d, J=8.5Hz), 8.17 (6H, d, J=8.5Hz)

[α]$_D^{27}$ +31.1° (c=0.193, acetone)

b) In the same manner as described in Example 1-1(b) but using 40 mg of (5R,6S,8R,2′S,4′R)-p-nitrobenzyl-3-[4-(1-p-nitrobenzyloxycarbonyl-2-dimethylaminecarbonyl)-6-(1-p-nitrobenzyloxycarbonyloxyethyl)-1-azabicyclo[3,2,0]hept-2-ene-7-one-2-carboxylate, there was obtained (5R,6S,8R,2′S,4′R)-3-[4-(2-dimethylaminecarbonyl)pyrrolidinylthio]-6-(1-hydroxyethyl)-1-azabicyclo[3,2,0]hept-2-ene-7-one-2-carboxylic acid.

UV$_{max}^{H2O}$ nm: 297

EXAMPLE 1-3

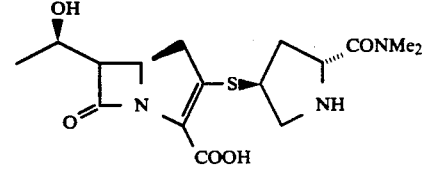

a) In the same manner as described in Example 1-1(a) but using 61 mg of (5R,6S,8R)-p-nitrobenzyl-3-(diphenyl- phosphoryloxy)-6-(1-p-nitrobenzyloxycarbonyloxyethyl)-1-azabicyclo[3,2,0]hept-2-ene-7-one-2-carboxylate and 31 mg of [2R,4S]-1-p-nitrobenzyloxycarbonyl-2-dimethylamine carbonyl-4-mercaptopyrrolidine, there was obtained 37 mg of (5R,6S,8R,2′R,4′S)-p-nitrobenzyl-3-[4-(1-p-nitrobenzyloxycarbonyl-2-dimethylaminecarbonyl)pyrrolidinylthio]-6-(1-p-nitrobenzyloxycarbonyloxyethyl)-1-azabicyclo[3,2,0]hept-2-ene-7-one-2-carboxylate.

IR$_{max}^{neat}$ (cm$^{-1}$): 1775, 1745, 1705,1650, 1520, 1400, 1345, 1260, 1130

NMR δ(CDCl$_3$): 1.49 (3H, d, J=6.5Hz), 2.98 (3H, s), 3.16 (3H, s), 5.27 (4H, s), 5.19 and 5.47 (2H, ABq, J=14Hz), 7.50, 7.55 and 7.64 (each 2H, d, J=8.5Hz), 8.20 (4H, d, J=8.5Hz), 8.22 (2H, d, J=8.5Hz)

[α]$_D^{29}$ +26.8° (c=0.243, acetone)

b) In the same manner as described in Example 1-1(b) but using 37 mg of (5R,6S,8R,2′R,4′S)-p-nitrobenzyl-3-[4-(1-p-nitrobenzyloxycarbonyl-2-dimethylaminecarbonyl)pyrrolidinylthio]-6-(1-p-nitrobenzyloxycarbonyloxyethyl)-1-azabicyclo[3,2,0]hept-2-ene-7-one-2-carboxylate, there was obtained (5R,6S,8R,2′R,4′)-3-[4-(2-dimethylaminecarbonyl)pyrrolidinylthio]-6-(1-hydroxyethyl)-1-azabicyclo[3,2,0]hept-2-ene-7-one-2-carboxylic acid.

UV$_{max}^{H2O}$ nm: 297

EXAMPLE 1-4

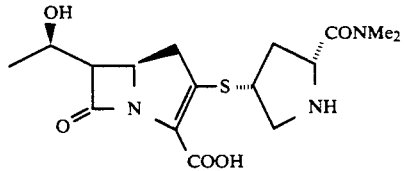

a) In the same manner as described in Example 1-1(a) but using 76 mg of (5R,6S,8R)-p-nitrobenzyl-3-(diphenylphosphoryloxy)-6-(1-p-nitrobenzyloxycarbonyloxyethyl)-1-azabicyclo[3,2,0]-hept-2-ene-7-one-2-carboxylate and 39 mg of [2R,4R]-1-p-nitrobenzyloxycarbonyl-2-dimethylaminecarbonyl-4-mercaptopyrrolidine, there was obtained 35 mg of (5R,6S,8R,2′R,4′R)-p-nitrobenzyl-3-[4-(1-p-nitrobenzyloxycarbonyl-2-dimethylaminecarbonyl)pyrrolidinylthio]-6-(1-p-nitrobenzyloxycarbonyloxyethyl)-1-azabicyclo[3,2,0-]hept-2-ene-7-one-2-carboxylate.

IR$_{max}^{neat}$ (cm$^{-1}$): 1775, 1745, 1705, 1650, 1520, 1440, 1342, 1260, 1120

NMR δ(CDCl$_3$): 1.49 (3H, d, J=6.5Hz), 2.98 (3H, s), 3.09 (3H, s), 5.25 (4H, s), 5.26 and 5.44 (2H, ABq, J=14Hz), 8.20 (6H, d, J=8.5Hz)

[α]$_D^{30}$ +23.3° (c=0.329, acetone)

b) In the same manner as described in Example 1—1(b) but using 35 mg of (5R,6S,8R,2′R,4′R)-p-nitrobenzyl-3-[4-(1-p-nitrobenzyloxycarbonyl-2-dimethylaminecarbonyl)-pyrrolidinylthio]-6-(1-p-nitrobenzyloxycarbonyloxyethyl)-1-azabicyclo[3,2,0]hept-2-ene-7-one-2-carboxylate, there was obtained (5R,6S,8R,2′R,4′R)-3-[4-(2-dimethylaminecarbonyl)-pyrrolidinylthio]-6-(1-hydroxyethyl)-1-azabicyclo[3,2,0]hept-2-ene-7-one-2-carboxylic acid.

UV$_{max}^{H2O}$ nm: 297

EXAMPLE 2

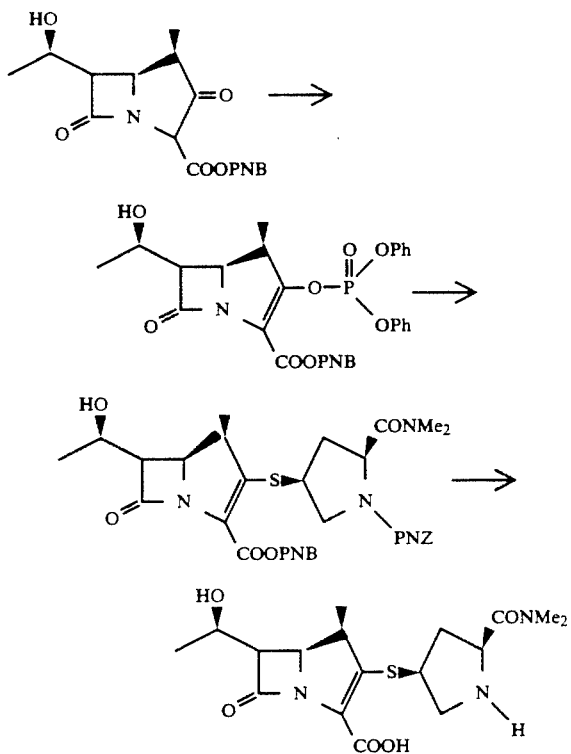

a) 53 mg of (4R,5R,6S,8R)-p-nitrobenzyl-4-methyl-6-(1-hydroxyethyl)-1-azabicyclo[3,2,0]-hept-3,7-dione-2-carboxylate was dissolved in 5 ml of dry acetonitrile, and 57 mg of diisopropylethylamine and then 43 mg of diphenyl chlorophosphate were added thereto. After stirring for 2.5 hours, 57 mg of [2S,4S]-1-p-nitrobenzyloxycarbonyl-2-dimethyl-aminocarbonyl-4-mercaptopyrrolidine was added to the mixture, followed by stirring for 1 hour. The reaction solution was diluted with ethyl acetate, washed with water, dried over magnesium sulfate and the solvent was distilled off. The residue was purified by silica gel thin layer chromatography to obtain 35 mg of (4R,5R,6S, 8R,2′S,4′S)-p-nitrobenzyl-3-[4-(1-p-nitrobenzyloxycarbonyl-2-dimethylaminecarbonyl)pyrrolidinylthio]-4-methyl-6-(1-hydroxyethyl)-1-azabicyclo[3,2,0]-hept-2-ene-7-one-2-carboxylate.

IR$_{max}^{neat}$ (cm$^{-1}$): 1760, 1705, 1645, 1520, 1402, 1342, 1135, 1110

NMR δ(CDCl₃): 1.30 (3H, d, J=7.0Hz), 1.35 (3H, d, J=6.5Hz), 2.99 (3H, s), 3.02 (3H, d, J=15Hz), 5.21 (2H, s), 5.20 and 5.43 (2H, ABq, J=14Hz), 7.51 (2H, d, J=8.5Hz), 7.64 (2H, d, J=8.5Hz), 8.20 (4H, d, J=8.5Hz)

b) 25 mg of (4R,5R,6S,8R,2′S,4′S)-p-nitrobenzyl-3-[4-(1-p-nitrobenzyloxycarbonyl-2-dimethylaminecarbonyl)pyrrolidinylthio]-4-methyl-6-(1-hydroxyethyl)-1-azabicyclo[3,2,0]hept-2-ene-7-one-2-carboxylate was dissolved in a mixture of 1.9 ml of tetrahydrofuran and 0.3 ml of ethanol, and the mixture was hydrogenated in a morpholinopropanesulfonic acid buffer solution (pH=7.0, 1.9 ml) under atmospheric pressure of hydrogen for 3 hours at room temperature in the presence of 30 mg of 10% palladium-carbon, which had been activated in hydrogen atmosphere for 1 hour followed by washing with water. After filtering off the catalyst, tetrahydrofuran and ethanol were distilled off under reduced pressure, and the residual solution was washed with ethyl acetate. The aqueous layer was again distilled under reduced pressure to remove organic solvents, and the residual solution was subjected to polymer chromatography (CHP-20P) to obtain (4R,5R,6S,8R,2′S,4′)-3-[4-(2-dimethylaminecarbonyl)pyrrolidinylthio]-4-methyl-6-(1-hydroxyethyl)-1-azabicyclo[3,2,0]hept-2-ene-7-one-2-carboxylic acid from the fraction eluted with water.

UV$_{max}^{H2O}$ nm: 296

NMR δ(D₂O): 1.21 (3H, d, J=7.0Hz), 1.29 (3H, d, J=6.5Hz), 1.92 (1H, m), 2.99 (3H, s), 3.06 (3H, s)

EXAMPLE 3

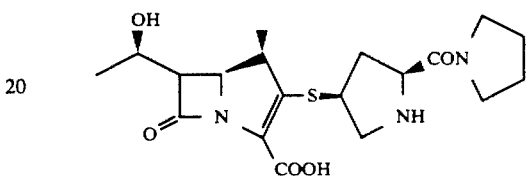

a) 61 mg of (4R,5R,6S,8R)-p-nitrobenzyl-4-methyl-6-(1-hydroxyethyl)-1-azabicyclo[3,2,0]-hept-3,7-dione-2-carboxylate was dissolved in 6 ml of dry acetonitrile, and 72 mg of diiropropylethylamine and then 55 mg of diphenyl chlorophosphate were added thereto in a nitrogen stream under ice-cooling, followed by stirring for 2.5 hours. 77 mg of [2S,4S]-1-p-nitrobenzyloxycarbonyl-2-(1-pyrrolidinecarbonyl)-4-mercaptopyrrolidine was added to the mixture, followed by stirring for 1 hour. The reaction solution was diluted with ethyl acetate, washed with water, dried over magnesium sulfate, and the solvent was distilled off. The residue was purified by silica gel thin layer chromatography to obtain 51 mg of (4R,5R, 6S,8R,2′S,4′S)-p-nitrobenzyl-3-[(1-p-nitrobenzyloxycarbonyl-2-(1-pyrrolidinecarbonyl)pyrrolidin-4-ylthio]-4-methyl-6-(1-hydroxyethyl)-1-azabicyclo[3,2,0]-hept-2-ene-7-one-2-carboxylate.

IR$_{max}^{neat}$ (cm$^{-1}$): 1760, 1710, 1640, 1525, 1440, 1350, 1210, 1110

NMR δ(CDCl): 1.30 (3H, d, J=7.0Hz), 1.34 (3H, d, J=6.5Hz), 5.21 (2H, s), 5.20 and 5.44 (2H, ABq, J=14Hz), 7.50 (2H, d, J=8.5Hz), 7.64 (2H, d, J=8.5Hz), 8.20 (4H, d, J=8.5Hz)

b) 50 mg of (4R,5R,6S,8R,2′S,4′S)-p-nitrobenzyl-3-[1-p-nitrobenzyloxycarbonyl-2-(1-pyrrolidinecarbonyl)-pyrrolidin-4-ylthio]-4-methyl-6-(1-hydroxyethyl)-1-[3,2,0]-hept-2-ene-7-one-2-carboxylate was dissolved in a mixture of 3.9 ml of tetrahydrofuran and 0.6 ml of ethanol, and the mixture was hydrogenated in a morpholinopropanesulfonic acid buffer solution (pH=7.0, 3.9 ml) under atmospheric pressure of hydrogen for 4.5 hours at room temperature in the presence of 60 mg of 10% palladium-carbon, which had been activated in hydrogen atmosphere for 1 hour followed by washing with water. After filtering off the catalyst, tetrahydrofuran and ethanol were distilled off under reduced pressure, and the residual solution was washed with ethyl acetate. The aqueous layer was again distilled under reduced pressure to remove organic solvents, and the residual solution was subjected to polymer chromatography (CHP-20P) to obtain (4R,5R,6 S,8R,2′S,4′S)-3-[2-(1-pyrrolidinecarbonyl)pyrrolidin-4-ylthio]-4-methyl-6-(1-hydroxyethyl)-1-azabicyclo[3,2,0]-hept-2-ene-7-one-2-carboxylic acid from the fraction eluted with a 2% aqueous tetrahydrofuran solution.

UV$_{max}^{H2O}$ nm: 297

NMR δ(D20): 1.20 (3H, d, J=7.0Hz), 1.28 (3H, d, J=6.5Hz), 1.95 (6H, m), 3.46 (6H, m), 3.72 (1H, dd, J=6.5 and 12Hz), 4.02 (1H quintet, J=6.5Hz)

EXAMPLE 4

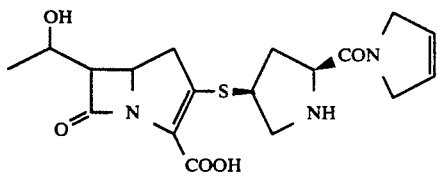

a) 172 mg of (5R,6S,8R)-p-nitrobenzyl-3-(diphenylphosphoryloxy)-6-(1-p-nitrobenzyloxycarbonyloxyethyl)-1-azabicyclo[3,2,0]-hept-2-ene-7-one-2-carboxylate was dissolved in 2.3 ml of dry acetonitrile, and to the solution were added a solution of 59 mg of diisopropylethylamine in 0.7 ml of dry acetonitrile and then a solution of 94 mg of [2S,4S]-1-p-nitrobenzyloxycarbonyl-2-(3-pyrroline-1-carbonyl)-4-mercaptopyrrolidine in 1 ml of dry acetonitrile, in a nitrogen stream and under ice-cooling, followed by stirring for 15 minutes. The reaction solution was diluted with diethyl ether, washed with water, and the insoluble material in the ether layer was dissolved with addition of methylene chloride. The methylene chloride and ether layer was dried over magnesium sulfate and the solvent was distilled off. The residue was purified by silica gel thin layer chromatography to obtain 182 mg of (5R,6S,8R,-2'S,4'S)-p-nitrobenzyl-3-{4-[1-p-nitrobenzyloxycarbonyl-2-(3-pyrroline-1-carbonyl)]-pyrrolidinylthio}-6-(1-p-nitrobenzyloxycarbonyloxyethyl)-1-azabicyclo[3,2,0]-hept-2-ene-7-one-2-carboxylate.

IR$_{max}^{CHCl3}$ (cm$^{-1}$): 1780, 1745, 1708, 1660, 1623, 1606, 1520, 1342

NMR δ(CDCl$_3$): 1.49 (3H, d, J=6.2Hz), 5.26 (4H, s), 8.18 (6H, d, J=8.8Hz)

b) 182 mg of (5R,6S,8R,2'S,4'S)-p-nitrobenzyl-3-{4-[1-p-nitrobenzyloxycarbonyl-2-(3-pyrroline-1-carbonyl)]pyrrolidinylthio}-6-(1-p-nitrobenzyloxycarbonyloxyethyl)-1-azabicyclo[3,2,0]-hept-2-ene-7-one-2-carboxylate was dissolved in a mixture of 12.6 ml of tetrahydrofuran and 2 ml of ethanol, and the solution was hydrogenated in a morpholinopropanesulfonic acid buffer solution (pH=7.0, 12.6 ml) at room temperature under atmospheric pressure of hydrogen for 7 hours in the presence of 219 mg of 10% palladium-carbon, which had been activated in hydrogen atmosphere for 1 hour, followed by washing with water. After filtering off the catalyst, tetrahydrofuran and ethanol were distilled off under reduced pressure, and the residual solution was washed with ethyl acetate. The aqueous layer was again distilled under reduced pressure to remove organic solvents, and the residual solution was subjected to polymer chromatography (CHP-20P) to obtain (5R,6S,8R,2'S,4'S)-3-{4-[2-(3-pyrroline-1-carbonyl)pyrrolidinylthio}-6-(1-hydroxyethyl)-1-azabicyclo[3,2,0]hept-2-ene-7-one-2-carboxylic acid from the fraction eluted with a 2% aqueous tetrahydrofuran solution.

UV λ$_{max}^{H2O}$ nm: 298

IR$_{max}^{KBr}$ (cm$^{-1}$): 1755, 1640, 1595, 1450, 1380, 1245

NMR δ (D$_2$O): 1.26 (3H, d, J=6.4Hz), 3.18 (1H, dd, J=2.1 and 9.0Hz), 3.77 (1H, dd, J=7.0 and 12.0Hz), 5.89 (2H, br. s)

EXAMPLE 5

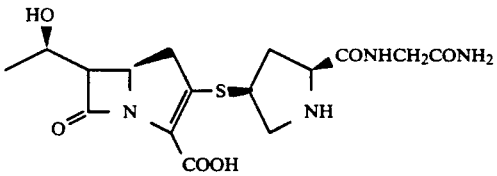

a) Following the procedures as described in Example 1—1(a) using 68 mg of (5R,6S,8R)-p-nitrobenzyl-3-(diphenylphosphoryloxy)-6-(1-p-nitrobenzyloxycarbonyloxyethyl)-1-azabicyclo[3,2,0]hept-2-ene-7-one-2-carboxylate and 33 mg of [2S,4S]-1-p-nitrobenzyloxycarbonyl-2-carbamoylmethylaminecarbonyl-4-mercaptopyrrolidine, there was obtained 61 mg of crystalline (5R,6S,8R,2'S, 4'S)-p-nitrobenzyl-3-[4-(1-p-nitrobenzyloxycarbonyl-2-carbamoylmethylaminecarbonyl)pyrrolidinylthio]-6-(1-p-nitrobenzyloxycarbonyloxyethyl)-1-azabicyclo[3,2,0]hept-2-ene-7-one-2-carboxylate by filtration.

IR$_{max}^{Nujol}$(cm$^{-1}$): 3445, 3300, 1790, 1745, 1710, 1670, 1635, 1510, 1345, 1270

NMR δ(CDCl$_3$): 1.50 (3H, d, J=6.5Hz), 5.23 (4H, s), 7.50 (4H, d, J=8.5Hz), 8.21 (6H, d, J=8.5Hz)

m.p.: 184°–189° C. (dec.)

b) 30 mg of (5R,6S,8R,2'S,4'S)-p-nitrobenzyl-3-[4-(1-p-nitrobenzyloxycarbonyl-2-carbamoylmethylaminecarbonyl)pyrrolidinylthio]-6-(1-p-nitrobenzyloxycarbonyloxyethyl)-1-azabicyclo[3,2,0]hept-2-ene-7-one-2-carboxylate was dissolved in a mixture of 3.1 ml of tetrahydrofuran and 1 ml of dimethylformamide, and the solution was hydrogenated in the presence of a morpholinopropanesulfonic acid buffer solution (pH=7.0, 3.1 ml) at room temperature under atmospheric pressure of hydrogen for 5 hours in the presence of 37 mg of 10% palladium-carbon which had been activated in hydrogen atmosphere for 1 hour followed by washing with water. After filtering off the catalyst, tetrahydrofuran was distilled off under reduced pressure, and the residual solution was washed with methylene chloride. The aqueous layer was distilled to remove the organic solvents, and the residual solution was subjected to polymer chromatography (CHP-20P) to obtain (5R,6S,8R,2'S,4'S)-3-[4-(2-carbamoylmethylaminecarbonyl)pyrrolidinylthio]-6-(1-hydroxyethyl)-1-azabicyclo[3,2,0]hept-2-ene-7-one-2-carboxylic acid from the fraction eluted with water.

UV λ$_{max}^{HO}$ nm: 300

IR$_{max}^{KBr}$(cm$^{-1}$): 1745, 1665, 1590, 1390, 1220, 1180, 1040

NMR δ(D$_2$O) 1.26 (3H, d, J=6.6Hz), 1.86 (1H, m), 3.20 (2H, dd, J=7.5 and 14.7Hz), 3.38 (1H, dd, J=3.0 and 6.7Hz), 4.02 (1H, t, J=9.0Hz)

EXAMPLE 6

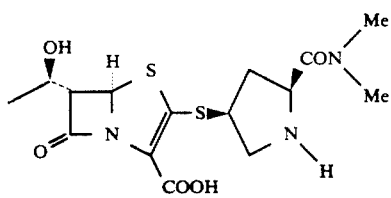

a) To a solution of 45 mg of (5R,6S,8R)-p-nitrobenzyl-3-ethylsulfinyl-6-(1-hydroxyethyl)-1-azabicyclo[3,2,0]hept-2-ene-7-one-4-thia-2-carboxylate in 0.8 ml of dry acetonitrile were added a solution of 30 mg of diisopropylethylamine in 0.3 ml of dry acetonitrile and then a solution of 81 mg of (2'S,4'S)-1'-p-nitrobenzyloxycarbonyl-2-dimethylaminecarbonyl-4'-mercaptopyrrolidine in 0.6 ml of dry acetonitrile under nitrogen stream at +40° C., followed by stirring the mixture at −40° C. to −45° C. for 10 minutes. The reaction solution was diluted with ethyl acetate, washed with a saturated aqueous solution of sodium chloride, dried over sodium sulfate, and the solvent was distilled off. The resulting residue was purified by silica gel chromatography to obtain (5R,6S, 8R,2'S,4'S)-p-nitrobenzyl-3-[(1-p-nitrobenzyloxycarbonyl-2-dimethylaminecarbonyl)pyrrolidin-4-ylthio]-6-(1-hydroxyethyl)-1-azabicyclo[3,2,0]hept-2-ene-7-one-4-thia-2-carboxylate.

$[\alpha]_D^{29}$ +52° (c=0.43, CHCl$_3$)

IR $\lambda_{max}^{CHCl3}$ (cm$^{-1}$): 1788, 1700, 1660, 1607, 1400, 1325, 1114, 1013

NMR δ(CDCl$_3$): 1.32 (3H, d, J=6Hz), 2.96 (3H, s), 3.08 (3H, s), 3.72 (1H, dd, J=1.5Hz and J=6Hz), 5.20 (2H, s), 5.70 (1H, d, J=1.5Hz)

b) 204 mg of 5% palladium-carbon was suspended in a mixture of ethanol (3.8 ml) and water (3.8 ml) and hydrogenated at room temperature under atmospheric pressure for 1 hour. The catalyst was filtered, washed with water, suspended in a phosphate buffer (pH=6.86, 5.1 ml), and added to a solution of 68 mg of (5R,6S,8R, 2'S,4'S)-p-nitrobenzyl-3-[(1-p-nitrobenzyloxycarbonyl-2-dimethylaminecarbonyl)pyrrolidin-4-ylthio]-6-(1-hydroxyethyl)-1-azabicyclo]3,2,0]hept-2-ene-7-one-4-thia-2-carboxylate in 7.7 ml of tetrahydrofuran. The mixture was hydrogenated at room temperature and under atmospheric pressure for 3 hours. After filtering off the catalyst, tetrahydrofuran was distilled off under reduced pressure. The residual solution was washed with ethyl acetate, and the aqueous layer was again distilled under reduced pressure to remove the organic solvents. The resulting residual solution was purified by CHP-20P column chromatography to obtain (5R,6S,8R,2'S,4'S)-2-[(2-dimethylaminecarbonyl)pyrrolidin-4-ylthio]-6-(1-hydroxyethyl)-1-azabicyclo[3,2,0-]hept-2-ene-7-one-4-thia-2-carboxylic acid.

UV $\lambda_{max}^{H2O}$ nm: 322, 255

IR $\lambda_{max}^{KBr}$ (cm$^{-1}$): 1765, 1645, 1580, 1508, 1367

NMR δ(D2O) 1.29 (3H, d, J=6.4Hz), 1.94–2.08 (1H, m), 2.93–3.15 (1H, m), 2.98 (3H, s), 3.05 (3H, s), 3.53–3.62 (1H, m), 3.83–3.93 (1H, m), 3.94 (1H, dd, J=1.4Hz and J=6Hz), 4.06–4.30 (3H, m), 5.71 (1H, d, J=1.4Hz)

EXAMPLES 7 TO 90

The compounds shown in Table 6 below were prepared from the corresponding mercaptan derivatives. In Table 6, "HE" represents (R)-1-hydroxyethyl group, and "PNZE" represents (R)-1-p-nitrobenzyloxycarbonyloxyethyl group.

TABLE 6

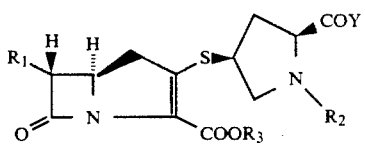

| Example No. | R$_1$ | R$_2$ | R$_3$ | Y | | Spectral Data |
|---|---|---|---|---|---|---|
| 7 | PNZE | PNZ | PNB | —N(H)(H) | IR$\nu_{max}^{Nujol}$ (cm$^{-1}$): | 3420, 1785, 1742, 1710, 1677, 1510, 1342, 1255 m.p. 138–142° C. |
| | | | | | $[\alpha]_D^{30}$ +44.4° | (c=0.105, DMF) |
| | | | | | UV$\lambda_{max}^{H2O}$ nm: | 297 |
| | HE | H | H | —N(H)(H) | IR$\nu_{max}^{KBr}$ (cm$^{-1}$): NMRδ (D$_2$O): | 1752, 1687, 1595, 1385 1.24(3H, d, J=6.5Hz), 2.0–2.15(1H, m), 2.83–2.98(1H, m), 3.17(2H, d, J=9Hz), 3.32–3.42(2H, m), 3.71–3.80(1H, m), 3.98(1H, quintet; J=7Hz), 4.13–4.32(1H, m), 4.41(1H, t, J=8.5Hz) |
| | | | | | $[\alpha]_D^{30}$ −25° | (c=0.05, H$_2$O) |
| 8 | PNZE | PNZ | PNB | —N(CH$_3$)(H) | IR$\nu_{max}^{neat}$ (cm$^{-1}$): NMRδ (CDCl$_3$): | 1775, 1745, 1700, 1665(sh), 1515, 1345, 1257 1.48(3H, d, J=6.5Hz), 2.73(3H, s), 3.21(2H, d, J=9Hz), 5.25(4H, s), 5.25 and 5.43(2H, ABq, J=14Hz), 7.50, 7.54 and 7.62(each 2H, d, J=8.5Hz), 8.20(6H, d, J=8.5Hz) |
| | HE | H | H | —N(CH$_3$)(H) | UV$\lambda_{max}^{H2O}$ nm: | 297 |

TABLE 6-continued

| | | | | Substituent | Spectral data | |
|---|---|---|---|---|---|---|
| 9 | PNZE | PNZ | PNB | −N(H)−CH(CH₃)CH₃ (isopropyl) | IR$\nu_{max}^{Nujol}$ (cm$^{-1}$): | 1770, 1740, 1700, 1510, 1340, 1255 |
| | | | | | NMRδ (CDCl₃): | 1.08(3H, d, J=6.5Hz), 1.11(3H, d, J=6.5Hz), 1.48(3H, d, J=6Hz), 3.18(2H, br.d, J=9Hz), 5.25(4H, s), 5.26 and 5.44(2H, ABq, J=14Hz), 7.50, 7.54 and 7.62(each 2H, J=9Hz), 8.20(6H, d, J=8.5Hz) |
| | HE | H | H | −N(H)−CH(CH₃)CH₃ | UVλ$_{max}^{H2O}$ nm: | 296 |
| 10 | PNZE | PNZ | PNB | −N(H)−CH₂CH=CH₂ | IR$\nu_{max}^{Nujol}$ (cm$^{-1}$): | 3275, 1782, 1740, 1700, 1650, 1515, 1340, 1260 |
| | | | | | NMRδ (CDCl₃): | 1.48(3H, d, J=6.5Hz), 3.18(2H, br, d, J=9Hz), 5.24(4H, s), 5.25 and 5.45(2H, ABq, J=14Hz), 7.50, 7.53 and 7.62(each 2H, d, J=8.5Hz), 8.19(6H, d, J=8.5Hz) |
| | HE | H | H | −N(H)−CH₂CH₂CH₃ | NMRδ (D₂O): | 1.0(3H, t, J=7.5Hz), 1.23(3H, d, J=7Hz) |
| | | | | | UVλ$_{max}^{H2O}$ nm: | 298 |
| | HE | H | H | −N(H)−CH₂CH=CH₂ | NMRδ (D₂O): | 1.27(3H, d, J=7Hz), 5.68(3H, m) |
| | | | | | UVλ$_{max}^{H2O}$ nm: | 298 |
| 11 | PNZE | PNZ | PNB | −N(C₂H₅)₂ | IR$\nu_{max}^{neat}$ (cm$^{-1}$): | 1780, 1750, 1710, 1650, 1525, 1440, 1350, 1262 |
| | | | | | NMRδ (CDCl₃): | 1.06(3H, t, J=7Hz), 1.27(3H, t, J=7Hz), 1.49(3H, d, J=6Hz), 5.24(4H, s), 5.25 and 5.46(2H, ABq, J=14Hz), 7.46, 7.50 and 7.63(each 2H, d, J=8.5Hz), 8.20(6H, d, J=8.5Hz) |
| | HE | H | H | −N(C₂H₅)₂ | UVλ$_{max}^{H2O}$ nm: | 299 |
| | | | | | IR$\nu_{max}^{CHCl3}$ (cm$^{-1}$): | 1780, 1746, 1708, 1656, 1610, 1525, 1350, 1260 |
| 12 | PNZE | PNZ | PNB | −N(CH₃)(n-C₄H₉) | NMRδ (CDCl₃): | 1.48(3H, d, J=6Hz), 5.27(4H, s), 8.20(6H, d, J=9Hz) |
| | | | | | UVλ$_{max}^{H2O}$ nm: | 297 |
| | HE | H | H | −N(CH₃)(n-C₄H₉) | IR$\nu_{max}^{KBr}$ (cm$^{-1}$): | 1755, 1635, 1590, 1370, 1240 |
| | | | | | NMRδ (D₂O): | 0.88(3H, t, J=7.1Hz), 1.26(3H, d, J=6.4Hz), 1.91(1H, m), 2.94 and 3.02(3H, s) |
| 13 | PNZE | H | PNB | −N(H)−CH₂Ph | IR$\nu_{max}^{Nujol}$ (cm$^{-1}$): | 1770, 1735, 1640, 1510, 1340, 1250 |
| | | | | | NMRδ (CDCl₃): | 1.49(3H, d, J=6.5Hz), 4.42(2H, d, J=7.0Hz), 5.25(4H, s), 5.27 and 5.43(2H, ABq, J=14Hz), 7.27(5H, s), 7.54, 7.62, 8.21 and 8.22(each 2H, d, J=8.5Hz) |
| | HE | H | H | −N(H)−CH₂Ph | UVλ$_{max}^{H2O}$ nm: | 297 |
| 14 | PNZE | PNZ | PNB | −N(CH₂Ph)(CH₃) | IR$\nu_{max}^{neat}$ (cm$^{-1}$): | 1780, 1750, 1715, 1660, 1525, 1442, 1350, 1265, 1122 |
| | | | | | NMRδ (CDCl₃): | 1.48(3H, d, J=6.5Hz), 2.92(3H, s), 4.56(2H, d, J=5Hz), 5.25(4H, s), 8.19(6H, d, J=9Hz) |
| | HE | H | H | −N(CH₂Ph)(CH₃) | UVλ$_{max}^{H2O}$ nm: | 297 |
| 15 | PNZE | PNZ | PNB | −N(H)−CH₂−(2-pyridyl) | IR$\nu_{max}^{Nujol}$ (cm$^{-1}$): | 1790, 1745, 1714, 1652, 1605, 1520, 1347 |
| | | | | | | m.p. 179–182° C. (dec.) |
| | | | | | UVλ$_{max}^{H2O}$ nm: | 299, 266, 260 |

TABLE 6-continued

| | | | | | | |
|---|---|---|---|---|---|---|
| | HE | H | H | —NH-CH₂-(2-pyridyl) 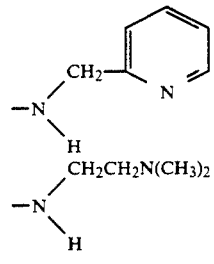 | IR$\nu_{max}^{KBr}$ (cm$^{-1}$): NMRδ (D₂O): | 1745, 1590, 1490, 1210, 1090, 910  1.26(3H, d, J=6.3Hz), 1.99(1H, m), 2.80(1H, m), 3.36(1H, dd, J=2.7 and 6.0Hz), 3.58(1H, dd, J=7.0 and 12.0Hz), 3.86(1H, m), 4.51(2H, d, J=4.4Hz), 7.82(1H, dt, J=1.8 and 7.7Hz), 8.42(1H, m) |
| 16 | PNZE | PNZ | PNB | —N(H)CH₂CH₂N(CH₃)₂ | IR$\nu_{max}^{neat}$ (cm$^{-1}$): NMRδ (CDCl₃): | 1775, 1745, 1700, 1660(sh), 1515, 1345, 1260  1.47(3H, d, J=6.5Hz), 2.24(3H, s), 2.27(3H, s), 5.25(4H, s), 7.49, 7.53 and 7.62(each 2H, d, J=8.5Hz), 8.20(6H, d, J=8.5Hz) |
| | HE | H | H | —N(H)CH₂CH₂N(CH₃)₂ | UVλ$_{max}^{H2O}$ nm: | 297 |
| 17 | PNZE | PNZ | PNB | —N(CH₃)CH₂CH₂N(CH₃)₂ | IR$\nu_{max}^{neat}$ (cm$^{-1}$): NMRδ (CDCl₃): | 1770, 1745, 1700, 1650, 1512, 1342, 1257  1.49(3H, d, J=6.0Hz), 2.24(3H, s), 2.30(6H, s), 5.25(4H, s), 5.27 and 5.45(2H, ABq, J=13.5Hz), 7.54(4H, d, J=8.5Hz), 7.63(2H, d, J=8.5Hz), 8.20(6H, d, J=8.5Hz) |
| | HE | H | H | —N(CH₃)CH₂CH₂N(CH₃)₂ | UVλ$_{max}^{H2O}$ nm: | 298 |
| 18 | PNZE | PNZ | PNB | —N(H)CH₂CH₂OH | IR$\nu_{max}^{neat}$ (cm$^{-1}$): NMRδ (CDCl₃): | 3350, 1770, 1740, 1695, 1510, 1340, 1250  1.48(3H, d, J=6Hz), 5.25(4H, s), 5.18 and 5.43(2H, ABq, J=14Hz), 7.49, 7.53 and 7.61(each 2H, d, J=8.5Hz), 8.18(6H, d, J=8.5Hz) |
| | HE | H | H | —N(H)CH₂CH₂OH | UVλ$_{max}^{H2O}$ nm: | 298 |
| 19 | PNZE | PNZ | PNB | —N(CH₃)CH₂CH₂OH | IR$\nu_{max}^{neat}$ (cm$^{-1}$): NMRδ (CDCl₃): | 3400, 1778, 1745, 1700, 1650, 1520, 1345, 1260, 1120  1.48(3H, d, J=6.5Hz), 3.00(3H, s), 5.20(2H, s), 5.25(2H, s), 5.25 and 5.45(2H, ABq, J=13.5Hz), 7.49, 7.51 and 7.63(each 2H, d, J=8.5Hz), 8.19(4H, d, J=8.5Hz), 8.21(2H, d, J=8.5Hz) |
| | HE | H | H | —N(CH₃)CH₂CH₂OH | UVλ$_{max}^{H2O}$ nm: | 297 |
| 20 | PNZE | PNZ | PNB | —N(H)CH₂CH₂CH₂COOPNB | IR$\nu_{max}^{neat}$ (cm$^{-1}$): NMRδ (CDCl₃): | 1770, 1730, 1695, 1650, 1600, 1505, 1340  1.48(3H, d, J=6.5Hz), 5.25(4H, s), 7.62(2H, d, J=8.6Hz), 8.20(6H, d, J=8.6Hz) |
| | HE | H | H | —N(H)CH₂CH₂CH₂COOH | UVλ$_{max}^{H2O}$ nm: | 297 |
| 21 | PNZE | PNZ | PNB | —N(H)CH₂CONHCH₃ | IR$\nu_{max}^{Nujol}$ (cm$^{-1}$): UVλ$_{max}^{H2O}$ nm: | 1795, 1747, 1712, 1640, 1608, 1517, 1350, 1275  m.p. 167–169° C. (dec.)  300 |
| | HE | H | H | —N(H)CH₂CONHCH₃ | IR$\nu_{max}^{KBr}$ (cm$^{-1}$): NMRδ (D₂O): | 1752, 1650, 1590, 1388, 1255, 1150  1.26(3H, d, J=6.3Hz), 2.71(3H, s), 2.93(1H, q, J=7.4Hz), 3.88(2H, s) |
| 22 | PNZE | PNZ | PNB | —N(H)CH₂CON(CH₃)₂ | IR$\nu_{max}^{Nujol}$ (cm$^{-1}$): UVλ$_{max}^{H2O}$ nm: | 1800, 1750, 1707, 1675, 1650, 1610, 1520, 1350, 1280  m.p. 196–199° C. (dec.)  299 |
| | HE | H | H | —N(H)CH₂CON(CH₃)₂ | IR$\nu_{max}^{KBr}$ (cm$^{-1}$): NMRδ (D₂O): | 1750, 1640, 1590, 1380, 1250, 1145  1.26(3H, d, J=6.3Hz), 2.92(3H, s), 3.03(3H, s), 3.19(2H, dd, J=6.3 and 9.2Hz), 3.51(1H, dd, J=7.4 and 12Hz), 4.12(2H, s) |

TABLE 6-continued

| | | | | | | |
|---|---|---|---|---|---|---|
| 23 | PNZE | PNZ | PNB | $-N\begin{smallmatrix}CHCONH_2\\|\\CH_3\end{smallmatrix}$ H | IR$\nu_{max}^{Nujol}$ (cm$^{-1}$): | 1795, 1750, 1700, 1680, 1655, 1610, 1525, 1350 m.p. 168–170° C. (dec.) |
| | HE | H | H | $-N\begin{smallmatrix}CHCONH_2\\|\\CH_3\end{smallmatrix}$ H | IR$\nu_{max}^{KBr}$ (cm$^{-1}$): UV$\lambda_{max}^{H2O}$ nm: | 1745, 1665, 1590, 1390, 1180, 1037 300 |
| 24 | PNZE | PNZ | PNB | $-N\begin{smallmatrix}CH-CONHCH_3\\|\\CH_3\end{smallmatrix}$ H | IR$\nu_{max}^{Nujol}$ (cm$^{-1}$): UV$\lambda_{max}^{H2O}$ nm: | 1790, 1752, 1710, 1650, 1610, 1525, 1350 m.p. 98–101° C. 301 |
| | HE | H | H | $-N\begin{smallmatrix}CH-CONHCH_3\\|\\CH_3\end{smallmatrix}$ H | IR$\nu_{max}^{KBr}$ (cm$^{-1}$): NMR$\delta$ (D$_2$O): | 1750, 1650, 1590, 1385, 1170, 1040 1.26(3H, d, J=6.6Hz), 1.36(3H, d, J=8.1Hz), 2.71(3H, s), 3.19(1H, dd, J=6.6 and 9.0Hz), 3.98(1H, t, J=8.0Hz) |
| 25 | PNZE | PNZ | PNB | $-N\begin{smallmatrix}CH-CON(CH_3)_2\\|\\CH_3\end{smallmatrix}$ H | IR$\nu_{max}^{neat}$ (cm$^{-1}$): NMR$\delta$ (D$_6$-DMCO): | 1780, 1745, 1705, 1640, 1605, 1520, 1346 m.p. 172–175° C. 1.12(3H, d, J=7Hz), 1.34(3H, d, J=6.4Hz), 2.79(3H, s), 2.94(3H, s), 5.30(2H, s), 8.20(6H, d, J=8.8Hz) |
| | HE | H | H | $-N\begin{smallmatrix}CH-CON(CH_3)_2\\|\\CH_3\end{smallmatrix}$ H | UV$\lambda_{max}^{H2O}$ nm: IR$\nu_{max}^{KBr}$ (cm$^{-1}$): NMR$\delta$ (D$_2$O): | 300 1755, 1630, 1590, 1390, 1250, 1120 1.26(3H, d, J=6.3Hz), 1.31(3H, d, J=6.9Hz), 2.92(3H, s), 3.13(3H, s) |
| 26 | PNZE | PNZ | PNB | $-N\begin{smallmatrix}CH_2CONH_2\\ \\CH_3\end{smallmatrix}$ | IR$\nu_{max}^{CHCl_3}$ (cm$^{-1}$): NMR$\delta$ (CDCl$_3$): | 1783, 1746, 1705, 1680, 1608, 1524, 1345 1.48(3H, d, J=6.4Hz), 3.19(3H, s), 5.17(2H, s), 5.24(2H, s), 8.19(6H, d, J=8.6Hz) |
| | HE | H | H | $-N\begin{smallmatrix}CH_2CONH_2\\ \\CH_3\end{smallmatrix}$ | UV$\lambda_{max}^{H2O}$ nm: IR$\nu_{max}^{KBr}$ (cm$^{-1}$): NMR$\delta$ (D$_2$O): | 300 1750, 1654, 1590, 1395, 1250, 1060 1.26(3H, d, J=6.3Hz), 2.95(3H, s), 3.21(2H, dd, J=2.2 and 9.0Hz), 3.38(1H, dd, J=2.2 and 5.5Hz) |
| 27 | PNZE | PNZ | PNB | $-N\begin{smallmatrix}CH_2CONHCH_3\\ \\CH_3\end{smallmatrix}$ | IR$\nu_{max}^{CHCl_3}$ (cm$^{-1}$): NMR$\delta$ (CDCl$_3$): | 1778, 1743, 1685, 1660, 1605, 1520, 1340 1.48(3H, d, J=6.2Hz), 2.72(3H, d, J=5Hz), 3.19(3H, s), 5.22(2H, s), 5.25(2H, s), 8.22(6H, d, J=8.8Hz) |
| | HE | H | H | $-N\begin{smallmatrix}CH_2CONHCH_3\\ \\CH_3\end{smallmatrix}$ | UV$\lambda_{max}^{H2O}$ nm: IR$\nu_{max}^{KBr}$ (cm$^{-1}$): NMR$\delta$ (D$_2$O): | 300 1750, 1640, 1585, 1382, 1250, 1125 1.26(3H, d, J=6.3Hz), 2.73(3H, s), 3.09(3H, s), 3.39(1H, q, J=2.6Hz) |
| 28 | PNZE | PNZ | PNB | $-N\begin{smallmatrix}CH_2CON(CH_3)_2\\ \\CH_3\end{smallmatrix}$ | IR$\nu_{max}^{neat}$ (cm$^{-1}$): NMR$\delta$ (CDCl$_3$): | 1778, 1745, 1705, 1650, 1605, 1520, 1345 1.49(3H, d, J=6.2Hz), 2.93(3H, s), 2.99(3H, s), 3.10 and 3.15(3H, s), 5.25(4H, s), 8.21(6H, d, J=8.4Hz) |
| | HE | H | H | $-N\begin{smallmatrix}CH_2CON(CH_3)_2\\ \\CH_3\end{smallmatrix}$ | UV$\lambda_{max}^{H2O}$ nm: IR$\nu_{max}^{KBr}$ (cm$^{-1}$): | 297 1760, 1650, 1500, 1380, 1240, 1130 |
| 29 | PNZE | PNZ | PNB | $-N\diagup\!\!\diagdown N-CH_3$ | IR$\nu_{max}^{neat}$ (cm$^{-1}$): NMR$\delta$ (CDCl$_3$): | 1778, 1750, 1705, 1650, 1518, 1430, 1345, 1258 1.49(3H, d, J=6.5Hz), 2.25(3H, s), 2.31(4H, s), 5.25(4H, s), 5.21 and 5.46(2H, ABq, J=13.5Hz), 7.53(4H, d, J=8.5Hz), 7.62(2H, d, J=8.5Hz), 8.20(6H, d, J=8.5Hz) |
| | HE | H | H | $-N\diagup\!\!\diagdown N-CH_3$ | UV$\lambda_{max}^{H2O}$ nm: | 298 |

TABLE 6-continued

| | | | | | | |
|---|---|---|---|---|---|---|
| 30 | PNZE | PNZ | PNB | −N⟨morpholine⟩ | $IR\nu_{max}^{neat}$ (cm$^{-1}$): | 1780, 1750, 1710, 1655, 1520, 1350, 1255, 1115 |
| | | | | | NMRδ (CDCl$_3$): | 1.48(3H, d, J=6.5Hz), 3.58 and 3.67(each 4H, s), 5.25(4H, s), 5.26 and 5.45(2H, ABq, J=14Hz), 7.53(4H, d, J=9Hz), 7.62(2H, d, J=9Hz), 8.19(6H, d, J=9Hz) |
| | HE | H | H | −N⟨morpholine⟩ | UVλ$_{max}^{H2O}$ nm: | 298 |
| 31 | PNZE | PNZ | PNB | −N⟨thiomorpholine⟩ | $IR\nu_{max}^{CHCl_3}$ (cm$^{-1}$): | 1780, 1740, 1705, 1655, 1610, 1520, 1345 |
| | | | | | NMRδ (CDC$_3$): | 1.47(3H, d, J=6Hz), 5.22(4H, s), 8.13(6H, d, J=8Hz) |
| | HE | H | H | −N⟨thiomorpholine⟩ | UVλ$_{max}^{H2O}$ nm: | 298 |
| | | | | | $IR\nu_{max}^{KBr}$ (cm$^{-1}$): | 1750, 1625, 1595, 1396, 1248, 1090 |
| 32 | PNZE | PNZ | PNB | −NH−(4-pyridyl) | $IR\nu_{max}^{neat}$ (cm$^{-1}$): | 1780, 1740, 1700, 1590, 1520, 1340, 1255 |
| | | | | | NMRδ (CDCl$_3$): | 1.49(3H, d, J=6.6Hz), 5.26(4H, s), 5.35(2H, ABq, J=14.5Hz), 7.46(2H, d, J=5.5Hz), 8.48(2H, d, J=5.5Hz) |
| | HE | H | H | −NH−(4-pyridyl) | UVλ$_{max}^{H2O}$ nm: | 245, 300 |
| | | | | | IRν (cm$^{-1}$): | 1745, 1690, 1590, 1507, 1383, 1285 |
| 33 | PNZE | PNZ | PNB | −NH−(2-pyridyl) | $IR\nu_{max}^{Nujol}$ (cm$^{-1}$): | 1785, 1745, 1705, 1605, 1520, 1350 m.p. 181-183° C. (dec.) |
| | | | | | UVλ$_{max}^{H2O}$ nm: | 296, 276, 231 |
| | HE | H | H | −NH−(2-pyridyl) | $IR\nu_{max}^{KBr}$ (cm$^{-1}$): | 1750, 1690, 1595, 1435, 1385, 1240, 1090 |
| | | | | | NMRδ (D$_2$O): | 1.26(3H, d, J=6.3Hz), 1.95(1H, m), 3.20(1H, dd, J=4.0 and 9.0Hz), 3.37(1H, dd, J=2.6 and 6.1Hz), 8.32(1H, dd, J=1.3 and 5.0Hz), 8.60(1H, d, J=2.2Hz) |
| 34 | PNZE | PNZ | PNB | −NH−(3-pyridyl) | $IR\nu_{max}^{Nujol}$ (cm$^{-1}$): | 1790, 1745, 1705, 1670, 1605, 1515, 1345 m.p. 189-191° C. (dec.) |
| | | | | | UVλ$_{max}^{H2O}$ nm: | 298, 286, 237 |
| | HE | H | H | −NH−(3-pyridyl) | $IR\nu_{max}^{KBr}$ (cm$^{-1}$): | 1750, 1680, 1590, 1480, 1390, 1245, 1090 |
| | | | | | NMRδ (D$_2$O): | 1.26(3H, d, J=6.3Hz), 1.95(1H, m), 3.20(1H, dd, J=4.0 and 9.0Hz), 3.37(1H, dd, J=2.6 and 6.1Hz), 8.32(1H, dd, J=1.3 and 4.9Hz), 8.60(1H, d, J=2.2Hz) |
| 35 | PNZE | PNZ | PNB | −N⟨piperidine⟩ | $IR\nu_{max}^{neat}$ (cm$^{-1}$): | 1775, 1750, 1705, 1640, 1520, 1345, 1255, 1110 |
| | | | | | NMRδ (CDCl$_3$): | 1.48(3H, d, J=6.5Hz), 5.24(4H, s), 5.23 and 5.44(2H, ABq, J=14Hz), 8.19(6H, d, J=8.5Hz) |
| | HE | H | H | −N⟨piperidine⟩ | UVλ$_{max}^{H2O}$ nm: | 297 |
| 36 | PNZE | PNZ | PNB | −N⟨azetidine⟩ | $IR\nu_{max}^{neat}$ (cm$^{-1}$): | 1782, 1750, 1710, 1660, 1522, 1445, 1355, 1270, 1140 |
| | | | | | NMRδ (CDC$_3$): | 1.48(3H, d, J=6Hz), 5.26(4H, s), 5.18 and 5.42(2H, ABq, J=14Hz), 7.50(2H, d, J=8.5Hz), 7.53(2H, d, J=8.5Hz), 7.62(2H, d, J=8.5Hz), 8.19(6H, d, J=8.5Hz) |
| | HE | H | H | −N⟨azetidine⟩ | UVλ$_{max}^{H2O}$ nm: | 298 |
| | | | | | $IR\nu_{max}^{KBr}$ (cm$^{-1}$): | 1755, 1630, 1600, 1440, 1382, 1240 |
| | | | | | NMRδ (D$_2$O): | 1.26(3H, d, J=6.3Hz), 2.34(2H, m), 3.36(1H, dd, J=3.4 and 5.5Hz), 3.84(1H, m) |

TABLE 6-continued

| | | | | | | |
|---|---|---|---|---|---|---|
| 37 | PNZE | PNZ | PNB |  | IR$\nu_{max}^{CHCl_3}$ (cm$^{-1}$): | 1780, 1740(sh), 1710, 1605, 1520, 1340 |
| | | | | | NMRδ (CDCl$_3$): | 1.48(3H, d, J=6.4Hz), 5.25(4H, s), 6.32(2H, d, J=2Hz), 8.16(6H, d, J=8.8Hz) |
| | | | | | UVλ$_{max}^{H_2O}$ nm: | 297, 241 |
| | HE | H | H |  | IR$\nu_{max}^{KBr}$ (cm$^{-1}$): | 1750, 1720, 1590, 1470, 1390, 1280 |
| | | | | | NMRδ (D$_2$O): | 1.26(3H, d, J=6.2Hz), 2.12(2H, m), 6.44(2H, t, J=2.2Hz), 7.39(2H, t, J=2.2Hz) |
| 38 | PNZE | PNZ | PNB |  | IR$\nu_{max}^{CHCl_3}$ (cm$^{-1}$): | 1780, 1750, 1700, 1650(sh), 1610, 1525, 1350 |
| | | | | | NMRδ (CDCl$_3$): | 1.47(3H, d, J=6Hz), 5.22(4H, s), 8.12(6H, d, J=8.5Hz) |
| | HE | H | H |  | UVλ$_{max}^{H_2O}$ nm: | 298 |
| | | | | | IR$\nu_{max}^{KBr}$ (cm$^{-1}$): | 1750, 1650, 1600, 1440, 1395 |
| 39 | PNZE | PNZ | PNB |  | IR$\nu_{max}^{CHCl_3}$ (cm$^{-1}$): | 1783, 1750, 1715, 1660, 1615, 1530, 1350 |
| | | | | | NMRδ (CDCl$_3$): | 1.48(3H, d, J=5.9Hz), 5.25(4H, s), 8.15(6H, d, J=8.6Hz) |
| | | | | | UVλ$_{max}^{H_2O}$ nm: | 298 |
| | HE | H | H |  | IR$\nu_{max}^{KBr}$ (cm$^{-1}$): | 1750, 1630, 1590, 1460, 1380, 1240, 1090 |
| | | | | | NMRδ (D$_2$O): | 1.27(3H, d, J=6.3Hz), 3.19(1H, dd, J=2.9 and 9.2Hz), 3.39(1H, dd, J=2.6 and 6.0Hz) |
| 40 | PNZE | PNZ | PNB |  | IR$\nu_{max}^{CHCl_3}$ (cm$^{-1}$): | 1780, 1740, 1708, 1640, 1605, 1520, 1345 |
| | | | | | NMRδ (CDCl$_3$): | 1.50(3H, d, J=6.2Hz), 5.28(4H, s), 8.19(6H, d, J=8.1Hz) |
| | | | | | UVλ$_{max}^{H_2O}$ nm: | 297 |
| | HE | H | H |  | IR$\nu_{max}^{KBr}$ (cm$^{-1}$): | 1760, 1635, 1600, 1450, 1380 |
| | | | | | NMRδ (D$_2$O): | 1.27(3H, d, J=6.3Hz), 3.19(1H, dd, J=2.9 and 9.1Hz), 3.39(1H, dd, J=2.7 and 6.0Hz), 3.55(2H, d, J=4.0Hz), 3.69(1H, dd, J=2.0 and 4.3Hz) |
| 41 | PNZE | PNZ | PNB |  | IR$\nu_{max}^{CHCl_3}$ (cm$^{-1}$): | 1780, 1750, 1705, 1635, 1605, 1520, 1345 |
| | | | | | NMRδ (CDCl$_3$): | 1.49(3H, d, J=6.4Hz), 5.26(4H, s), 8.20(6H, d, J=8.8Hz) |
| | | | | | UVλ$_{max}^{H_2O}$ nm: | 298 |
| | HE | H | H |  | IR$\nu_{max}^{KBr}$ (cm$^{-1}$): | 1755, 1625, 1440, 1380, 1240 |
| | | | | | NMRδ (D$_2$O): | 1.23(3H, d, J=6.5Hz), 1.25(3H, d, J=6Hz), 1.31(3H, d, J=7Hz) |
| 42 | PNZE | PNZ | PNB |  | IR$\nu_{max}^{CHCl_3}$ (cm$^{-1}$): | 1785, 1746, 1705, 1657, 1610, 1525, 1345 |
| | | | | | NMRδ (CDCl$_3$): | 1.47(3H, d, J=6.2Hz), 5.25(4H, s), 8.16(6H, d, J=8.6Hz) |
| | | | | | UVλ$_{max}^{H_2O}$ nm: | 298 |
| | HE | H | H |  | IR$\nu_{max}^{KBr}$ (cm$^{-1}$): | 1750, 1655(sh), 1635, 1610(sh), 1380, 1220 |
| | | | | | NMRδ (D$_2$O): | 1.26(3H, d, J=6.3Hz) |
| 43 | PNZE | PNZ | PNB | 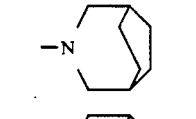 | IR$\nu_{max}^{CHCl_3}$ (cm$^{-1}$): | 1780, 1745, 1702, 1603, 1520, 1345 |
| | | | | | NMRδ (CDCl$_3$): | 1.48(3H, d, J=6Hz), 2.85(6H, s), 2.93(6H, s), 5.26(4H, s) |
| | | | | | UVλ$_{max}^{H_2O}$ nm: | 299, 229 |
| | HE | H | H | 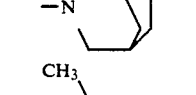 | IR$\nu_{max}^{KBr}$ (cm$^{-1}$): | 1750, 1690, 1590, 1420, 1285, 1130 |
| | | | | | NMRδ (D$_2$O): | 1.26(3H, d, J=6.3Hz), 1.91(1H, m), 2.60(1H, m), 3.08(6H, s), 3.16(6H, s), 3.40(1H, dd, J=2.7 and 6.0Hz), 4.37(1H, dd, J=6.0 and 9.5Hz) |

TABLE 6-continued

| | | | | | | |
|---|---|---|---|---|---|---|
| 44 | PNZE | PNZ | PNB | −N=C(NH₂)(NH₂) | IRν_max^CHCl3 (cm⁻¹): | 1780, 1740, 1705, 1605, 1523, 1345 |
| | | | | | NMRδ (CDCl₃): | 1.47(3H, d, J=6.8Hz), 5.25(4H, s) |
| | | | | | UVλ_max^H2O nm: | 207, 299 |
| | HE | H | H | −N=C(NH₂)(NH₂) | IRν_max^KBr (cm⁻¹): | 1750, 1640, 1590, 1545, 1385, 1040 |
| | | | | | NMRδ (D₂O): | 1.25(3H, d, J=6.6Hz), 1.85(1H, m) |
| 45 | PNZE | PNZ | PNB | −OPNB | IRν_max^neat (cm⁻¹): | 1775(sh), 1750, 1710, 1520, 1350, 1265 |
| | | | | | NMRδ (CDCl₃): | 1.48(3H, d, J=6.5Hz), 4.70(1H, dd, J=6 and 8.5Hz), 5.25(4H, s), 5.46(1H, d, J=14Hz), 7.53(4H, d, J=8.5Hz), 7.62(4H, d, J=8.5Hz), 8.18(4H, d, J=8.5Hz), 8.21(4H, d, J=8.5Hz) |
| | HE | H | H | −OH | UVλ_max^H2O nm: | 294 |
| 46 | | | | | IRν_max^CHCl3 (cm⁻¹): | 1787, 1753, 1716, 1614, 1530, 1431, 1410, 1355, 1268, 1138, 1116 |
| | PNZE | PNZ | PNB | −OCH₃ | NMRδ (CDCl₃): | 1.48(3H, d, J=6Hz), 1.83-2.42(1H, m), 2.50-3.02(1H, m), 3.17-4.53(8H, m), 3.70 and 3.73(3H, s), 5.02-5.28(2H, m), 5.27(4H, s), 5.47(1H, d, J=14Hz), 7.53(4H, d, J=9Hz), 7.63(2H, d, J=9Hz), 8.21(6H, d, J=9Hz) |
| | | | | | UVλ_max^H2O nm: | 300 |
| | HE | H | H | −OCH₃ | IRν_max^KBr (cm⁻¹): | 1735, 1595, 1488, 1388, 1245, 1090 |
| 47 | PNZE | PNZ | PNB | −NHNH₂ | IRν_max^Nujol (cm⁻¹): | 1782, 1750, 1705, 1620, 1520, 1350 m.p. 184-187° C. (dec.) |
| | HE | H | H | −NHNH₂ | UVλ_max^H2O nm: | 299 |
| | | | | | IRν_max^KBr (cm⁻¹): | 1750, 1720, 1590, 1390, 1245, 1120 |
| 48 | PNZE | PNZ | PNB | −NHN(CH₃)₂ | IRν_max^Nujol (cm⁻¹): | 1785, 1750, 1715, 1668, 1608, 1520, 1345 m.p. 187-189° C. (dec.) |
| | HE | H | H | −NHN(CH₃)₂ | UVλ_max^H2O nm: | 300 |
| | | | | | IRν_max^KBr (cm⁻¹): | 1750, 1690, 1595, 1390, 1175, 1020 |
| | | | | | NMRδ (D₂O): | 1.26(3H, d, J=6.4Hz), 2.60(6H, s), 3.18(1H, dd, J=6.0 and 9.1Hz), 3.39(1H, dd, J=2.6 and 6.0Hz) |
| 49 | PNZE | PNZ | PNB | −OC₂H₅ | IRν_max^CHCl3 (cm⁻¹): | 1784, 1750, 1714, 1608, 1524, 1432, 1404, 1378, 1348, 1265, 1197, 1132, 1113 |
| | | | | | NMRδ (CDCl₃): | 1.13-1.36(3H, m), 1.48(3H, d, J=6Hz), 1.83-2.36(1H, m), 2.56-3.06(1H, m), 3.19-4.59(10H, m), 4.89-5.36(2H, m), 5.27(4H, s), 5.47(1H, d, J=14Hz), 7.54(4H, d, J=8.5Hz), 7.63(2H, d, J=8.5Hz), 8.20(6H, d, J=8.5Hz) |
| | HE | H | H | −OC₂H₅ | UVλ_max^H2O nm: | 298 |
| | | | | | IRν_max^KBr (cm⁻¹): | 1743, 1597, 1380, 1240, 1130 |
| | | | | | NMRδ (D₂O): | 1.25(3H, d, J=6Hz), 1.27(3H, t, J=7Hz), 2.29(1H, m), 4.29(2H, q, J=7Hz) |
| 50 | PNZE | PNZ | PNB | −NHOPNB | IRν_max^Nujol (cm⁻¹): | 1790, 1750, 1715, 1670, 1602, 1515, 1340 m.p. 149-152° C. (dec.) |
| | HE | H | H | −NHOH | UVλ_max^H2O nm: | 300 |
| | | | | | IRν_max^KBr (cm⁻¹): | 1750, 1680, 1600, 1400, 1120 |
| 51 | PNZE | PNZ | PNB | −NHOCH₃ | IRν_max^Nujol (cm⁻¹): | 1787, 1745, 1710, 1665, 1605, 1520, 1345 m.p. 188-189.5° C. (dec.) |
| | HE | H | H | −NHOCH₃ | UVλ_max^H2O nm: | 299 |
| | | | | | IR_max^KBr (cm⁻¹): | 1745, 1680, 1600, 1440, 1390, 1245, 1050 |
| | | | | | NMRδ (D₂O): | 3.70(3H, s) |
| 52 | PNZE | PNZ | PNB | −N(CH₃)−N(CH₃)₂ | IRν_max^CHCl3 (cm⁻¹): | 1773, 1743, 1705, 1663, 1605, 1523, 1345, 1255 |
| | | | | | NMRδ (CDCl₃): | 1.49(3H, d, J=6.5Hz), 5.23(2H, s), 5.26(2H, s), 8.19(6H, d, J=8.8Hz) |
| | HE | H | H | −N(CH₃)−N(CH₃)₂ | UVλ_max^H2O nm: | 298 |
| | | | | | IRν_max^KBr (cm⁻¹): | 1763, 1660, 1590, 1380, 1240, 1060 |
| | | | | | NMRδ (D₂O): | 1.26(3H, d, J=6.6Hz), 2.50(3H, s), 2.52(3H, s), 2.92(3H, s), 3.18(2H, q, J=4.3Hz) |
| 53 | PNZE | PNZ | PNB | −N(aziridinyl) | IRν_max^neat (cm⁻¹): | 1780, 1750, 1710, 1605, 1525, 1350, 1260 |
| | | | | | NMRδ (CDCl₃): | 1.49(3H, d, J=6.4Hz), 5.25(4H, s), 5.36(2H, ABq, J=13.6Hz), 7.53(4H, d, J=8.8Hz), 7.62(2H, d, J=8.8Hz), 8.21(6H, d, J=8.8Hz) |

TABLE 6-continued

| | | | | | |
|---|---|---|---|---|---|
| | HE | H | H |  | UV$\lambda_{max}^{H2O}$ nm: 300<br>IR$\nu_{max}^{KBr}$ (cm$^{-1}$): 1735, 1595, 1396, 1255, 1215, 1043 |
| 54 | PNZE | PNZ | PNB | 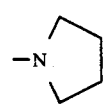 | IR$\nu_{max}^{neat}$ (cm$^{-1}$): 1780, 1745, 1705, 1645, 1520, 1440, 1350, 1262<br>NMR$\delta$ (CDCl$_3$): 1.49(3H, d, J=6.5Hz), 5.26(4H, s), 5.24 and 5.43(2H, ABq, J=14Hz), 7.44(2H, d, J=9Hz), 7.48(2H, d, J=9Hz), 7.68(2H, d, J=9Hz), 8.19(6H, d, J=9Hz) |
| | HE | H | H | 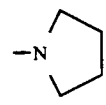 | UV$\lambda_{max}^{H2O}$ nm: 298<br>NMR $\delta$ (D$_2$O): 1.27(3H, d, J=6Hz), 1.83(4H, t, J=7Hz), 1.94–2.09(1H, m), 2.42(4H, t, J=7Hz), 2.77–2.92(1H, m), 3.11–3.42(5H, m), 3.81–3.99(1H, m), 4.14–4.29(2H, m) |

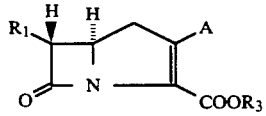

| Example No. | R$_1$ | R$_3$ | A | | Spectral Data |
|---|---|---|---|---|---|
| 55 | PNZE | PNZ | 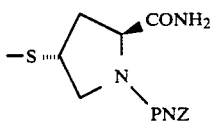 | IR$\nu_{max}^{neat}$ (cm$^{-1}$):<br>NMR$\delta$ (CDCl$_3$): | 1775, 1745, 1700, 1520, 1345, 1260, 1130<br>1.48(3H, d, J=6.5Hz), 3.22(2H, br, d, J=9.0Hz), 5.26(4H, s), 5.25 and 5.46(2H, ABq, J=14Hz), 7.50, 7.54 and 7.60(each 2H, d, J=9.0Hz), 8.18(4H, d, J=9.0Hz), 8.21(2H, d, J=9.0Hz) |
| | HE | H | 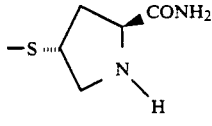 | $[\alpha]_D^{29}$ +37.3°<br>UV$\lambda_{max}^{H2O}$ nm: | (c=0.244, acetone)<br>298 |
| 56 | PNZE | PNZ | 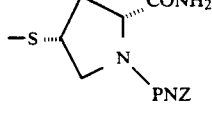 | IR$\nu_{max}^{neat}$ (cm$^{-1}$):<br>NMR$\delta$ (CDCl$_3$): | 1780, 1745, 1700, 1610, 1520, 1400, 1350, 1260, 1120<br>1.48(3H, d, J=6Hz), 3.19(2H, d. J=9Hz), 3.44(1H, dd, J=2.5 and 7.5Hz), 5.25(4H, s), 5.23 and 5.42(2H, ABq, J=14Hz), 7.47, 7.52 and 7.60(each 2H, d, J=8.5Hz), 8.16(4H, d, J=8.5Hz), 8.19(2H, d, J=8.5Hz) |
| | HE | H | 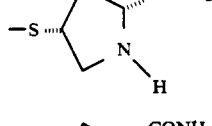 | $[\alpha]_D^{32}$ +57.6°<br>UV$\lambda_{max}^{H2O}$ nm: | (c=0.279, acetone)<br>297 |
| 57 | PNZE | PNB | 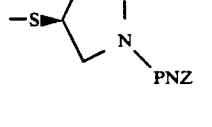 | IR$\nu_{max}^{neat}$ (cm$^{-1}$):<br>NMR$\delta$ (CDCl$_3$): | 1775, 1750, 1700, 1520, 1345, 1260, 1180<br>1.48(3H, d, J=6.5Hz), 3.26(2H, br, d, J=9.0Hz), 5.25(4H, s), 5.18 and 5.46(2H, ABq, J=14Hz), 7.49, 7.53 and 7.62(each 2H, d, J=8.5Hz), 8.17(4H, d, J=8.5Hz), 8.19(2H, d, J=8.5Hz) |
| | HE | H | 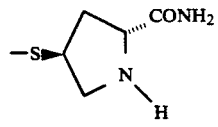 | $[\alpha]_D^{25}$ +43.7°<br>UV$\lambda_{max}^{H2O}$ nm: | (c=0.353, acetone)<br>297 |
| 58 | PNZE | PNB | 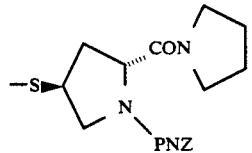 | IR$\nu_{max}^{CHCl3}$ (cm$^{-1}$): | 1750, 1705, 1645, 1610, 1525, 1440, 1350, 1265 |

TABLE 6-continued

| | HE | H | | UVλ$_{max}$$^{H2O}$ nm: | 287 |

| Example No. | R$_1$ | R$_2$ | R$_3$ | Y | | Spectral Data |
|---|---|---|---|---|---|---|
| 59 | HE | PNZ | PNB | —NH$_2$ | IRν$_{max}$$^{CHCl_3}$ (cm$^{-1}$): | 1775, 1700, 1607, 1520, 1395, 1345, 1105 |
| | | | | | NMRδ (CDCl$_3$): | 1.36(3H, d, J=6.0Hz), 1.37(3H, d, J=7.0Hz), 5.24(2H, s), 5.34(2H, ABq, J=13.5Hz), 7.50(2H, d, J=8.8Hz), 7.64(2H, d, J=8.8Hz), 8.22(4H, d, J=8.8Hz) |
| | HE | H | H | —NH$_2$ | UVλ$_{max}$$^{H2O}$ nm: | 295 |
| | | | | | IRν$_{max}$$^{KBr}$ (cm$^{-1}$): | 1750, 1660(sh), 1600, 1380, 1240 |
| 60 | HE | PNZ | PNB | N(Me)CH$_2$CH$_2$OH | IRν$_{max}$$^{CHCl_3}$ (cm$^{-1}$): | 1770, 1695, 1650, 1520, 1340 |
| | | | | | NMRδ (CDCl$_3$): | 1.34(3H, d, J=6.15Hz), 1.36(3H, d, J=8.0Hz), 3.00(3H, s), 5.20(2H, s), 5.36(2H, ABq, J=14.0Hz), 7.47(2H, d, J=8.8Hz), 7.64(2H, d, J=8.8Hz), 8.20(2H, d, J=8.8Hz) |
| | HE | H | H | N(Me)CH$_2$CH$_2$OH | UVλ$_{max}$$^{H2O}$ nm: | 289 |
| | | | | | IRν$_{max}$$^{KBr}$ (cm$^{-1}$): | 1750, 1630, 1605, 1375, 1240 |
| 61 | HE | PNZ | PNB | NHCH$_2$CONH$_2$ | IRν$_{max}$$^{CHCl_3}$ (cm$^{-1}$): | 3380, 1770, 1725(sh), 1700, 1680, 1605, 1520, 1342, 1250, 1102 |
| | | | | | NMRδ (CDCl$_3$): | 5.30(2H, s), 5.31(2H, ABq, J=13.8Hz), 7.48(2H, d, J=8.8Hz), 7.64(2H, d, J=8.8Hz), 8.21(4H, d, J=8.8Hz) |
| | HE | H | H | NHCH$_2$CONH$_2$ | UVλ$_{max}$$^{H2O}$ nm: | 295 |
| | | | | | IRν$_{max}$$^{KBr}$ (cm$^{-1}$): | 1750, 1670, 1600, 1390, 1245 |
| | | | | | NMRδ (D$_2$O): | 1.26(3H, d, J=6.5Hz), 1.28(3H, d, J=8Hz), 3.92(2H, s) |
| 62 | HE | PNZ | PNB | N(Me)CH$_2$CONH$_2$ | IRν$_{max}$$^{CHCl_3}$ (cm$^{-1}$): | 3480, 3350, 1773, 1678, 1604, 1525, 1345, 1310 |
| | | | | | NMRδ (CDCl$_3$): | 1.34(3H, d, J=6.2Hz), 1.37(3H, d, J=7.0Hz), 3.20(3H, s), 5.18(2H, s), 5.36(2H, ABq, J=13.4Hz), 7.46(2H, d, J=8.8Hz0, 7.63(2H, d, J=8.8Hz), 8.20(2H, d, J=8.8Hz), 8.21(2H, d, J=8.8Hz) |
| | HE | H | H | N(Me)CH$_2$CONH$_2$ | UVλ$_{max}$$^{H2O}$ nm: | 292 |
| | | | | | IRν$_{max}$$^{KBr}$ (cm$^{-1}$): | 1752, 1645, 1600, 1385, 1245 |
| 63 | HE | PNZ | PNB | —N(pyrrolinyl) | IRν$_{max}$$^{CHCl_3}$ (cm$^{-1}$): | 3420, 1772, 1705, 1660, 1623, 1606, 1526, 1440, 1345 |
| | | | | | [α]$_D$$^{25}$ −45° (c=0.11, CHCl$_3$) | |
| | | | | | NMRδ (CDCl$_3$): | 1.33(3H, d, J=6.15Hz), 1.37(3H, d, J=6.8Hz), 4.19(4H, br, s), 5.21(2H, s), 5.36(2H, ABq, J=13.9Hz), 5.84(2H, s), 7.40(2H, d, J=8.6Hz), 7.64(2H, d, J=8.6Hz), 8.14(2H, d, J=8.6Hz), 8.19(2H, d, J=8.6Hz) |
| | HE | H | H | —N(pyrrolinyl) | UVλ$_{max}$$^{H2O}$ nm: | 293 |
| | | | | | IRν$_{max}$$^{KBr}$ (cm$^{-1}$): | 1750, 1640, 1610, 1460, 1380 |
| | | | | | NMRδ (D$_2$O): | 1.25(3H, d, J=6Hz), 1.27(3H, d, J=7.5Hz), 5.85(2H, br. s) |
| 64 | HE | PNZ | PNB | —N(azetidinyl) | IRν$_{max}$$^{CHCl_3}$ (cm$^{-1}$): | 1770, 1702, 1650, 1520, 1343, 1102 |
| | | | | | NMRδ (CDCl$_3$): | 1.33(3H, d, J=6.15Hz), 1.37(3H, d, J=7.0Hz), 5.21(2H, s), 5.36(2H, ABq, J=13.9Hz), 7.50(2H, d, J=8.6Hz), 7.64(2H, d, J=8.6Hz), 8.20(4H, d, J=8.6Hz) |

TABLE 6-continued

| Example No. | R₁ | R₂ | R₃ | (substituent) | Spectral Data | |
|---|---|---|---|---|---|---|
| | HE | H | H | —N⟨azetidine⟩ | UV$\lambda_{max}^{H2O}$ nm:<br>IR$\nu_{max}^{KBr}$ (cm⁻¹):<br>NMRδ (D₂O): | 293<br>1755, 1630(sh), 1610, 1442, 1383, 1240, 1110<br>1.25(3H, d, J=6.5Hz), 1.28(3H, d, J=7Hz) |
| 65 | HE | PNZ | PNB | —N⟨pyrrolidine-OH⟩ | IR$\nu_{max}^{CHCl_3}$ (cm⁻¹):<br>NMRδ (CDCl₃): | 3400, 1770, 1705, 1650, 1520, 1432, 1345, 1107<br>1.35(3H, d, J=6.0Hz), 1.36(3H, d, J=7.0Hz), 5.20(2H, s), 5.36(2H, ABq, J=13.5Hz), 7.46(2H, d, J=8.8Hz), 7.64(2H, d, J=8.8Hz), 8.21(2H, d, J=8.8Hz) |
| | HE | H | H | —N⟨pyrrolidine-OH⟩ | UV$\lambda_{max}^{H2O}$ nm:<br>IR$\nu_{max}^{KBr}$ (cm⁻¹): | 293<br>1760, 1615, 1390, 1245, 1100 |
| 66 | HE | PNZ | PNB | —N⟨morpholine⟩ | IR$\nu_{max}^{CHCl_3}$ (cm⁻¹):<br>NMRδ (CDCl₃): | 1770, 1705, 1656, 1525, 1345, 1112<br>1.35(3H, d, J=6.15Hz), 1.36(3H, d, J=7.0Hz), 5.22(2H, s), 5.26(2H, ABq, J=13.9Hz), 7.50(2H, d, J=8.0Hz), 7.64(2H, d, J=8.0Hz), 8.20(4H, d, J=8.0Hz) |
| | HE | H | H | —N⟨morpholine⟩ | UV$\lambda_{max}^{H2O}$ nm:<br>IR$\nu_{max}^{KBr}$ (cm⁻¹): | 292<br>1760, 1630(sh), 1605, 1448, 1380, 1245, 1110 |
| 67 | HE | PNZ | PNB | —N⟨N-methylpiperazine⟩ | IR$\nu_{max}^{CHCl_3}$ (cm⁻¹):<br>NMRδ (CDCl₃): | 1772, 1710, 1650, 1520, 1435, 1400, 1340<br>1.34(3H, d, J=6.0Hz), 1.35(3H, d, J=7.5Hz), 2.25(3H, s), 2.31(4H, s), 5.22(2H, s), 5.36(2H, ABq, J=14.1Hz), 7.49(2H, d, J=8.6Hz), 7.63(2H, d, J=8.6Hz), 8.20(4H, d, J=8.6Hz) |
| | HE | H | H | —N⟨N-methylpiperazine⟩ | UV$\lambda_{max}^{H2O}$ nm:<br>IR$\nu_{max}^{KBr}$ (cm⁻¹): | 291<br>1755, 1620, 1442, 1380, 1250 |
| 68 | HE | PNZ | PNB | —OCH₃ | IR$\nu_{max}^{CHCl_3}$ (cm⁻¹):<br>NMRδ (CDCl₃): | 1775(sh), 1750(sh), 1710, 1605, 1522, 1345, 1107<br>1.35(3H, d, J=6.4Hz), 1.36(3H, d, J=6.8Hz), 3.66 and 3.73(3H, each s), 5.24(2H, s), 5.36(2H, ABq, J=13.2Hz), 7.45(2H, d, J=8.5Hz), 7.65(2H, d, J=8.5Hz), 8.22(4H, d, J=8.5Hz) |
| | HE | H | H | —OCH₃ | UV$\lambda_{max}^{H2O}$ nm:<br>IR$\nu_{max}^{KBr}$ (cm⁻¹): | 296<br>1735, 1602, 1390 |

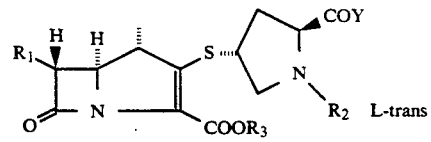

| Example No. | R₁ | R₂ | R₃ | Y | Spectral Data | |
|---|---|---|---|---|---|---|
| 69 | HE | PNZ | PNB | —N(CH₃)₂ | IR$\nu_{max}^{CHCl_3}$ (cm⁻¹):<br>[α]$_D^{25}$ −33°<br>NMRδ (CDCl₃): | 3400, 1770, 1708, 1652, 1604, 1523, 1397, 1342<br>(c=0.10, CHCl₃)<br>1.34(3H, d, J=6.15Hz), 1.39(3H, J=7.0Hz), 2.97(3H, s), 2.91 and 3.12(3H, s), 5.21(2H, s), 5.35(2H, ABq, J=13.2Hz), 8.20(4H, d, J=8.6Hz) |
| | HE | H | H | —N(CH₃)₂ | UV$\lambda_{max}^{H2O}$ nm:<br>IR$\nu_{max}^{KBr}$ (cm⁻¹): | 286<br>1750, 1630(sh), 1610, 1395, 1250 |
| 70 | HE | PNZ | PNB | —N⟨pyrrolidine⟩ | IR$\nu_{max}^{CHCl_3}$ (cm⁻¹):<br>[α]$_D^{25}$ −33°<br>NMRδ (CDCl₃): | 3400, 1775, 1707, 1642, 1608, 1526, 1445, 1345<br>(c=0.11, CHCl₃)<br>1.33(3H, d, J=6.15Hz), 1.40(3H, d, J=6.8Hz), 5.20(2H, s), 5.35(2H, ABq, J=13.8Hz), 7.47(2H, d, J=8.8Hz), 7.64(2H, d, J=8.8Hz), 8.20(2H, d, J=8.8Hz) |

TABLE 6-continued

| | | | | | |
|---|---|---|---|---|---|
| | HE | H | H | ![pyrrolidine]  −N⟨⟩ | UVλ$_{max}^{H2O}$ nm: 288 |
| | | | | | IRν$_{max}^{KBr}$ (cm$^{-1}$): 1760, 1635(sh), 1610, 1450, 1380, 1240 |

Structure: D-trans $R_1$—[β-lactam core]—S—[pyrrolidine with COY, N-$R_2$], COOR$_3$

| Example No. | $R_1$ | $R_2$ | $R_3$ | Y | Spectral Data | |
|---|---|---|---|---|---|---|
| 71 | HE | PNZ | PNB | —N(CH$_3$)$_2$ | IRν$_{max}^{CHCl3}$ (cm$^{-1}$): | 3400, 1770, 1700, 1650, 1605, 1520, 1400, 1120 |
| | | | | | NMRδ (CDCl$_3$): | 1.33(3H, d, J=6.15Hz), 1.39(3H, d, J=6.8Hz), 2.98(3H, s), 2.92 and 3.12(3H, each s), 5.22(2H, s), 5.36(2H, ABq, J=13.5Hz), 7.50(2H, d, J=8.6Hz), 7.64(2H, d, J=8.6Hz), 8.21(4H, d, J=8.6Hz) |
| | HE | H | H | —N(CH$_3$)$_2$ | UVλ$_{max}^{H2O}$ nm: | 291 |
| | | | | | IRν$_{max}^{KBr}$ (cm$^{-1}$): | 1755, 1630(sh), 1610, 1390, 1250 |
| 72 | HE | PNZ | PNB | —N⟨⟩ (dihydropyrrole) | IRν$_{max}^{CHCl3}$ (cm$^{-1}$): | 3420, 1775, 1710, 1660, 1621, 1528, 1420, 1405, 1120 |
| | | | | | NMRδ (CDCl$_3$): | 1.33(3H, d, J=6.15Hz), 1.40(3H, d, J=6.6Hz), 4.20(2H, br. s), 5.23(2H, s), 5.84(2H, s), 7.50(2H, d, J=8.6Hz), 7.65(2H, d, J=8.6Hz), 8.15(2H, d, J=8.6Hz), 8.21(2H, d, J=8.6Hz) |
| | HE | H | H | —N⟨⟩ | UVλ$_{max}^{H2O}$ nm: | 283 |
| | | | | | IRν$_{max}^{KBr}$ (cm$^{-1}$): | 1750, 1640, 1610, 1455, 1400, 1250 |

Structure: D-cis

| Example No. | $R_1$ | $R_2$ | $R_3$ | Y | Spectral Data | |
|---|---|---|---|---|---|---|
| 73 | HE | PNZ | PNB | —N(CH$_3$)$_2$ | IRν$_{max}^{CHCl3}$ (cm$^{-1}$): | 3430, 1775, 1710, 1655, 1525, 1350, 1012 |
| | | | | | NMRδ (CDCl$_3$): | 1.34(3H, d, J=6.4Hz), 1.38(3H, d, J=6.8Hz), 2.92, 2.94, 2.98 and 3.08(6H, each S), 5.21(2H, s), 5.36(2H, ABq, J=13.9Hz), 7.50(2H, d, J=8.6Hz), 7.65(2H, d, J=8.6Hz 8.21(2H, d, J=8.6Hz) |
| | HE | H | H | —N(CH$_3$)$_2$ | UVλ$_{max}^{H2O}$ nm: | 297 |
| | | | | | IRν$_{max}^{KBr}$ (cm$^{-1}$): | 1755, 1630(sh), 1600, 1380, 1240 |

Structure (with S-S):

| Example No. | $R_1$ | $R_2$ | $R_3$ | Y | Spectral Data | |
|---|---|---|---|---|---|---|
| 74 | HE | PNZ | PNB | —NH$_2$ | [α]$_D^{33}$ +32° | (c=0.22, THF) |
| | | | | | IRν$_{max}^{Nujol}$ (cm$^{-1}$): | 1780, 1680, 1608, 1517, 1381, 1350 |
| | | | | | NMRδ (CDCl$_3$): | 1.18(3H, d, J=6Hz), 5.22(2H, s), 5.79(1H, s) |
| | HE | H | H | —NH$_2$ | UVλ$_{max}^{H2O}$ nm: | 322, 255 |
| | | | | | IRν$_{max}^{KBr}$ (cm$^{-1}$): | 1762, 1655, 1577, 1376 |
| | | | | | NMRδ (D$_2$O): | 1.29(3H, d, J=6.5Hz), 1.75-1.89(1H, m), 2.62-2.87(1H, m), 3.00-3.09(1H, m), 3.38-3.48(1H, m), 3.65-3.92(2H, m), 3.90(1H, dd, J=1.4Hz and J=6Hz), 4.17-4.30(1H, m), 5.68(1H, d, |

TABLE 6-continued

| | | | | | | |
|---|---|---|---|---|---|---|
| 75 | HE | PNZ | PNB |  | $[\alpha]_D^{27}$ +48°<br>IR$\nu_{max}^{CHCl_3}$ (cm$^{-1}$):<br><br>NMR$\delta$ (CDCl$_3$): | J=1.4Hz)<br>(c=0.31, CHCl$_3$)<br>1790, 1706, 1653, 1612, 1420, 1356, 1115<br>1.36(3H, d, J=6Hz), 5.22(2H, s), 5.75(1H, d, J=1.5Hz) |
| | HE | H | H |  | IR$\nu_{max}^{KBr}$ (cm$^{-1}$):<br>NMR$\delta$ (D$_2$O): | 1765, 1636, 1582, 1365<br>1.29(3H, d, J=6.4Hz), 1.80-2.08(5H, m), 2.88-3.05(1H, m), 3.34-3.61(5H, m), 3.64-3.74(1H, m), 3.93(1H, dd, J=1.4Hz and J=6Hz), 4.04(1H, quin, J=6.6Hz), 4.24(1H, quin, J=6.3Hz), 4.40(1H, t, J=8.2Hz), 5.70(1H, d, J=1.4Hz) |

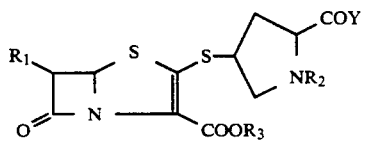

| Example<br>No. | R$_1$ | R$_2$ | R$_3$ | Y | | Spectral Data |
|---|---|---|---|---|---|---|
| 76 | H | PNZ | PNB | —NH$_2$ | IR$\nu_{max}^{Nujol}$ (cm$^{-1}$):<br>NMR$\delta$ (CDCl$_3$): | 1780, 1700, 1675, 1600, 1505<br>4.40(1H, t, J=7Hz), 5.25(2H, s), 5.37(1H, d, J=13.6Hz), 5.75(1H, dd, J=1.5Hz and J=3.5Hz), 7.47(2H, d, J=9Hz), 7.57(2H, d, J=9Hz), 8.16(4H, d, J=9Hz) |

According to the procedures as described in preceding Examples, the following compounds can also be prepared. In the following Tables, "Ph" means phenyl group.

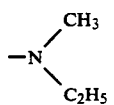

| Compound<br>No. | X | Y |
|---|---|---|
| 1 | —CH$_2$— | —NHC$_2$H$_5$ |
| 2 | —CH$_2$— | —NH-nC$_4$H$_9$ |
| 3 | —CH$_2$— | —NH-iC$_4$H$_9$ |
| 4 | —CH$_2$— | —N(nC$_3$H$_7$)$_2$ |
| 5 | —CH$_2$— | —N(iC$_3$H$_7$)$_2$ |
| 6 | —CH$_2$— | —N(nC$_4$H$_9$)$_2$ |
| 7 | —CH$_2$— | —N(iC$_4$H$_9$)$_2$ |
| 8 | —CH$_2$— | 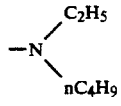 |
| 9 | —CH$_2$— | 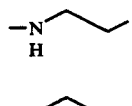 |
| 10 | —CH$_2$— | —N(H)CH$_2$CH$_2$Ph |
| 11 | —CH$_2$— | —N(CH$_3$)CH$_2$CH$_2$Ph |
| 12 | —CH$_2$— | —NCH$_2$—Ph<br>\|<br>C$_2$H$_5$ |
| 13 | —CH$_2$— | —N(CH$_2$—Ph)$_2$ |
| 14 | —CH$_2$— | 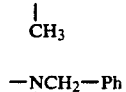 |
| 15 | —CH$_2$— | -N(CH$_3$)CH$_2$CH$_2$N(CH$_3$)$_2$ |
| 16 | —CH$_2$— | -N(C$_2$H$_5$)CH$_2$CH$_2$N(CH$_3$)$_2$ |
| 17 | —CH$_2$— | -N(C$_2$H$_5$)CH$_2$CH$_2$N(C$_2$H$_5$)$_2$ |
| 18 | —CH$_2$— | -N(H)CH$_2$CH$_2$CH$_2$N(CH$_3$)$_2$ |
| 19 | —CH$_2$— | -N(CH$_3$)CH$_2$CH$_2$CH$_2$N(CH$_3$)$_2$ |
| 20 | —CH$_2$— | -N(CH$_3$)CH$_2$CH$_2$CH$_2$N(CH$_3$)$_2$ |
| 21 | —CH$_2$— | -N(C$_2$H$_5$)CH$_2$CH$_2$CH$_2$N(CH$_3$)$_2$ |

-continued

| Compound No. | X | Y |
|---|---|---|
| 22 | —CH$_2$— | —N(C$_2$H$_5$)—CH$_2$CH$_2$CH$_2$—N(C$_2$H$_5$)$_2$ |
| 23 | —CH$_2$— | —N(CH$_3$)—CH$_2$CH$_2$CH$_2$—OH |
| 24 | —CH$_2$— | —N(CH$_3$)—CH(CH$_3$)—CH$_2$OH |
| 25 | —CH$_2$— | —N(CH$_3$)—CH$_2$CH(OH)CH$_3$ |
| 26 | —CH$_2$— | —NH—CH(CH$_3$)—CH$_2$OH |
| 27 | —CH$_2$— | —NH—C(CH$_3$)$_2$—CH$_2$OH |
| 28 | —CH$_2$— | —N(C$_2$H$_5$)—CH$_2$CH$_2$OH |
| 29 | —CH$_2$— | —N(CH$_2$CH$_2$OH)$_2$ |
| 30 | —CH$_2$— | —N(CH$_2$CH$_2$OH—)$_2$ |
| 31 | —CH$_2$— | 2-(N-methylcarbamoyl)pyrrolidin-1-yl |
| 32 | —CH$_2$— | 2-(N,N-dimethylcarbamoyl)pyrrolidin-1-yl |
| 33 | —CH$_2$— | 4-hydroxypiperidin-1-yl |
| 34 | —CH$_2$— | 3-hydroxypiperidin-1-yl |
| 35 | —CH$_2$— | 4-(N-methylcarbamoyl)piperidin-1-yl |
| 36 | —CH$_2$— | 4-(N,N-dimethylcarbamoyl)piperidin-1-yl |
| 37 | —CH$_2$— | 4-ethylpiperazin-1-yl |
| 38 | —CH$_2$— | —NH—CH$_2$CH$_2$—CONH$_2$ |
| 39 | —CH$_2$— | —NH—CH$_2$CH$_2$—CONHCH$_3$ |
| 40 | —CH$_2$— | —NH—CH$_2$CH$_2$—CON(CH$_3$)$_2$ |
| 41 | —CH$_2$— | —NH—CH$_2$CH$_2$CH$_2$—CONH$_2$ |
| 42 | —CH$_2$— | —NH—CH$_2$CH$_2$CH$_2$—CONHCH$_3$ |
| 43 | —CH$_2$— | —NH—CH$_2$CH$_2$CH$_2$—CON(CH$_3$)$_2$ |
| 44 | —CH(CH$_3$)— | —NH—CH$_2$CH=CH$_2$ |
| 45 | —CH(CH$_3$)— | —N(CH$_3$)—CH$_2$CH$_2$—N(CH$_3$)$_2$ |
| 46 | —CH(CH$_3$)— | —NH—CH$_2$CONHCH$_3$ |
| 47 | —CH(CH$_3$)— | —N(CH$_3$)—CH$_2$CONHCH$_3$ |
| 48 | —CH(CH$_3$)— | 4-carbamoylpiperidin-1-yl |
| 49 | —S— | —NH—CH$_2$CH=CH$_2$ |
| 50 | —S— | —N(CH$_3$)—CH$_2$CH$_2$—N(CH$_3$)$_2$ |
| 51 | —S— | —N(CH$_3$)—CH$_2$CH$_2$OH |
| 52 | —S— | —NH—CH$_2$CONH$_2$ |

| Compound No. | X | Y |
|---|---|---|
| 53 | —S— | —NCH₂CONH, with H on N and CH₃ on NH |
| 54 | —S— | —NCH₂CONHCH₃ with CH₃ on N |
| 55 | —S— | 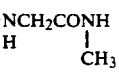 morpholino |
| 56 | —S— |  N-methylpiperazinyl |
| 57 | —S— | 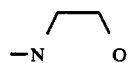 2,5-dihydropyrrolyl |
| 58 | —S— | 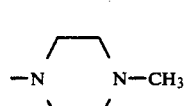 azetidinyl |
| 59 | —S— | 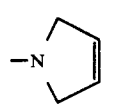 3-hydroxypyrrolidinyl |
| 60 | —S— |  4-carbamoylpiperidinyl |
| 61 | —S— | —OCH₃ |
| 62 | —CH(CH₃)— | 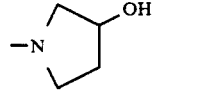 |
| 63 | —CH(CH₃)— |  |
| 64 | —CH₂— | 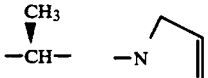 |
| 65 | —CH₂— | 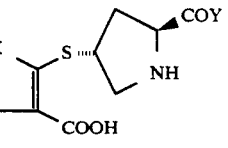 |
| Compound No. | X | Y |
|---|---|---|
| 66 | —S— |  |
| 67 | —S— | 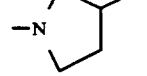 |
| 68 | —S— | 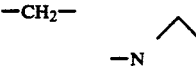 |
| 69 | —S— | —N(CH₃)₂ |
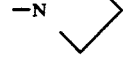
| 70 | —CH₂— (with CH₃) | 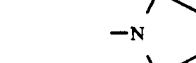 |
| 71 | —CH(CH₃)— | 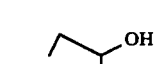 |
| 72 | —CH₂— |  |
| 73 | —CH₂— |  |
| 74 | —S— |  |
| 75 | —S— |  |
| 76 | —S— | 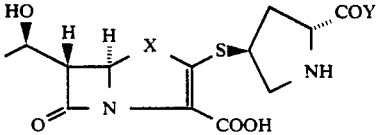 |
| 77 | —S— | —N(CH₃)₂ |
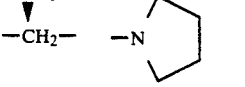

-continued

| Compound No. | X | Y |
|---|---|---|
| 78 | —CH— (CH₃) | —N(pyrrolidine) |
| 79 | —CH— (CH₃) | —N(2,5-dihydropyrrole) |
| 80 | —CH— (CH₃) | —N(azetidine) |
| 81 | —CH— (CH₃) | —N(3-hydroxypyrrolidine) |
| 82 | —CH— (CH₃) | —N(CH₃)CH₂CH₂OH |
| 83 | —CH₂— | —N(azetidine) |
| 84 | —CH₂— | —N(3-hydroxypyrrolidine) |
| 85 | —CH₂— | —N(morpholine) |
| 86 | —CH₂— | —N(CH₃)CH₂CH₂OH |
| 87 | —S— | —N(azetidine) |
| 88 | —S— | —N(pyrrolidine) |
| 89 | —S— | —N(3-hydroxypyrrolidine) |
| 90 | —S— | —N(CH₃)₂ |

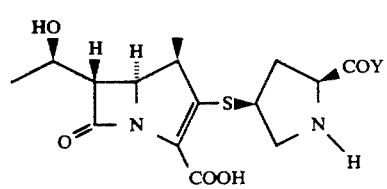

| | 91 | —NH₂ |

-continued

| Compound No. | X | Y |
|---|---|---|
| 92 | | —N(CH₃)CH₂CH₂OH |
| 93 | | —NHCH₂CONH₂ |
| 94 | | —N(CH₃)—CH₂CONH₂ |
| 95 | | —N(2,5-dihydropyrrole) |
| 96 | | —N(azetidine) |
| 97 | | —N(3-hydroxypyrrolidine) |
| 98 | | —N(morpholine) |
| 99 | | —N(N'-methylpiperazine) |
| 100 | | —OCH₃ |

What is claimed is:

1. A compound of the formula:

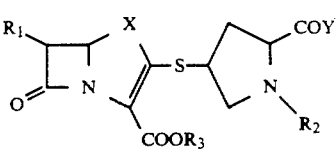

wherein R1 represents 1-hydroxyethyl or a protected 1-hydroxyethyl; R2 and R3 each independently represent a hydrogen atom or a protecting group; X represents an alkyl (C1-C3) substituted or unsubstituted methylene group; Y represents (1) an unsubstituted or alkyl (C1-C3) substituted guanidyl group, (2) an unsubstituted or substituted hydrazino group wherein the substituent is an alkyl (C1-C3) group, (3) a group represented by the formula (4-a): —NHOR8-a (4-a) wherein R8-a represents a hydrogen atom or an alkyl (C1-C3) group or (4) a group represented by the formula (2-a):

$$-N\begin{array}{c}R^5\\R^6\end{array} \quad (2\text{-}a)$$

wherein (A) R5 is (a) an alkyl (C1-C4) group which is substituted with a mono- or di-alkyl-(C1-C3)-substituted aminocarbonyl group or carboxyl group or (b) a pyridyl group and R6 is a hydrogen atom or an alkyl (C1-C4) group, or (B) R5 and R6 jointly represent an alkylene chain to form, together with the adjacent nitrogen atom, (a) a substituted 3- to 7-membered cyclic amino group wherein the substituent is an alkyl (C1-C3) group, carbamoyl group, a carboxyl group, a mono- or di-alkyl-(C1-C3) substituted aminocarbonyl group or a hydroxyl group, (b) an unsubstituted 3- to 7-membered cyclic amino group which may contain double bond(s) in the ring thereof, or (c)

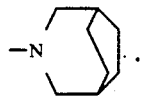

* * * * *